United States Patent [19]

Summers et al.

[11] Patent Number: 5,382,670
[45] Date of Patent: Jan. 17, 1995

[54] PLATELET ACTIVATING FACTOR ANTAGONISTS

[75] Inventors: James B. Summers, Libertyville; George S. Sheppard, Wilmette; James G. Phillips, Antioch; Daisy Pireh, Lincolnshire; Douglas H. Steinman, Morton Grove, all of Ill.; Paul D. May, Richland, Mich.; Denise E. Guinn, Grayslake, Ill.; H. Robin Heyman, Chicago, Ill.; George M. Carrera, Jr., Des Plaines, Ill.; Steven K. Davidsen, Mundelein, Ill.

[73] Assignee: Abbott Laboratories, Abbott Park, Ill.

[21] Appl. No.: 84,257

[22] PCT Filed: Feb. 14, 1992

[86] PCT No.: PCT/US92/01195

§ 371 Date: Jul. 7, 1993

§ 102(e) Date: Jul. 7, 1993

[51] Int. Cl.$^6$ .................. C07D 213/04; C07D 209/04; C07D 277/04
[52] U.S. Cl. ..................................... 546/273; 514/339
[58] Field of Search ......................... 546/273; 514/339

[56] References Cited

U.S. PATENT DOCUMENTS 5,120,749 6/1992 Summers ............................ 514/337

*Primary Examiner*—C. Warren Ivy
*Assistant Examiner*—D. Margaret M. Mach
*Attorney, Agent, or Firm*—Jerry F. Janssen

[57] ABSTRACT

Indole compounds substituted at the 1- or 3-position by a (pyrid-3-yl)thiazolid-4-yl)alkyl-, (pyrid-3-yl)thiazolid-4-oyl)-, (pyrid-3-yl)dithiolan-4-yl)alkyl- or (pyrid-3-yl)dithiolan-4-oyl)- group are potent inhibitors of PAF and are useful in the treatment of PAF-related disorders including septic shock, respiratory distress syndrome, acute inflammation, delayed cellular immunity, parturition, fetal lung maturation, and cellular differentiation.

12 Claims, No Drawings

PLATELET ACTIVATING FACTOR ANTAGONISTS

TECHNICAL FIELD

This invention relates to compounds having pharmacological activity, to compositions containing these compounds, and to a medical method of treatment employing the compounds and compositions. More particularly, this invention concerns certain pyridylthiazolidine, pyridyldithiolane, and pyridylpyrrolidine compounds and their salts which have platelet activating factor (PAF antagonist activity, to pharmaceutical compositions containing these compounds, and to a method of treating PAF-mediated disorders.

BACKGROUND OF THE INVENTION

Platelet activating factor (PAF) is a phospholipid released from human and other animal cells and is an acetylglyceryl ether of phosphorylcholine as represented by the following formula:

$$\begin{array}{c} CH_2O(CH_2)_nCH_3 \\ | \\ CH_3COO-CH \quad O \\ | \quad \| \\ CH_2O-P-O(CH_2)_2-N^+(CH_3)_3 \\ | \\ O^- \end{array}$$

where n is 15 or 17.

PAF is physiologically active and causes contraction of the airway smooth muscle, increased vascular permeability, platelet aggregation, hypotension and the like. It is now recognized as a powerful mediator of intimation and may play a physiological or pathobiologic role in a variety of clinical conditions, such as endotoxin- and IgG-induced shock (septic shock), asthma and pulmonary dysfunction, acute inflammation, transplanted organ rejection, thrombosis, cardiac anaphylaxis, gastrointestinal ulceration, allergic skin diseases, retinal and corneal diseases, chemically induced liver cirrhosis, and ovimplantation in pregnancy.

Several PAF antagonists have been reported (e.g., U.S. Pat. No. 4,948,795, European Patent Application EP 279681, and U.S. Pat. No. 4,786,645) but none have received wide acceptance. Therefore, there is a continuing need for the development of potent antagonists of PAF which have low toxicity.

SUMMARY OF THE INVENTION

The present invention provides, in its principal aspect, compounds having PAF antagonist activity of the formula:

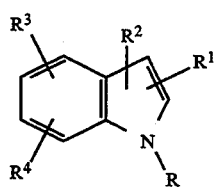

where R is B where B is

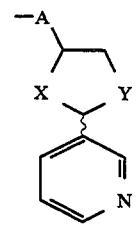

in which A is methylene, hydroxymethyl, or carbonyl, X is sulfur, or $NR^5$ where $R^5$ is hydrogen, alkyl of from one to six carbon atoms, formyl, alkoyl of from one to six carbon atoms, alkylsulfonyl of from one to six carbon atoms, trihaloacetyl, or $—C(O)NR^6R^7$ where $R^6$ and $R^7$ are independently selected from hydrogen and alkyl of from one to six carbon atoms. The group Y is sulfur or methylene.

Alternatively, R is selected from (a) hydrogen; (b) alkyl of from one to six carbon atoms; (c) $—(CH_2)_n-C(O)NR^6R^7$ where $R^6$ and $R^7$ are as previously defined and where n is from zero to four, (d) $—(CH_2)_n-C(O)OR^8$ where $R^8$ is alkyl of from one to six carbon atoms, phenyl, optionally substituted with alkyl of from one to six carbon atoms, alkoxy of from one to six carbon atoms, or halogen; phenylalkyl in which the alkyl portion contains from one to four carbon atoms, alkoxy of from one to six carbon atoms, or halogen, and where n is as previously defined; (e) $—(CH_2)_nC(O)R^9$ where n is as previously defined and $R^9$ is hydrogen or alkyl of from one to six carbon atoms; (f) $—(CH_2)_mCOOH$ where m is from one to four, (g) $—(CH_2)_mNR^6R^7$ where m, $R^6$, and $R^7$ are as previously defined; (h) $—(CH_2)_nSO_2R^8$ where n and $R^8$ are as previously defined; (i) $—(CH_2)_nSO_2NR^6R^7$ where n, $R^6$, and $R^7$ are as previously defined; (j) phenylalkyl in which the alkyl portion contains from one to six carbon atoms; and (k) benzoyl, optionally substituted with halogen, alkyl of from one to six carbon atoms, or alkoxy of from one to six carbon atoms.

$R^1$ is hydrogen or B with the proviso that one of R or $R^1$ is B, but R and $R^1$ are not both B.

$R^2$ is selected from hydrogen or alkyl of from one to six carbon atoms.

$R^3$ and $R^4$ are independently selected from the group consisting of (a) hydrogen; (b) halogen; (c) alkyl of from one to six carbon atoms; (d) alkoxy of from one to carbon atoms; (e) alkoyl of from one to six carbon atoms; (f) cyano; (g) phenylalkoxy in which the alkoxy portion contains from one to six carbon atoms; (h) phenoxy; (i) benzoyl, optionally substituted with alkyl of from one to six carbon atoms, alkoxy of from one to six carbon atoms, or halogen; (j) $—NR^6R^7$ where $R^6$ and $R^7$ are as previously defined; (k) $—C(O)OR^9$ where $R^9$ is as previously defined; and (l) phenyl, optionally substituted with alkyl of from one to six carbon atoms, alkoxy of from one to six carbon atoms, or halogen.

The pharmaceutically acceptable salts, and individual stereoisomers of compounds of structural formula I above, as well as mixtures thereof, are also contemplated as falling within the scope of the present invention.

In another aspect, the present invention provides pharmaceutical compositions useful for the treatment of PAF-mediated disorders comprising a therapeutically effective amount of a compound of formula I above in combination with a pharmaceutically acceptable carrier.

In another aspect, the present invention provides a method of inhibiting PAF activity by administering to a host mammal in need of such treatment a PAF-inhibiting effective amount of a compound of structure I above.

In yet another aspect of the present invention, there is provided a method of treating PAF-mediated disorders including septic shock, asthma, anaphylactic shock, respiratory distress syndrome, acute inflammation, delayed cellular immunity, parturition, fetal lung maturation, and cellular differentiation by administering to a host mammal in need of such treatment a therapeutically effective amount of a compound of structure I above.

DETAILED DESCRIPTION AND PREFERRED EMBODIMENTS

In one particular embodiment, compounds of the present invention are represented by formula II:

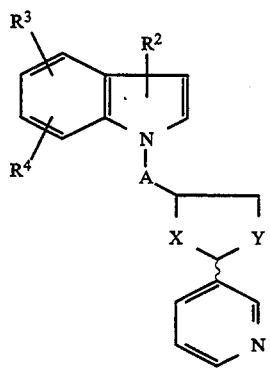

II where A, X, Y, $R^2$, $R^3$, and $R^4$ are as defined above.

Preferred compounds of formula II are those in which A is carbonyl, X is $NR^5$ (where $R^5$ is as defined above) and Y is sulfur, $R^2$ is hydrogen or alkyl of from one to six carbon atoms, and $R^3$ is hydrogen, halogen, or phenylalkoxy in which the alkoxy portion contains from one to six carbon atoms, and $R^4$ is hydrogen. Particularly preferred are compounds of formula II in which $R^2$ is hydrogen or methyl; $R^3$ is selected from hydrogen, 5-phenylalkoxy, or 5-halo; and $R^5$ is hydrogen.

In another embodiment, compounds of the present invention are represented by formula III:

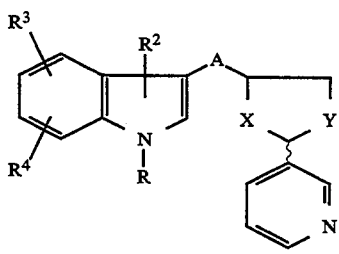

III where A, X, Y, R, $R^2$, $R^3$, and $R^4$ are as defined above.

Preferred compounds of formula III are those in which A is carbonyl, X is $NR^5$ (where $R^5$ is as defined above) and Y is sulfur, $R^2$ is hydrogen, R is selected from hydrogen, $—(CH_2)_nC(O)NR^6R^7$ (where n, $R^6$ and $R^7$ are as defined above), $—(CH_2)_nC(O)OR^8$ (where n and $R^8$ is as defined above), or $—(CH_2)_mCOOH$ (where m is as defined above); $R^3$ is hydrogen, alkyl of from one to six carbon atoms, or phenylalkoxy in which the alkoxy portion contains from one to six carbon atoms: and $R^4$ is hydrogen. Particularly preferred compounds of formula III are those in which R and $R^5$ are hydrogen, $—C(O)N(CH_3)_2$, $—CH_2C(O)N(CH_3)_2$, $—CH_2COOH$, $—CH_2CH_2COOH$ or tert-butoxycarbonyl; $R^3$ is hydrogen, phenylmethoxy, or methyl; $R^2$ and $R^4$ is hydrogen.

Examples of compounds contemplated as falling within the scope of the present invention include, but are not necessarily limited to:

1-[2-(3-pyridinyl)thiazolid-4-oyl]indole;
1-[2-(3-pyridinyl)thiazolid-4-oyl]-2,5-dimethylindole;
1-[2-(3-pyridinyl)thiazolid-4-oyl]-4-chloroindole;
1-[2-(3-pyridinyl)thiazolid-4-oyl]-4-bromoindole;
1-[2-(3-pyridinyl)thiazolid-4-oyl]-5-chloroindole;
1-[2-(3-pyridinyl)thiazolid-4-oyl]-6-fluoroindole;
1-[2-(3-pyridinyl)thiazolid-4-oyl]-6-chloroindole;
1-[2-(3-pyridinyl)thiazolid-4-oyl]-6-bromoindole;
1-[2-(3-pyridinyl)thiazolid-4-oyl]-5-cyanoindole;
1-[2-(3-pyridinyl)thiazolid-4-oyl]-5,6-dimethoxyindole;
1-[2-(3-pyridinyl)thiazolid-4-oyl]-5-phenylmethoxyindole;
1-[2-(3-pyridinyl)thiazolid-4-oyl]-6-phenylmethoxyindole;
1-[2-(3-pyridinyl)-thiazolid-4-oyl]-4-benzoylindole;
1-[2-(3-pyridinyl)thiazolid-4-oyl]-4-(3,4,5-trimethoxybenzoyl)indole;
1-[2-(3-pyridinyl)thiazolid-4-oyl]-6-benzoylindole;
3-[2-(3-pyridinyl)thiazolid-4-ylmethyl]indole;
3-[2-(3-pyridinyl)thiazolid-4-oyl]indole;
1-methyl-3-[2-(3-pyridinyl)thiazolid-4-oyl]indole;
2-methyl-3-[2-(3-pyridinyl)thiazolid-4-oyl]indole;
7-methyl-3-[2-(3-pyridinyl)thiazolid-4-oyl]indole;
1,2-dimethyl-3-[2-(3-pyridinyl)thiazolid-4-oyl]indole;
1-ethyl-3-[2-(3-pyridinyl)thiazolid-4-oyl]indole;
1-pivaloyl-3-[2-(3-pyridinyl)thiazolid-4-oyl]indole;
1-phenylmethyl-3-[2-(3-pyridinyl)thiazolid-4-oyl]indole;
3-[2-(3-pyridinyl)thiazolid-4-oyl]-4-phenylmethoxyindole;
3-[2-(3-pyridinyl)thiazolid-4-oyl]-5-phenylmethoxyindole;
3-[2-(3-pyridinyl)thiazolid-4-oyl]-6-phenylmethoxyindole;
3-[2-(3-pyridinyl)thiazolid-4-oyl]-7-phenylmethoxyindole;
1-methylsulfonyl-3-[2-(3-pyridinyl)thiazolid-4-oyl]indole;
1-iso-propylsulfonyl-3-[2-(3-pyridinyl)thiazolid-4-oyl]indole;
1-phenylsulfonyl-3-[2-(3-pyridinyl)thiazolid-4-oyl]indole;
1-(4-chlorobenzoyl)-3-[2-(3-pyridinyl)thiazolid-4-oyl]indole;
1-tert-butoxycarbonyl-3-[2-(3-pyridinyl)thiazolid-4-oyl]indole;
1-tert-butoxycarbonyl-6-phenylmethoxy-3-[2-(3-pyridinyl)thiazolid-4-oyl]indole;
1-tert-butoxycarbonyl-2-methyl-3-[2-(3-pyridinyl)-thiazolid-4-oyl]indole;
1-ethoxycarbonyl-3-[2-(3-pyridinyl)thiazolid4-oyl]indole;
1-methoxycarbonyl-3-[2-(3-pyridinyl)thiazolid-4-oyl]indole;
1-tert-butoxycarbonyl-7-phenylmethoxy-3-[2-(3-pyridinyl)thiazolid-4-oyl]indole;

1-tert-butoxycarbonyl-3-[2-(3-pyridinyl)-3-formylcarbonylthiazolid-4-oyl]indole;
1-tert-butoxycarbonyl-3-[2-(3-pyridinyl)-3-acetylthiazolid-4-oyl]indole;
1-phenylmethoxycarbonyl-3-[2-(3-pyridinyl)thiazolid-4-oyl]indole;
1-dimethylcarbamoyl)-3-[2-(3-pyridinyl)thiazolid-4-oyl]indole;
1-diethylcarbamoyl)-3-[2-(3-pyridinyl)thiazolid-4-oyl]indole;
1-dimethylcarbamoyl)-7-phenylmethoxy-3-[2-(3-pyridinyl)thiazolid-4-oyl]indole;
1-dimethylcarbamoyl)-6-phenylmethoxy-3-[2-(3-pyridinyl)thiazolid-4-oyl]indole;
1-(N-tert-butoxycarbamoyl)-3-[2-(3-pyridinyl)thiazolid-4-oyl]indole;
1-(4-morpholinocarbonyl)-3-[2-(3-pyridinyl)thiazolid-4-oyl]indole;
1-[2-(3-pyridinyl)dithiolan-4-oyl]indole;
3-[2-(3-pyridinyl)dithiolan-4-oyl]indole;
1-phenylsulfonyl 3-[2-(3-pyridinyl)dithiolan-4-oyl]indole;
cis-1-tert-butoxycarbonyl-3-[2-(3-pyridinyl)dithiolan-4-oyl]indole;
trans-1-tert-butoxycarbonyl-3-[2-(3-pyridinyl)dithiolan-4-oyl]indole;
1-(N-methyl, N-phenylcarbamoyl)-3-[2-(3-pyridinyl)thiazolid-4-oyl]indole;
1-tert-butoxycarbonyl-3-[2-(3-pyridinyl)-3-carbamoylthiazolid-4-oyl]indole;
1-trifluoroethyl-3-[2-(3-pyridinyl)thiazolid-4-oyl]indole;
1-ethoxycarbonylmethyl-3-[2-(3-pyridinyl)thiazolid-4-oyl]indole;
1-propyl-3-[2-(3-pyridinyl)thiazolid-4-oyl]indole;
1-ethylsulfonyl3-[2-(3-pyridinyl)thiazolid-4-oyl]indole;
1-(N-methylcarbamoyl)-3-[2-(3-pyridinyl)thiazolid-4-oyl]indole;
1-(4-morpholinocarbonyl)-2-methyl-3-[2-(3-pyridinyl)thiazolid-4-oyl]indole;
1-dimethylcarbamoyl-2-methyl-3-[2-(3-pyridyl)thiazolid-4-oyl]indole;
2,5-dimethyl -3-[2-(3-pyridinyl)thiazolid-4-oyl]indole;
1-tert-butoxycarbonyl-2,5-dimethyl-3-[2-(3-pyridinyl)thiazolid-4-oyl]indole;
1-(4-morpholinocarbonyl)-2,5-dimethyl-3-[2-(3-pyridinyl)thiazolid-4-oyl]indole;
1-dimethylcarbamoyl-2,5-dimethyl-3-[2-(3-pyridinyl)thiazolid-4-oyl]indole;
3-[2-(3-pyridinyl)thiazolid-4-oyl]-6-(4-fluorophenoxy)indole;
1-dimethylcarbamoyl-3-[2-(3-pyridinyl)thiazolid-4-oyl]-6-(4-fluorophenoxy)indole;
1-(4-morpholinocarbonyl)-3-[2-(3-pyridinyl)thiazolid-4-oyl]-6phenylmethoxyindole;
1-ethylsulfonyl-3-[2-(3-pyridinyl)thiazolid-4-oyl]-6-phenylmethoxyindole;
3-[2-(3-pyridinyl)thiazolid-4-oyl]-6-(4-fluorophenylmethoxy)indole;
1-dimethylcarbamoyl-3-[2-(3-pyridinyl)thiazolid-4-oyl]-6-(4-fluorophenylmethoxy)indole;
3-2-(3-pyridinyl)thiazolid-4-oyl]-6-(3-methylpyridinyl)indole;
3-[2-(3-pyridinyl)thiazolid-4-oyl]-6-phenylethynylindole;
1-dimethylcarbamoyl-3-[2-(3-pyridinyl)thiazolid-4-oyl]-6-phenylethynyl indole;
2-methyl-3-[2-(3-pyridinyl)thiazolid-4-oyl]-6-phenylmethoxyindole;
3-[2-(3-pyridinyl)thiazolid-4-oyl]-6-methylindole;
1-tert-butoxycarbonyl-3-[2-(3-pyridinyl)thiazolid-4-oyl]-6-methylindole;
3-[2-(3-pyridinyl)thiazolid-4-oyl]-6-methoxyindole
1-tert-butoxycarbonyl-3-[2-(3-pyridinyl)thiazolid-4-oyl]-6-methoxyindole;
1-dimethylcarbamoyl-3-[2-(3-pyridinyl)thiazolid-4-oyl]-6-methoxyindole;
3-[2-(3-pyridinyl)-thiazolid-4-oyl ]-6-phenylindole;
1-dimethylcarbamoyl-3-[2-(3-pyridinyl)thiazolid-4-oyl]-6-phenylindole;
3-[2-(3-pyridinyl)thiazolid-4-oyl]-6-hydroxyindole;
1-dimethylcarbamoyl-3-[2-(3-pyridinyl)thiazolid-4-oyl]-6-chloroindole;
3-[2-(3-pyridinyl)-3-formylthiazolid-4-oyl]indole;
1-dimethylcarbamoyl-3-[2-(3-pyridinyl)-3-formylthiazolid-4-oyl]indole;
1-(4-morpholinocarbonyl)-3-[2-(3-pyridinyl)-3-formylthiazolid-4-oyl ]indole;
1-dimethylcarbamoyl-3-[2-(3-pyridinyl)-3-formylthiazolid-4-oyl]-6-phenylmethoxyindole;
1-dimethylcarbamoyl-3-[2-(3-pyridinyl)-3-formylthiazolid-4-oyl]-6-methylindole;
1-dimethylcarbamoyl-3-[1-oxide-2-(3-pyridinyl)-3-formylthiazolid-4-oyl]indole;
trans-1-dimethylcarbamoyl-3-[2-(3-pyridinyl)-3-formylthiazolid-4-oyl]indole;
cis-1-dimethylcarbamoyl-3-[2-(3-pyridinyl)-3-formylthiazolid-4-oyl]indole;
3-[2-(3-pyridinyl)-3-acetylthiazolid-4-oyl]indole;
1-dimethylcarbamoyl-3-[2-(3-pyridinyl)-3-acetylthiazolid-4-oyl]-6-phenylmethoxyindole;
1-dimethylcarbamoyl-3-[2-(3-pyridinyl)-3-acetylthiazolid-4-oyl]indole;
3-[2-(3-pyridinyl)-3-trifluoroacetylthiazolid-4-oyl]indole, isomer 1;
3-[2-(3-pyridinyl)-3-trifluoroacetylthiazolid-4-oyl]indole, isomer 2;
cis-1-dimethylcarbamoyl-3-[2-(3-pyridinyl)-3-trifluoroacetylthiazolid-4-oyl]indole;
trans-1-dimethylcarbamoyl-3-[2-(3-pyridinyl)-3-trifluoroacetylthiazolid-4-oyl]indole;
1-dimethylcarbamoyl-3-[2-(3-pyridinyl)-3-trifluoroacetylthiazolid-4-oyl]-6-phenylmethoxyindole, isomer 1;
1-dimethylcarbamoyl-3-[2-(3-pyridinyl)-3-trifluoroacetylthiazolid-4-oyl]-6-phenylmethoxyindole, isomer 2;
1-dimethylcarbamoyl-3-[2-(3-pyridinyl)-3-carbamoylthiazolid-4-oyl]indole;
1-dimethylcarbamoyl-3-[2-(3-pyridinyl)-3-carbamoylthiazolid-4-oyl]-6-phenylmethoxyindole;
1-dimethylcarbamoyl-3-[2-(3-pyridinyl)-3-methylsulfonylthiazolid-4-oyl]indole;
1-dimethylcarbamoyl-3-[2-(3-pyridinyl)-3-formyloxazolid-4-oyl]indole;
[2-(3-pyridinyl)thiazolid-4-yl](1-tert-butoxycarbonylindol-3-yl)methanol;
2-[2-(3-pyridinyl)thiazolid-4-oyl]indole;
1-(N,N-dimethylcarbamoylmethyl)-3-[2-(3-pyridinyl)thiazolid-4-oyl]indole;
1-(N-methylcarbamoylmethyl)-3-[2-(3-pyridinyl)thiazolid-4-oyl]indole;
1-carbomethoxyethyl-3-[2-(3-pyridinyl)thiazolid-4-oyl]indole;
1-carboxyethyl-3-[2-(3-pyridinyl)thiazolid-4-oyl]indole;

1-carboxymethyl-3-[2-(3-pyridinyl)thiazolid-4-oyl]indole;

1-carbamoylmethyl-3-[2-(3-pyridinyl)thiazolid-4-oyl]indole;

3-[2-(3-pyridinyl)thiazolid-4-oyl]-6-carbomethoxyindole; and the pharmaceutically acceptable salts thereof.

As used throughout this specification and the appended claims, the following terms have the meanings ascribed to them:

The term "carbamoyl" refers to a structure of formula —CONR$^6$R$^7$ wherein R$^6$ and R$^7$ are independently selected from hydrogen or a straight or branched alkyl radical of from one to six carbon atoms. Representative examples of carbamoyl groups, include —C(O)NH$_2$, N,N-dimethylcarbamoyl, N-tert-butylcarbamoyl, N-methyl-N-ethylcarbamoyl and the like.

The term "carboalkoxy" as used herein refers to a structure of formula —C(O)OR$^8$ wherein R$^8$ is a straight or branched alkyl radical of from one to six carbon atoms, phenyl or substituted phenyl. Representative examples of carboalkoxy groups include carbomethoxy, carboethoxy, carbo(iso-propoxy), carbobutoxy, carbo(sec-butoxy), carbo(iso-butoxy), carbo(tert-butoxy), phenoxycarbonyl, and the like.

The term "alkoyl" as used herein refers to formyl and radicals of the structure —C(O)-alkyl in which the alkyl portion is a straight or branched alkyl group of from one to six carbon atoms. Representative examples of alkoyl groups include formyl, acetyl, propionyl, butyryl, iso-butyryl, pivaloyl, and the like.

The term "alkoxy" as used herein refers to a lower alkyl group, as defined herein, which is bonded to the parent molecular moiety through an oxygen atom Representative examples of alkoxy groups include methoxy, ethoxy, tert-butoxy, and the like.

The term "alkyl" as used herein refers to straight or branched chain radicals derived from saturated hydrocarbons by the removal of one hydrogen atom. Representative examples of alkyl groups include methyl, ethyl, n-propyl, iso-propyl, n-butyl, sec-butyl, iso-butyl, tert-butyl, and the like.

The term "alkylsufonyl" is used herein to mean —SO$_2$(alkyl) where the alkyl group is as defined above. Representative examples of lower alkylsufonyl groups include methylsulfonyl, ethylsufonyl, isopropylsulfonyl and the like.

The terms "PAF-related disorders" and "PAF-mediated disorders" are used herein to mean disorders related to PAF or mediated by PAF, including septic shock, asthma, anaphylactic shock, respiratory distress syndromes, acute inflammation, delayed cellular immunity, parturtition, fetal lung maturation, and cellular differentiation.

The term "phenylalkoxy" is used herein to mean an phenyl group appended to an alkoxy radical as previously defined. Representative examples of phenylalkoxy groups include phenylmethoxy (i.e. benzyloxy), 1-phenylethoxy, 2-phenylethoxy, 2-phenylpropoxy, and the like.

The term "pharmaceutically acceptable salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate. lactiobionate, laurylsulphonate salts and the like. (See, for example S. M. Berge, et al., "Pharmaceutical Salts," J. Pharm. Sci., 66:1-19 (1977) which is incorporated herein by reference.)

When necessary, individual enantiomeric forms of compounds of the present invention can be separated from mixtures thereof by techniques well known in the art. For example, a mixture of diastereomeric salts may be formed by reacting the compounds of the present invention with a optically pure form of an acid, followed by purification of the mixture of diastereomers by recrystallization or chromatography and subsequent recovery of the resolved compound from the salt by basification. Alternatively, the optical isomers of the compounds of the present invention can be separated from one another by chromatographic techniques employing separation on an optically active chromatgraphic medium. The members of the pyridylthiazolidine class can be obtained as the prefered pure R -enantiomeric form by choosing the naturally occuring R -enantiomer of the amino acid cysteine as the starting material (vide infra).

The present invention also provides pharmaceutical compositions which comprise one or more of the compounds of formula I above formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions suspensions or emulsions as well as sterile powders for reconstitution into sterile injectable solutions or dispersions just prior to use. Examples of suitable aqueous and nonaqueous careers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a as bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary) ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain pan of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, as cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or careers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p 33 et seq.

Dosage forms for topical administration of a compound of this invention include powders, sprays, ointments and inhalants. The active compound is mixed under sterile conditions with a pharmaceutically acceptable career and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.001 to about 100, more preferably of about 0.01 to about 20, and most preferably about 0.1 to about 10 mg of active compound per kilogram of body weight per day are administered orally to a mammalian patient. If desired, the effective daily dose may be divided into multiple doses for purposes administration, e.g. two to four separate doses per day.

In general, the compounds of this invention are synthesized by reaction Schemes I though XIII as illustrated below. It should be understood that X, Y, A, $R_1$, and $R_2$ as used herein correspond to the groups identified by Formula I.

The compounds of Formula (I) may be prepared using the reactions and techniques described in this section. The reactions are performed in a solvent appropriate to the reagents and materials employed and suitable for the transformation being effected. It is understood by those skilled in the art of organic synthesis that the functionality present on the heterocycle and other portions of the molecule must be consistent with the chemical transformation proposed. This will frequently necessitate judgement as to the order of synthetic steps, protecting groups required and deprotection conditions.

Scheme I

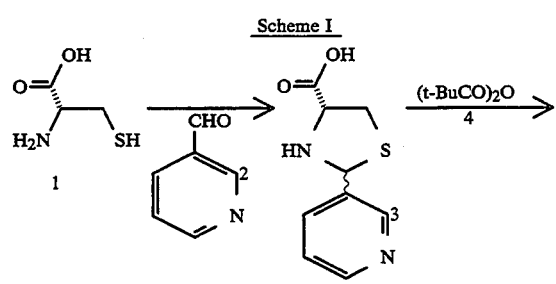

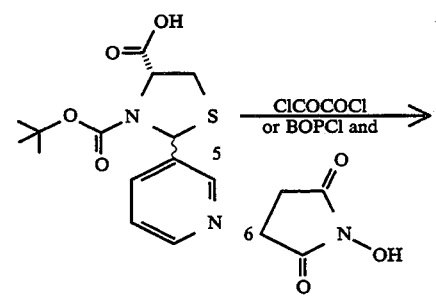

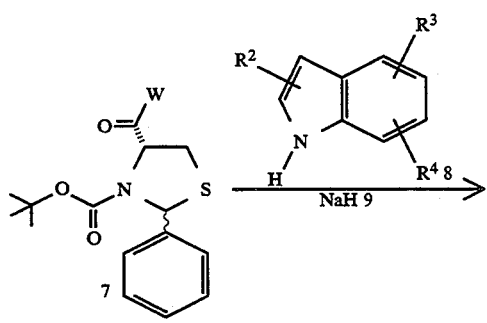

-continued
Scheme I

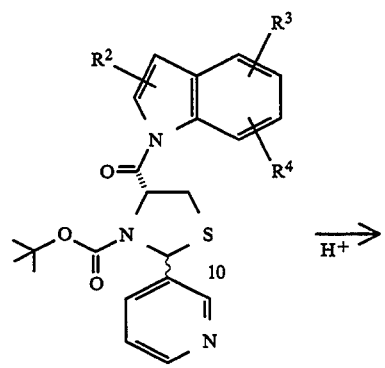

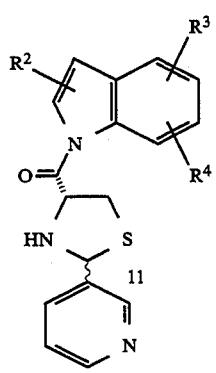

According to the foregoing reaction scheme I, L-cysteine (1) is condensed with 3-pyridine aldehyde (2) to produce 2-(3-pyridinyl)-4-thiazolidinecarboxylic acid (3). The thiazolidine nitrogen is protected with an appropriate group, preferably carbo-tert-butoxy (BOC) with di-tert-butyl dicarbonate (4). The resulting 2-(3-pyridinyl)-3-tert-butoxycarbonyl-4-thiazolidinecarboxylic acid (5) is converted to an active ester (7), preferably the acid chloride (W is Cl), through the action of oxalyl chloride, or the N-hydroxysuccinimide ester (W is O-succinimide) through the action of N-hydroxysuccinimide and a coupling agent such as dicyclohexylcarbodiimide or bis (2-oxo-3-oxazolidinyl)phosphinic chloride. The anion of an unsubstituted or substituted indole (8) is prepared by the reaction of the indole with a strong base, preferably sodium hydride (9) and the this anion is reacted with the active ester (7) to give the 1-[2-(3-pyridinyl)-3-tert-butoxycarbonyl-thiaz-4-oyl]indole (10). The BOC protecting group can be removed with acid, preferably HCl, to the produce 1-[2-(3-pyridinyl)-thiazolid-4-oyl]indole (11).

Scheme II

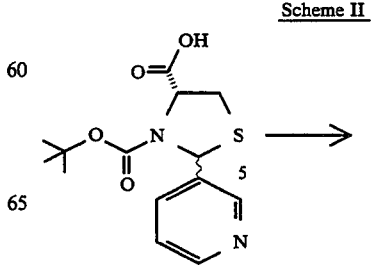

Scheme II -continued

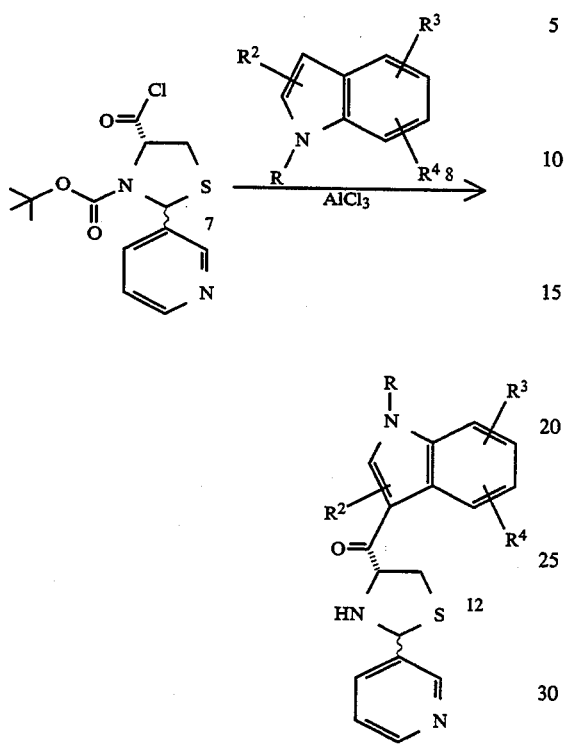

According to the foregoing reaction scheme II, 2-(3-pyridinyl)-3-tert-butoxycarbonyl-4-thiazolidinecarboxylic acid (5) is converted to the acid chloride (7), preferably by treatment with oxalyl chloride or thionyl chloride. Alternatively the acid (5) may first be convened to its salt by treatment with a base, such as sodium hydride, and then treated with oxalyl chloride or thionyl chloride to afford 7. Reaction of the acid chloride (7) with a Lewis acid, preferably aluminum chloride, followed by an unsubstituted or substituted indole (8) yields the 3-[2-(3-pyridinyl)-thiazolid-4-oyl]indole (12).

Scheme III -continued

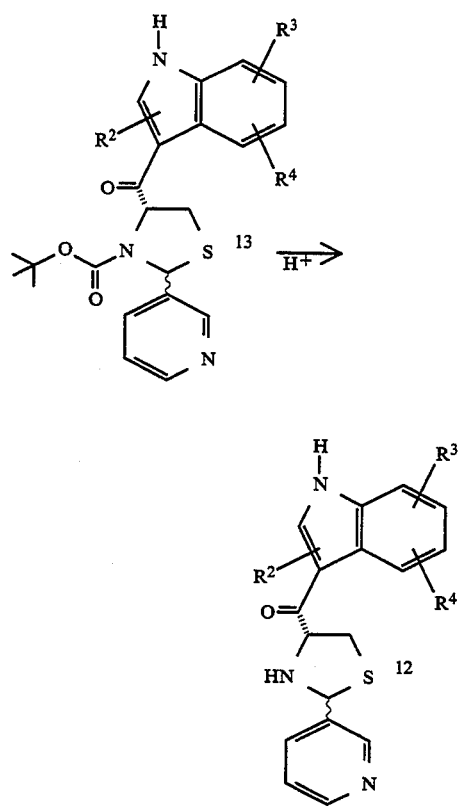

According to the foregoing reaction scheme III, an active ester of 2-(3-pyridinyl)-3-tert-butoxycarbonyl-4-thiazolidinecarboxylic acid (7), preferably acid chloride (W is Cl) or the N-hydroxylsuccinimide ester, prepared as described in scheme I, is treated with the anion of an unsubstituted or substituted indole (8) in a solvent, preferably benzene, to give a 3-[2-(3-pyridinyl)-3-tert-butoxycarbonylthiazolid-4-oyl]indole (13). The anion is prepared from the indole and a strong base, preferably ethyl magnesium bromide. The BOC group is removed from 13 by treatment with an acid, preferably HCl.

Scheme III

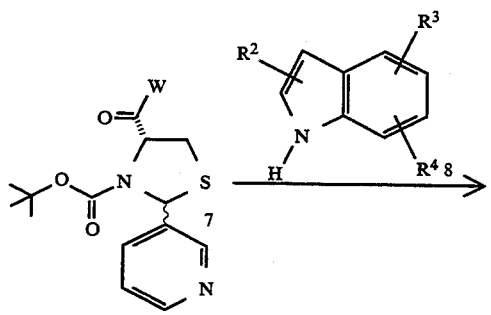

Scheme IV

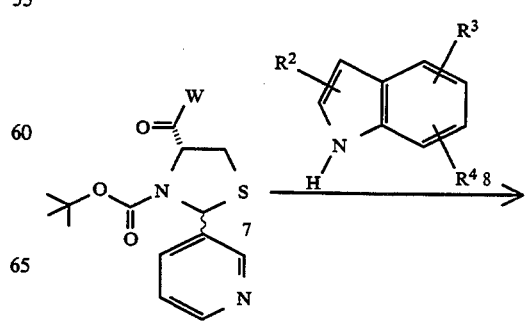

-continued
Scheme IV

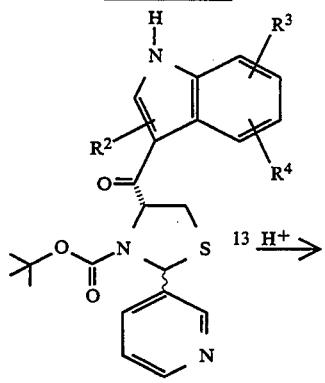

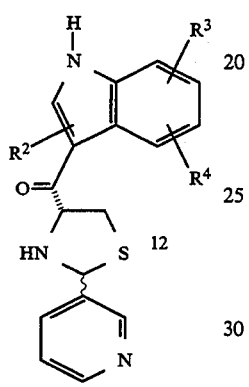

-continued
Scheme V

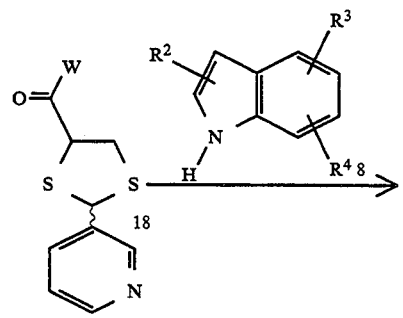

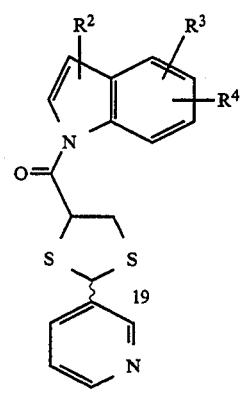

According to the foregoing reaction scheme IV, an active ester of 2-(3-pyridinyl)-3-tert-butoxycarbonyl-4-thiazolidinecarboxylic acid (7), preferably the acid chloride (W is Cl), prepared as described in scheme I, is treated with the zinc salt of an unsubstituted or substituted indole (8) in a solvent, preferably diethyl ether, to give a 3-[2-(3-pyridinyl)-3-tert-butoxycarbonylthiazolid-4-oyl]indole (13). The zinc salt is prepared from the indole and a strong base, preferably ethyl magnesium bromide, followed by the addition of an anhydrous inorganic zinc salt, preferably zinc (II) chloride The BOC group is removed from 13 by treatment with an acid, preferably HCl.

Scheme V

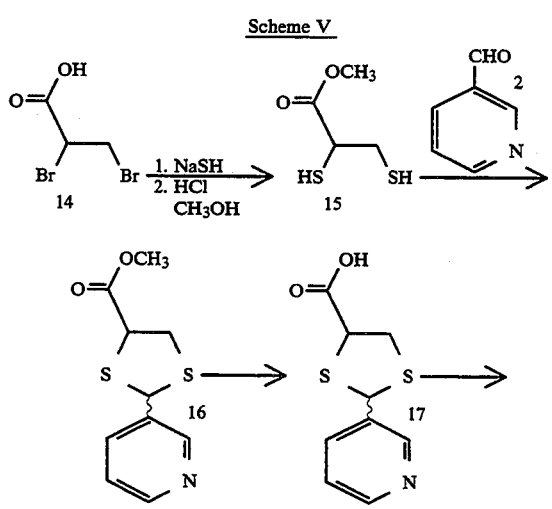

According to the foregoing reaction scheme V, 2,3-dibromopropionic acid (14) is treated with NaSH followed by esterification with HCl in methanol to give methyl 2,3-dimercaptopropenonate (15). This dithiol (15) is condensed with 3-pyridine carboxaldehyde in the presence of an acid catalyst, preferably p-toluenesulfonic acid to afford methyl 2-(3-pyridinyl)-4-dithiolanecarboxylate (16). The dithiolane ester is hydrolyzed to the corresponding acid (17) by treatment with aqueous base, preferably lithium hydroxide. 2-(3-Pyridinyl)-4-dithiolanecarboxylic acid (17) is then converted to an active ester (18), preferably the imidazolide (W is 1-imidazole) by treatment with carbonyl diimidazole. The anion of an unsubstituted or substituted indole (8) is prepared by treatment with a strong base, preferably sodium hydride, and this is reacted wire the active ester (18) to afford 1-[2-(3-pyridinyl)-dithiolan-4-oyl]indole (19).

Scheme VI

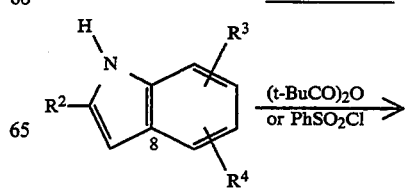

-continued
Scheme VI

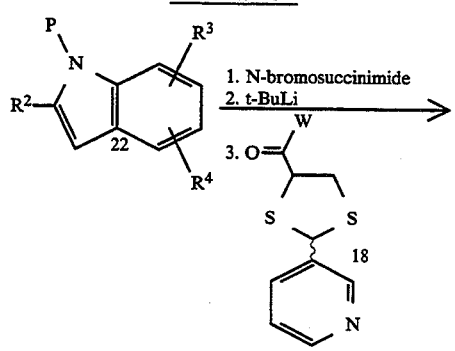

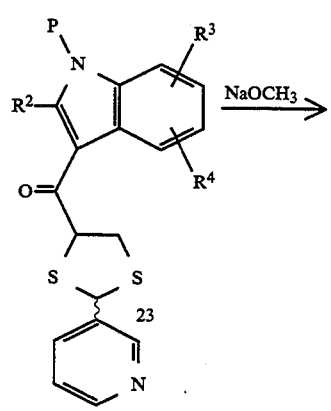

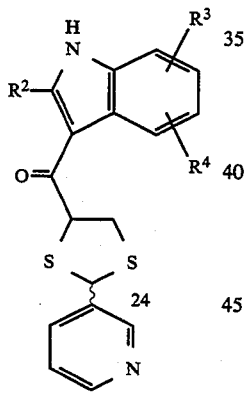

Scheme VII

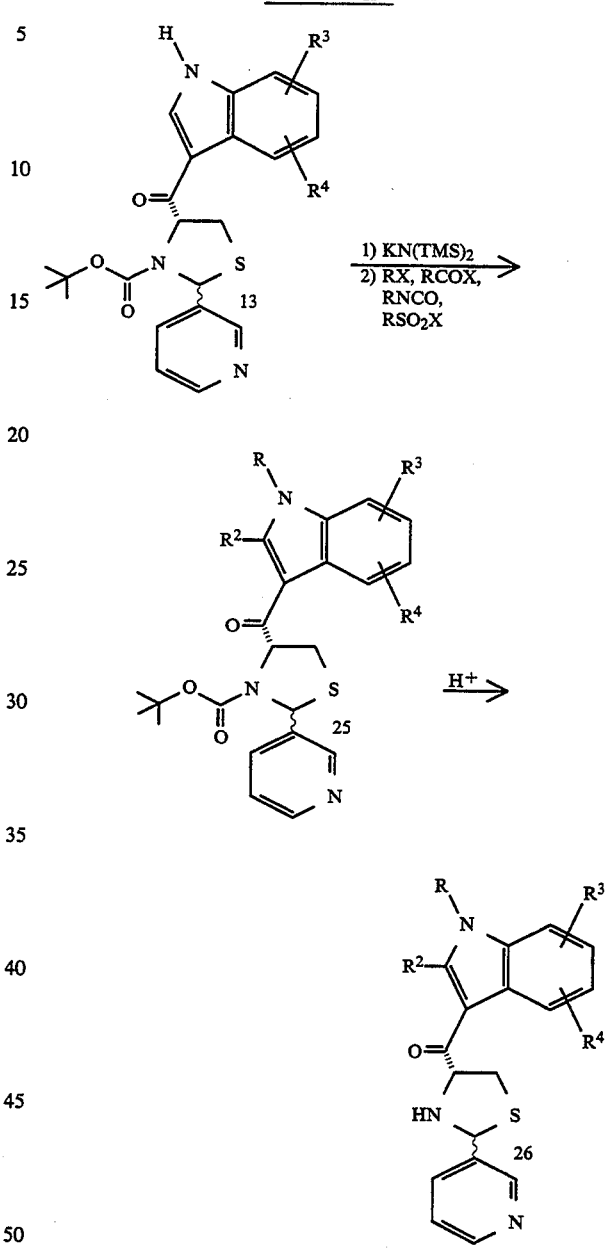

According to the foregoing reaction scheme VI, an indole without a nitrogen substituent is protected, preferably as the BOC from treating with di-tert-butyl dicarbonate (4) or as the benzenesulfonyl from treating with benzenesulfonyl chloride and a base, preferably KOH, to give 22. This protected indole is treated with a halogenating agent, preferably N-bromosuccinimide, then metallated with an organolithium reagent, preferably tert-butyl lithium, at −78° C., and then reacted with the active ester 18, preferably the N-methyl-N-methoxy amide (W is N(CH$_3$)OCH$_3$) to afford the 1-protected-3-[2-(3-pyridinyl)-dithiolan-4-oyl]indole (23). The BOC or benzenesulfonyl group can be removed by treatment with a nucleophile, preferably sodium methoxide, to afford 3-[2-(3-pyridinyl)-dithiolan-4-oyl]indole (24).

According to the foregoing reaction scheme VII, a 3-[2-(3-pyridinyl)-3-tert-butoxycarbonylthiazolid-4-oyl-]indole (13) without a substituent on the indole nitrogen is treated with a strong base, preferably potassium hexamethyl disilazide, followed by treatment with an alkyl halide (RX) or an active ester (RCOX), such as an acid chloride, an isocyanate (RNCO), or an alkylsulfonyl halide (RSO$_2$X) to give the indole with a substituent on the indole nitrogen (25). The BOC group is removed from 20 by treatment with an acid, preferably HCl to afford 26.

Scheme VIII

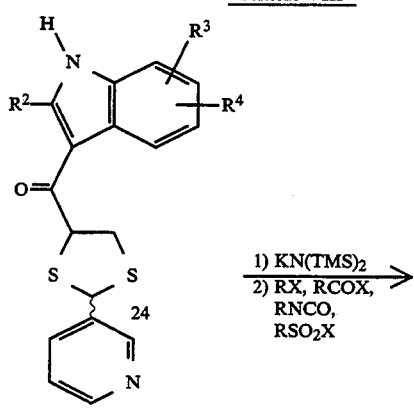

The foregoing reaction scheme VIII describes transformations similar to scheme VII, except using the dithiolane 24 instead of the thiazolidine 13 to a afford 3-[2-(3-pyridinyl)-dithiolan-4-oyl]indole with a substituted indole nitrogen (27).

Scheme IX

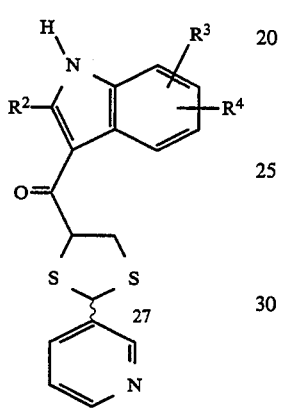

According to the foregoing reaction scheme IX, 3-[2-(3-pyridinyl)-thiazolid-4-oyl]indole with an unsubstituted indole nitrogen (12 X=NH) or 3-[2-(3-pyridinyl)-dithiolan-4-oyl]indole with an unsubstituted indole nitrogen (24, X=S) is treated with di-tert-butyl dicarbonate (4), preferably in the presence of an activating agent such as 4-dimethylamino pyridine, to afford the BOC substituted compound 28.

Scheme X

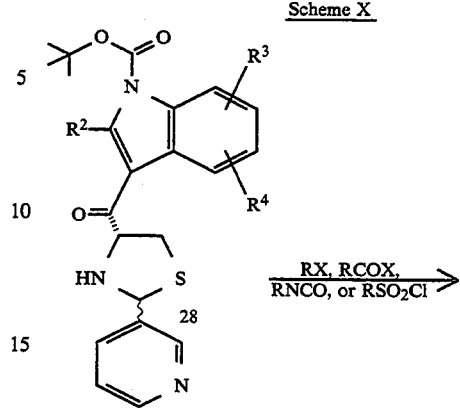

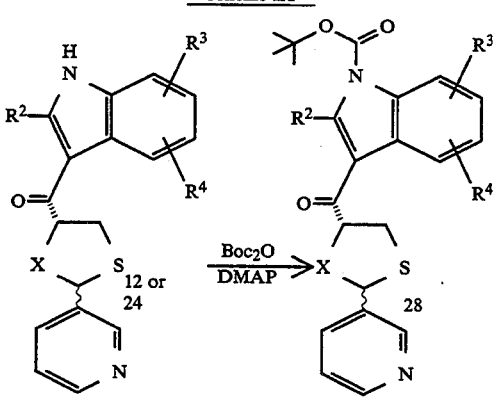

According to the foregoing reaction scheme X, 1-tert-butoxycarbonyl-3-[2-(3-pyridinyl)-thiazolid-4-oyl]indole (28) is treated with a alkyl halide (RX), an alkoyl halide (RCOX), an isocyanate or an alkyl sulfonyl halide to afford the substituted compound 29 in the presence of a base such as triethylamine. The BOC group can be removed by treating with an acid, preferably HCl, to yield the substituted 3-[2-(3-pyridinyl)-thiazolid-4-oyl]indole (30).

Scheme XI

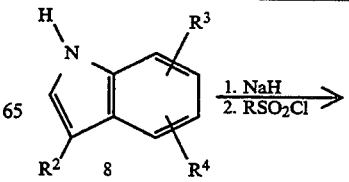

Scheme XI

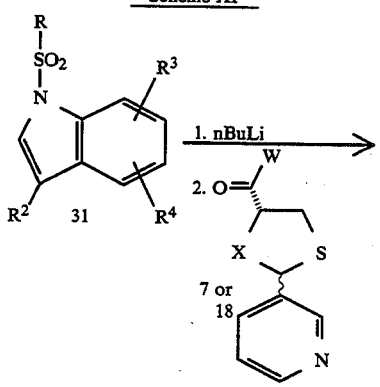

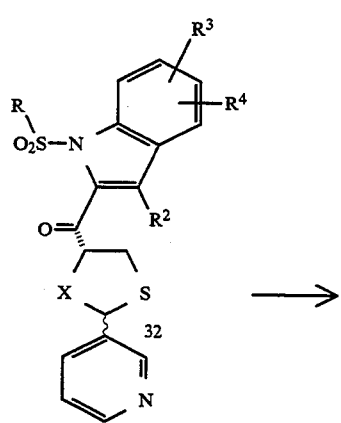

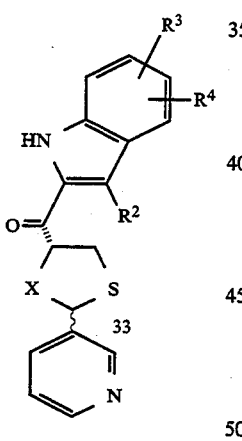

Scheme XII

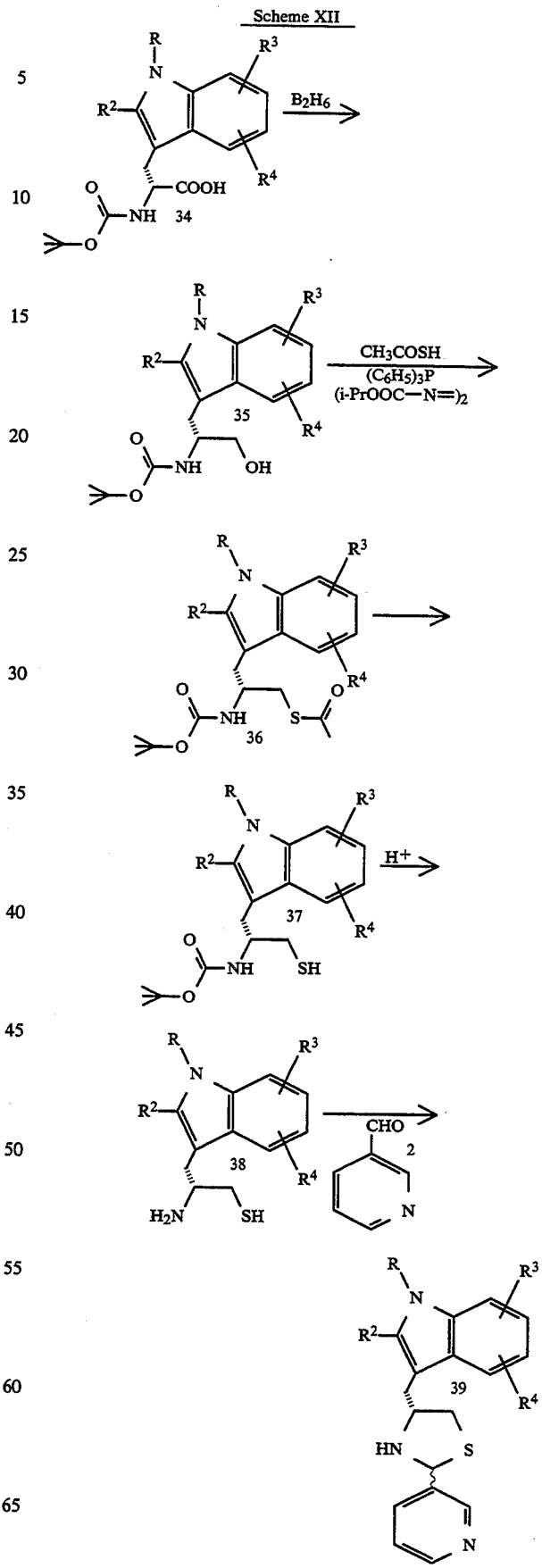

According to the foregoing reaction scheme XI, an unsubstituted or substituted indole is treated with a bee, preferably sodium hydride and then reacted with an aryl sulfonyl chloride (ArSO2Cl), preferably benzenesulfonyl chloride to yield the sulfonyl indole 31. This compound (31) is then treated with n-butyl lithium followed by an active ester of 2-(3-pyridinyl)-3-tert-butoxycarbonyl-4-thiazolidinecarboxylic acid (7, X is N—COtbutyl) or of 2-(3-pyridinyl)-4-dithiolanecarboxylic acid (18, X is S) to yield compound (32). The sulfonyl protecting group can be removed by hydrolysis in aqueous base, preferably lithium hydroxide to afford a 2-[2-(3-pyridinyl)-3-tert-butoxy-carbonyl-thiazolid-4-oyl]indole or a 2-[2-(3-pyridinyl)-dithiolan-4-oyl]indole (30)... In t former case, he BOC group can be removed by treating with an acid, preferably HCl to yield the 2-[2-(3-pyridinyl)-thiazolid-4-oyl ]indole.

According to the foregoing reaction scheme XII, an unsubstituted or substituted BOC-D-tryptophan is reduced, preferably with diborane to yield a tryptanol (35). This compound (35) is treated with thioacetic acid, triphenyl phosphine, and a dialkylazodicarboxylate, preferably di-isopropyl azodicarboxylate to yield the thio acetate, 36. The thio ester (36) is hydrolyzed with hydroxide, preferably sodium hydroxide in methanol to yield a thiol, 37, and then the BOC group is cleaved with acid, preferably HCl, to yield an amino thiol, 38. This compound (38) is condensed with 3-pyridine carboxaldehyde to give a 3-[2-(3-pyridinyl)-thiazolid-4-oyl]methylindole (39).

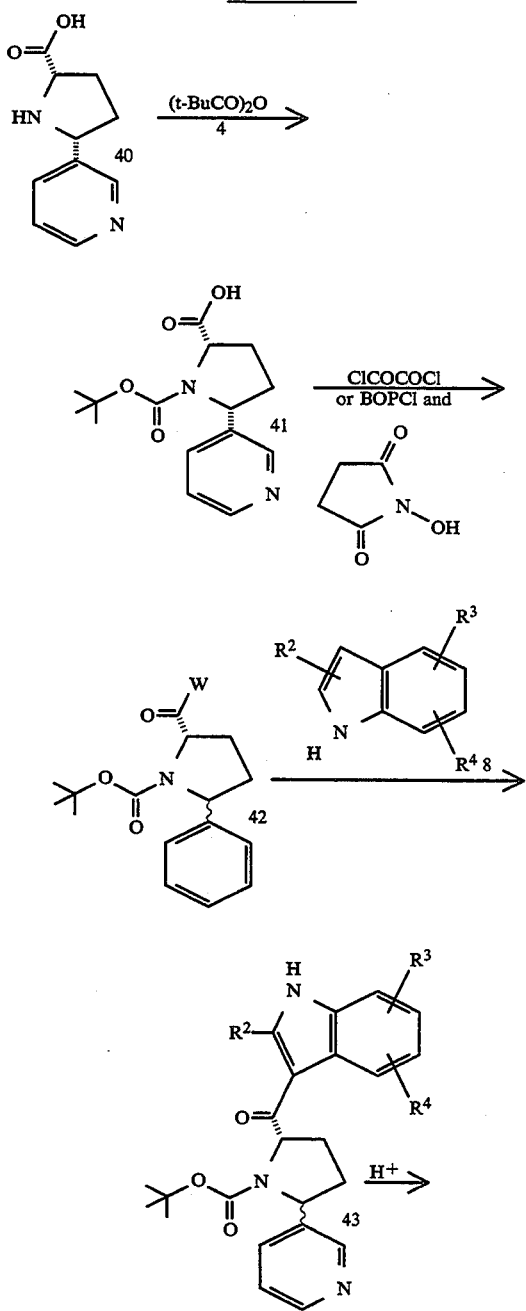

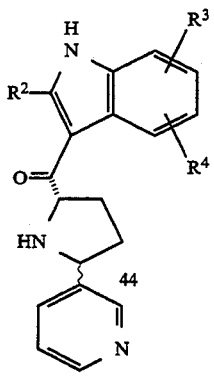

According to the foregoing reaction scheme XIII, 2-(3-pyridinyl)-5-pyrrolidinecarboxylic acid (40) is protected with an appropriate group, preferably carbotertbutoxy (BOC) with di-tert-butyl dicarbonate (4). The resulting 1-tert-butoxycarbonyl-2-(3-pyridinyl)-5-pyrrolidinecarboxylic acid (41) is converted to an active ester 7), preferably the acid chloride (W is Cl), through the action of oxalyl chloride, or the N-hydroxysuccinimide ester (W is O-succinimide) through the action of N-hydroxylsuccinimide and a coupling agent such as dicyclohexylcarbodiimide or bis (2-oxo-3-oxazolidinyl)-phosphinic chloride. The anion of an unsubstituted or substituted indole (8) is prepared by reacting the indole with a strong base, preferably ethyl magnesium bromide. The anion (8) is reacted with the active ester (42) to yield 3-[1-tert-butoxycarbonyl-2-(3-pyridinyl)-pyrrolindin-5-oyl]indole (43). The BOC group can be removed by treating 43 with an acid, preferably HCl to yield 3-[2-(3-pyridinyl)-pyrrolidin-5-oyl]indole (44).

PAF Inhibitory Activity of the Compounds of the Present Invention

The ability of representative compounds of the present invention to inhibit PAF activity was determined in an in vitro test using the following method.

Citrated whole rabbit blood was obtained from Pel-Freez (Rogers, AR). Rabbit platelets were prepared by centrifugation and washing. The platelets were lysed by freeze-thawing and sonication; platelet membranes were prepared by centrifugation and washing. Final membrane preparations were stored frozen in 10 mM Tris/5 mM $MgCl_2$/2 mM EDTA (TME buffer, pH 7.0) with 0.25M sucrose added for membrane stabilization.

The standard PAF receptor binding assay contained 10 μg platelet membrane protein, 0.6 nM [$^3$H]$C_{18}$-PAF (from Amersham or New England Nuclear; specific activity 120–180 Ci/mmol), with and without test compound, in "binding buffer" consisting of TME with 0.25% bovine serum albumin added (Sigma, RIA grade). The final volume of the assay was 100 μl. The assay was conducted in Millititre-GV ™ (Millipore Corp.) filtration plates; incubation time was for 60 minutes at room temperature (22°–23° C.). "Specific binding" was operationally defined as the arithmetic difference between "total binding" of 0.6 nM [$^3$H]$C_{18}$-PAF (in the abasence of added PAF) and "nonspecific binding" (in the presence of 1 μM PAF). After the prescribed incubation, platelet membranes were filtered under vacuum, and washed with 1 milliliter of "binding buffer". The filters were dried and removed. The bound radioactivity was quantitated with a Berthold TLC-Linear Analyzer model LB2842.

Dose-response curves of inhibition of specific [$^3$H]C$_{18}$-PAF binding by test compounds were conducted in triplicate, with at least four doses covering the active range. Experiments were repeated at least once. IC$_{50}$ values (concentration producing 50% inhibition) were determined by point-to-point evaluation. K$_i$ values of inhibitory binding constants were calculated according to the method of Cheng and Prusoff [Biochem. Pharmacol. 22 (1973) 3099–3108] whereby $$K_i = \frac{IC_{50}}{1 + ([{}^3H]PAF]/K_d[{}^3H]PAF)}$$
$$= \frac{IC_{50}}{1 + (0.6\ nM/0.6\ nM)}$$
$$= \frac{IC_{50}}{2}$$

The values of K$_i$ for representative compounds of the present invention appear in Table 1.

TABLE 1

| PAF Receptor Binding Activity | |
| --- | --- |
| Example | K$_i$ (nM) |
| 1 | 7 |
| 2 | 30 |
| 3 | 65 |
| 4 | 46 |
| 5 | 33 |
| 6 | 53 |
| 7 | 12 |
| 8 | 4 |
| 9 | 140 |
| 10 | 2100 |
| 11 | 15 |
| 12 | 15 |
| 13 | 2400 |
| 14 | 67 |
| 15 | 23 |
| 16 | 25 |
| 17 | 93 |
| 18 | 52 |
| 19 | 12,500 |
| 20 | 4 |
| 21 | 105 |
| 22 | 13 |
| 23 | 23 |
| 24 | 13 |
| 25 | 5 |
| 26 | 360 |
| 27 | 6 |
| 28 | 2 |
| 29 | 180 |
| 30 | 900 |
| 31 | 1700 |
| 32 | 1000 |
| 33 | 600 |
| 34 | 2 |
| 35 | 1 |
| 36 | 30 |
| 37 | 15 |
| 38 | 1 |
| 39 | 23 |
| 40 | 10 |
| 41 | 4 |
| 42 | 2 |
| 43 | 32 |
| 44 | 4 |
| 45 | 3 |
| 46 | 50 |
| 47 | 9 |
| 48 | 1 |
| 49 | 25 |
| 50 | 1 |
| 51 | 13 |
| 52 | 1 |

TABLE 1-continued

| PAF Receptor Binding Activity | |
| --- | --- |
| Example | K$_i$ (nM) |
| 53 | 1 |
| 54 | 9 |
| 55 | 2 |
| 56 | 150 |
| 57 | 10.000 |
| 58 | 540 |
| 59 | 20 |
| 60 | 2 |
| 61 | 8 |
| 62 | 18 |
| 63 | 13 |
| 64 | 88 |
| 65 | 9 |
| 66 | 31 |
| 67 | 39 |
| 68 | 36 |
| 69 | 13 |
| 70 | 2 |
| 71 | 2 |
| 72 | 10 |
| 73 | 8 |
| 74 | 3 |
| 75 | 2 |
| 76 | 30 |
| 77 | 9 |
| 78 | 2 |
| 79 | 16 |
| 80 | 3 |
| 81 | 2 |
| 82 | 9 |
| 83 | 16 |
| 84 | 9 |
| 85 | 4 |
| 86 | 15 |
| 87 | 4 |
| 88 | 150 |
| 89 | 1 |
| 90 | 270 |
| 91 | 37 |
| 92 | 150 |
| 93 | 35 |
| 94 | 33 |
| 95 | 3300 |
| 96 | 150 |
| 97 | 150 |
| 98 | 18,000 |
| 99 | 5000 |
| 100 | 5200 |
| 101 | 2200 |
| 102 | 2700 |
| 103 | 2800 |
| 104 | 650 |
| 105 | 175 |
| 106 | 80 |
| 107 | 75 |
| 108 | 250 |
| 109 | 70 |
| 110 | 1400 |
| 111 | 700 |
| 112 | 4800 |
| 113 | 1300 |
| 114 | 43 |
| 115 | 155 |
| 116 | 7 |
| 117 | 3 |
| 118 | 5 |
| 119 | 20 |
| 120 | 19 |
| 121 | 6 |
| 122 | 400 |
| 123 | 2 |

The foregoing may be better understood from the following Examples, which are presented for the purpose of illustration and not intended to limit the scope of the inventive concept.

EXAMPLE 1

Preparation of
1-[2-(3-pyridinyl)thiazolid-4-oyl]-5-phenylmethoxyindole.

Step 1. 2-(3-pyridinyl)-4-thiazolidinecarboxylic acid.

Cysteine (24.2 g, 0.2 mole) and 3-pyridine carboxaldehyde (21.4 g, 0.2 mol) were suspended in 60% aqueous ethanol (400 mL) and the mixture was heated at 100° C. for 5 hours. The reaction mixture was then cooled and most of the solvent was removed in vacuo. The resulting slurry was washed with ethanol and filtered. This material was dried overnight in vacuo at 50° C. to afford the thiazolidine acid (34 g, 81%).

Step 2. 2-(3-pyridinyl)-3-tert-butoxycarbonyl-4-thiazolidinecarboxylic acid.

To a slurry of 2-(3-pyridinyl)-4-thiazolidinecarboxylic acid (7.0 g, 33.3 mmol) as prepared in Step 1 in 40 mL dioxane was added 60 mL of 1M NaOH and di-tert-butyldicarbonate (1.5 eq, 50 mmol) in dioxane. The mixture was stirred for 19 hours. The mixture was concentrated and the resulting liquid partitioned between ethyl acetate and water. The aqueous phase was extracted with ethyl acetate and dried to yield 2-(3-pyridinyl)-3-tert-butoxycarbonyl-4-thiazolidinecarboxylic acid (8.27 g, 80%).

Step 3. 2-(3-pyridinyl)-3tert-butoxycarbonyl-4-thiazolidinecarboxylate N-hydroxysuccinimide ester.

2-(3-Pyridinyl)-3-tert-butoxycarbonyl-4-thiazolidinecarboxylic acid (20 g, 0.0644 mol), N-hydroxysuccinimide (8.14 g, 0.071 mol), and dimethylaminopyridine (787 mg, 0.0064 mol) were mixed and dimethylformamide (200 mL) added with stirring under $N_2$ atmosphere at room temperature. The flask was cooled and dicyclohexylcarbodiimide (13.2 g, 0.064 mol) added and the mixture stirred in an ice bath. The reaction mixture was then allowed to slowly warm to room temperature and stirred for 17 hours. The mixture was concentrated under high vacuum, the residue extracted with ethyl acetate, and filtered. The material was chromatographed on a silica column to yield 2-(3-pyridinyl)-3-tert-butoxycarbonyl-4-thiazolidinecarboxylate N-hydroxysuccinimide ester. (16.99 g, 65%).

Step 4. 1-[2,-(3-pyridinyl)-3-tert-butoxycarbonyl-4-thiazolid-4-oylmethyl]-5-phenylmethoxyindole.

Sodium hydride (60% dispersion, 147 mg, 0.00368 mol). tetrahydrofuran (3 mL), and dimethylsulfoxide (2 mL) were stirred under $N_2$ atmosphere and cooled in an ice bath. 5-Benzyloxyindole (822 mg, 0.00368 mol) in dimethylsulfoxide and tetrahydrofuran were added and the resulting suspension stirred at 0° C. until homogeneous and 2-(3-pyridinyl)-3-(tert-butoxycarbonyl)-4-thiazolidinecarboxylate N-hydroxysuccinimide ester (1.0 g, 0.00245 mol) added under $N_2$ atmosphere. The suspension was stirred at 0° C. for 15 min, then was allowed to warm to room temperature and was stirred for 17 hours. The reaction was quenched with 10% citric acid and the mixture diluted with ethyl acetate. The organic layer was washed and dried over magnesium sulfate and filtered. The filtrate was dissolved in dichloromethane and chromatographed on silica gel to yield 884 mg 1-[2-(3-pyridinyl)-3-(tert-butoxycarbonyl)-4-thiazid-4-oyl]-5-phenylmethoxyindole (70%).

Step 5. 1-[2-(3-pyridinyl)-thiazolid-4-oyl]-5-phenylmethoxyindole.

1-[2-(3-pyridinyl)-3-(tert-butoxycarbonyl)-4-thiazolid-4-oyl]-5-phenylmethoxyindole (300 mg, 0.00058 mol) was stirred with dioxane under $N_2$ atmosphere. Hydrochloric acid/dioxane (2.5 mL, 4$\underline{M}$, 0.01175 mol) was added and stirred at room temperature for 2 hours. The reaction mixture was concentrated in vacuo and azeotroped with toluene. The residue was suspended in ether and washed with sodium bicarbonate. The organic phase was dried over $MgSO_4$ and the solvent evaporated to yield 1-[2-(3-pyridinyl)-thiazo-4-oyl]-5-phenylmethoxyindole (243.5 mg, 86%).

NMR (CDCl$_3$, 300 MHz) δ3.08–3.19 (c, 1H), 3.23–3.33 (c, 1H), 3.47(dd, 0.5H, J=3, 10.5 Hz), 3.59 (dd, 0.5H, J=3, 10.5 Hz), 4.55–4.69 (c, 1H), 5.12 (s,2H), 5.70 (d, 0.5H, J=10.5 Hz), 6.01 (s, 0.5H), 6.61 (d, 0.5H, J=4.5 Hz), 6.68 (d, 0.5H, J=4.5 Hz), 7.05–7.15 (c, 2H), 7.28–7.51 (c, 7H), 7.87 (dt, 0.5H, J=7.5, 1.5 Hz), 8.48 (dd, 1H, J=4.5,9 Hz), 853 (dd, 0.5H, J=3, 1.5 Hz), Mass Spectrum (FAB): 416 (M+1)+.

EXAMPLE 2

Preparation of 1-[2(3-pyridinyl)thiazolid-4,oyl]indole dihydrochloride

Step 1. 1-[2-(3-pyridinyl)thiazolid-4-oyl]indole.

1-[2-(3-pyridinyl)thiazolid-4-oyl]indole was prepared as described as described in Example 1, except indole was used instead of 5-phenylmethoxyindole.

Step 2. 1-[2-(3-pyridinyl)thiazolid-4-oyl]indole dihydrochloride.

The material prepared as in step 1 was dissolved in ether and treated with excess 4N HCl in dioxane. 1-[2-(3-pyridinyl)thiazolid-4-oyl]indole dihydrochloride was isolated by filtration.

NMR (CDCl$_3$, 300 MHz): δ8.84 (m, 1H), 8.66 (m, 1H), 8.50 (bd, 0.05H,J=5.2 Hz), 8.48 (bd, 0.5H, J=4.8 Hz), 7.97 (d, 0.5H, J=8.1 Hz), 7.90 (d, 0.5H, J=7.7 Hz) 758 (m, 1H), 7.54 (d, 0.5H, J=3.6 Hz), 7.45 (d, 3.6 Hz), 7.45 (d, 0.5H, J=4.0 Hz), 7.35 (m, 3H), 6.76 (d, 0.5H, J=3.5 Hz), 6.70 (d, 0.5H, J=3.7 Hz), 6.03 (s, 0.5H), 5.72 (s, 0.5H), 4.67 (m, 1H), 3.62 (dd, 0.5H, J=6.9, 10.3 Hz), 3.49 (dd, 0.5H, J=6.9, 10.3 Hz), 3.49 (dd, 0.5H,J=6.9,10.6 Hz), 3.30 (m, 1H). Mass Spectrum (DCI/NH$_3$): 310 [(M+1)+, 100].

EXAMPLE 3

Preparation of 1-[2-(3-pyridinyl)thiazolid-4-oyl]indole oxalate

1-[2-(3-pyridinyl)thiazolid-4-oyl]indole, prepared as described in Example 2 above, was dissolved in ether and treated with excess oxalic acid in ether. The desired salt was isolated by filtration.

NMR (CDCl$_3$, 300 MHz): δ8.84 (m, 1H), 8.66 (m, 1H), 850 (bd, 0.5H, J=5.2 Hz), 8.48 (bd, 0.50H,J=4.8 Hz), 7.97 (d, 0.5H, J=8.1 Hz), 7.90 (d, 0.5H,J=7.7 Hz), 7.58 (m, 1), 7.54 (d, 0.5H, J=3.6 Hz), 7.45 (d, 0.5H,J=4.0 Hz), 735 (m, 3H), 6.76 (d, 0.5H, J=3.5 Hz), 6.70 (d, 0.5H, J=3.7 Hz), 6.03 (s, 0.5H), 5.72 (s, 0.5H), 4.67 (m, 1H),3.62 (dd, 0.5H, J=6.9, 10.3 Hz), 3.49 (dd, 0.5H, J=6.9, 10.6 Hz), 3.30 (m, 1H). Mass Spectrum (DCI/NH$_3$): 310 [(M+1)+, 100].

EXAMPLE 4

Preparation of
1-[2-(3-pyridinyl)thiazolid-4-oyl]-2,5-dimethylindole

1-[2-(3-pyridinyl)thiazolid-4-oyl]-2,5-dimethylindole was prepared using the method of Example 1, except 2,5-dimethylindole was used instead of 5-phenylmethoxyindole.

NMR (CDCl$_3$, 300 MHz): δ2.38 (s, 1–0.5H), 2.43 (s, 1–0.5H), 2.58 (s, 1–0.5H), 2.68 (s, 1–0.5H), 3.20–3.35 (c, 1H), 3.45–3.61 (c, 1H), 4.80 (t, 1H, J=7.5 Hz), 5.69 (s, 0.5H), 6.01 (s, 0.5H), 6.35 (s, 0.5H), 6.38 (s, 0.5H), 7.00 (d, 0.5H, J=9 Hz), 7.10 (d, 0.5H, J=9 Hz), 7.22–7.39 (c, 2H), 7.65 (d, 0.5H, J=9 Hz), 7.80 (d, 0.5H, J=9 Hz), 7.88 (dt, 0.5H, J=7.5, 1.5 Hz), 7.96 (dt, 0.5H, J=7.5, 1.5 Hz), 8.55 (dd, 0.5H, J=3H, 1.5 Hz), 8.61 (dd, 0.5H, J=3, 1.5 Hz), 8.79 (d, 0.5H, J=3 Hz), 8.83 (d, 0.5H, J=3 Hz). Mass Spectrum (DCI/NH$_3$): 338 (M+1)+.

EXAMPLE 5

Preparation of 1-[2-(3-pyridinyl)thiazolid-4-oyl]-4-chloroindole dihydrochloride 1-[2-(3-pyridinyl)thiazolid-4-oyl]-4-chloroindole was prepared using the method of Example 1, except 4-chloroindole was used instead of 5-phenylmethoxyindole. The dihydrochloride salt was prepared as described in Example 2.

NMR (CDCl$_3$, 300 MHz): δ3.30 (m), 3.45 (m), 3.60 (dd, 3H, J=10, 7 Hz), 4.60 (br s, 1H), 6.00 (br s, 1H), 5.80 (br s, 1H), 6.85 (d, 1H, J=3 Hz), 6.90 (d, 1H, J=3 Hz), 7.30 (m, 2H), 7.55 (d, 1H, J=3 Hz), 7.60 (d, 1H, J=3 Hz), 7.90 (d, 1H, J=3 Hz), 7.96 (m, 1H), 8.40 (dd, 1H), 8.60 (dd, 1H, J=5 Hz), 8.63 (d, 1H, J=6 Hz), 8.80 (m, 1H).

EXAMPLE 6

Preparation of 1-[2-(3-pyridinyl)thiazolid-4-oyl]-4-bromoindole dihydrochloride 1-[2-(3-pyridinyl)thiazolid-4-oyl]-4-bromoindole was prepared using the method of Example 1, except 4-bromoindole was used instead of 5-phenylmethoxyindole. The dihydrochloride salt was prepared as described in Example 2.

NMR (CDCl$_3$, 300 MHz): δ3.30 (m), 3.45 (m), 3.60 (dd, 3H, J=10, 7 Hz), 4.60 (br, s, 1H), 6.00 (br s, 1H), 5.80 (br s, 1H), 6.85 (d, 1H, J=3 Hz), 6.90 (1H, d, J=3 Hz), 7.30 (m, 2H), 7.55 (d, 1H, J=3 Hz), 7.60 (d, 1H, J=3 Hz), 7.90 (d, 1H, J=3 Hz), 7.96 (m, 1H), 8.4 (dd, 1H), 8.60 (dd, 1H, J=5 Hz), 8.63 (d, 1H, J=6 Hz), 8.80 (m, 1H).

EXAMPLE 7

Preparation of 1-[2-(3-pyridinyl)thiazolid-4-oyl]-4-benzoylindole dihydrochloride 1-[2-(3-pyridinyl)thiazolid-4-oyl]-4-benzoylindole was prepared using the method of Example 1, except 4-benzoylindole was used instead of 5-phenylmethoxyindole. The dihydrochloride salt was prepared as described in Example 2.

NMR (CDCl$_3$, 300 MHz): δ8.83 (m, 1H), 8.74 (m, 1H), 8.64 (m, 0.5H), 8.57 (m, 0.5H), 7.96 (m, 0.5H), 7.88 (m, 0.5H), 7.83 (m, 2H), 7.67 (d, 0.5H, J=3.7 Hz), 7.60 (m, 2.5H), 7.49 (m, 3H), 7.30 (m, 1H), 7.19 (d, 0.5H, J=4.4, Hz), 7.12 (d, 0.5H, J=3.7 Hz), 6.03 (m, 0.5H), 5.74 (m, 0.5H), 4.71 (m, 1H), 3.62 (dd, 0.5H, J=7.0, 10.4 Hz), 3.52 (dd, 0.5H, J=7.0, 10.6 Hz), 3.38 (m, 1H). Mass Spectrum (DCI/NH$_3$): 414 [(M+1)+, 30], 239 (70), 222 (95), 124 (100).

EXAMPLE 8

Preparation of 1-[2-(3-pyridinyl)thiazolid-4.0yl]-4-(3,4,5-trimethoxybenzoyl)-indole Step 1. 4-(3,4,5-trimethoxybenzoyl)indole.

The desired compound was prepared according to the method described in J. Org. Chem., 51:5106–5110 (1986) for synthesis of 4-formylindole, except substituting N-methoxy-N-methyl-3,4,5-trimethoxybenzamide for dimethylformamide.

Step 2. 1-[2-(3-pyridinyl)thiazolid-4-oyl]-4-(3,4,5,-trimethoxybenzoyl)indole

1-[2-(3-pyridinyl)thiazolid-4-oyl]-4-(3,4,5-trimethoxybenzoyl)indole was prepared using the method of Example 1, except using 4-(3,4,5-trimethoxybenzoyl)indole instead of 5-phenylmethoxyindole.

NMR (CDCl$_3$, 300 MHz): δδ 8.84 (bs, 0.5H), 8.81 (d, 0.5H, J=2.0 Hz), 8.74 (m, 1H), 8.62 (bd, 0.5H, J=3.3 Hz), 8.55 (bd, 0.5H, J=4.8 Hz), 7.92 (m, 1H), 7.68 (d, 0.5H, J=3.7 Hz), 7.64 (d, 0.5H, J=2.2 Hz), 7.60 (m, 1H), 7.47 (m, 1H), 7.36 (m, 1H), 736 (m,1H), 7.11 (m, 3H), 6.01 (s, 0.5H), 5.72 (s, 0.5H), 4.72 (m, 1H), 3.96 (bs, 3H), 3.87 (s, 3H), 3.86 (s, 3H), 3.78 (m, 0.5H), 3.63 (m, 0.5H), 3.51 (dd, 0.5H, J=7.4, 10.7 Hz), 3.35 (dd, 0.5H, 7.3, 8.2 Hz). Mass Spectrum (FAB): 504 (M+, 65), 195, 165 (100), 144.

EXAMPLE 9

Preparation of 1-[2-(3-pyridinyl)thiazolid-4-oyl]-5-chloroindole dihydrochloride 1-[2-(3-pyridinyl)thiazolid-4-oyl]-5-chloroindole was prepared using the method of Example 1, except 5-chloroindole was used instead of 5-phenylmethoxyindole. The dihydrochloride salt was prepared as described in Example 2.

NMR (CDCl$_3$, 300 MHz): δ3.25 (dd, 0.5H, J=10.5, 10.5H), 5.10 (t, 1H, J=6 Hz), 5.99 (s, 0.5H), 6.19 (s, 0.5H), 6.79 (d, 1H, J=3 Hz), 7.35 (dd,0.5H,J=9, 1.5 Hz), 7.41 (dd, 0.5H, J=9, 1.5 Hz), 7.73 (dd, 1H, J=6, 3 Hz), 7.90 (dd, 0.5H, 7.5, 3 Hz), 8.06 (dd, 0.5H, J=7.5, 3 Hz), 8.16 (d, 0.5H, J=3 Hz), 8.23 (d, 0.5H, J=3 Hz), 8.39 (d 1H, J=9 Hz), 8.57 (d, 0.5H, J=7.5 Hz), 8.70 (d, 0.5H, J=7.5 Hz), 8.78 (d, 0.5H, J=4.5 Hz), 8.86 (d, 0.5H, J=4.5 Hz), 8.93 (d, 0.5H, J=0.5 Hz), 9.01 (d, 0.5H, J=1. 5 Hz)

EXAMPLE 10

Preparation of 1-[2-(3-pyridinyl)thiazolid-4-oyl]-5-cyanoindole dihydrochloride 1-[2-(3-pyridinyl)thiazolid-4-oyl]-5-cyanoindole was prepared using the method of Example 1, except 5-cyanoindole was used instead of 5-phenylmethoxyindole.

NMR (CDCl$_3$, 300 MHz): δ3.23–3.29 (c, 1H), 3.32–3.49 (c, 1H), 5.07–5.15 (c, 1H), 5.95 (s, 0.5 H) 6.10 (s, 0.5H), 7.12 (t, 0.5H, J=9 Hz), 7.21 (t, 0.5H, J=9 Hz), 7.53–7.84 (c, 2H) 7.93–8.03 (c, 1H), 8.16 (d, 1H, J=6 Hz), 8.22–8.32 (c, 0.5H), 8.49 (d, 1H, J=9 Hz), 8.61–8.76 (c, 1H), 8.79–8.98 (c, 1H).

EXAMPLE 11

Preparation of
1-(2-(3-pyridinyl)thiazolid-4-oyl)-5-phenylmethoxyindole dihydrochloride 1-(2-(3-pyridinyl)thiazolid-4-oyl)-5-phenylmethoxyindole was prepared using the method of Example 1. The dihydrochloride salt was prepared as described in Example 2.

NMR (CDCl$_3$, 300 MHz): δ3.08–3.19 (c, 1H), 3.23–3.33 (c, 1H), 3.47 (dd, 0.5H, J=3, 10.5 Hz), 3.59 (dd, 0.5H, J=3, 10.5 Hz), 4.55–4.69 (c, 1H), 5.12 (s, 2H), 5.70 (d, 0.5H, J=10.5 Hz), 6.01 (s, 0.5H), 6.61 (d, 0.5H, J=4.5 Hz), 6.68 (d, 0.5H, J=4.5 Hz), 7.05–7.15 (c, 2H), 7.28–7.51 (c, 7H), 7.87 (d, 0.5H, J=7.5 Hz), 7.95 (dt, 0.5H, J=7.5, 1.5 Hz), 8.48 (dd, 1H, J=4.5, 9 Hz), 8.53 (dd, 0.5H, J=3, 1.5 Hz), 8.62 (dd, 0.5H, J=3, 1.5 Hz).

EXAMPLE 12

Preparation of
1-(2-(3-pyridinyl)thiazolid-4-oyl)-5-phenylmethoxyindole oxalate 1-(2-(3-pyridinyl)thiazolid-4-oyl)-5-phenylmethoxyindole was prepared using the method of Example 1. The salt was prepared as described in Example 3.

NMR (CDCl$_3$, 300 MHz): δ8.82 (m, 0.7H), 8.78 (m, 0.3H), 8.62 (m, 0.3H), 8.54 (m, 0.7H), 8.37 (m, 1H), 7.93 (m, 0.3H), 7.87 (m, 0.7H), 7.80 (d, 2H, J=8.1 Hz), 7.43 (m, 2H), 7.32 (m, 4H), 7.12 (m, 1H), 6.68 (d, 0.3H, J=2.8 Hz), 6.62 (d, 0.7H, J=2.9 Hz), 6.02 (b, 0.7H), 5.71 (b, 0.3H), 5.13 (s, 2H), 4.61 (m, 0.3H), 4.27 (m, 0.7H), 4.04 (m 0.7H), 3.78 (dd, 0.3H, J=5.2, 8.8 Hz), 3.48 (dd, 0.7H, J=3.3, 10.3 Hz), 3.27 (dd, 0.3H, J=3.3, 10.6 Hz). IR (CDCl$_3$): 3500, 3100, 2980, 2920, 1695, 1595, 1470, 1450, 1370, 1255, 1175. Mass Spectrum (DCI/NH$_3$): 416 [(M+1)+, 100], 304 (60), 287 (25).

EXAMPLE 13

Preparation of
1-[2-(3-pyridinyl)thiazolid-4-oyl]-5,6-dimethoxyindole dihydrochloride 1-[2-(3-pyridinyl)thiazolid-4-oyl]-5,6-dimethoxyindole was prepared using the method of Example 1, except 5,6-dimethoxyindole was used instead of 5-phenylmethoxyindole. The dihydrochloride salt was prepared as described in Example 2.

NMR (CDCl$_3$, 300 MHz): δ3.38 (bs, 1H), 3.75–3.90 (c, 7H), 5.78 (bs, 1H), 6.48 (bs, 2H), 6.83 (bs, 1H), 7.17 (d, 1H, J=7.5 Hz), 7.25 (d, 1H, J=7.5 Hz), 7.58–7.85 (c, 2H), 7.91–8.11 (c, 1H), 8.81–9.02 (c, 1H), 9.43–9.57 (c, 1H).

EXAMPLE 14

Preparation of
1-[2-(3-pyridinyl)thiazolid-4-oyl]-6-fluoroindole

1-[2-(3-pyridinyl)thiazolid-4-oyl]-6-fluoroindole was prepared using the method of Example 1, except 6-fluoroindole was used instead of 5-phenylmethoxyindole.

NMR (CDCl$_3$, 300 MHz): δ3.11 (bt, 0.5H, J=10.5 Hz), 3.26–3.37 (c, 1H), 3.49 (dd, 1H, J=10.5, 4.5 Hz), 3.61 (dd, 0.5H, J=10.5, 4.5 Hz), 4.58–4.71 (c, 1H), 5.71 (d, 0.5H, J=12 Hz), 6.01 (s, 0.5H), 6.67 (d, 0.5H, J=4.5 Hz), 6.73 (d, 0.5H, J=4.5 Hz), 7.04–7.13 (c, 1H), 7.39–7.49 (c, 1H), 7.42–7.55 (c, 2H), 7.85–7.91 (c, 0.5H), 7.93–7.99 (c, 0.5H), 8.20–8.30 (c. 1H), 8.53–8.57 (c, 0.5H), 8.62 (dd, 0.5H, J=3, 1.5 Hz), 8.82 (dd, 1H, J=10.5, 1.5 Hz). Mass Spectrum (DCI/NH$_3$): 328(M+), 165, 107.

EXAMPLE 15

Preparation of
1-[2-(3-pyridinyl)thiazolid-4-oyl]-6-chloroindole dihydrochloride 1-[2-(3-pyridinyl)thiazolid-4-oyl]-6-chloroindole was prepared using the method of Example 1, except 6-chloroindole was used instead of 5-phenylmethoxyindole. The dihydrochloride salt was prepared as described in Example 2.

NMR (CDCl$_3$, 300 MHz): δ3.60–3.20 (m, 2H), 3.80 (dd, 1H, J=14, 7 Hz), 5.40 (m, 1H), 5.60 (m, 1H), 6.18 (m, 1H), 6.40 (m, 1H), 6.90 (m, 1H), 7.30 (m, 2H), 7.65 (m, 1H), 8.40–8.60 (m, 2H). Mass Spectrum DCI/NH$_3$): 344(M+), 343,955.

EXAMPLE 16

Preparation of 1-[2-(3-pyridinyl)thiazolid-4-oyl]-6-bromoindole

1-[2-(3-pyridinyl)thiazolid-4-oyl]-6-bromoindole was prepared using the method of Example 1 except 6-bromoindole was used instead of 5-phenylmethoxyindole.

NMR (CDCl$_3$, 300 MHz): δ3.60–3.20 (m, 2H), 3.80 (dd, 1H, J=14, 7 Hz), 5.40 (m, 1H), 5.60 (m, 1H), 6.18 (m, 1H), 6.40 (m, 1H), 6.90 (m, 1H), 7.30 (m, 2H), 7.65 (m, 1H), 8.60–8.40 (m, 2H).

EXAMPLE 17

Preparation of 1-[2-(3-pyridinyl)thiazolid-4-oyl]-6-benzoylindole

1-[2-(3-pyridinyl)thiazolid-4-oyl]-6-benzoylindole was prepared using the method of Example 1 except 6-benzoylindole was used instead of 5-phenylmethoxyindole.

NMR (CDCl$_3$, 300 MHz): δ3.35 (m), 3.48 (dd), 3.60 (dd, 2H, J=10, 6 Hz), 4.65 (br m, 1H), 5.70 (d, 1H, J=10 Hz), 5.98 (br s, 1H), 6.80 (dd, 1H, J=6 Hz), 7.96–7.26 (m, 10H), 8.58 (dd, 1H, J=5, 2 Hz), 8.67 (d, 1H, J=3 Hz), 8.83 (d, 1H, J=2 Hz), 8.93 dd, 1H, J=1, 9 Hz).

EXAMPLE 18

Preparation of 1-(2-(3-pyridinyl)thiazolid-4-oyl)-6-phenylmethoxyindole oxalate 1-(2-(3-pyridinyl)thiazolid-4-oyl)-6-phenylmethoxyindole was prepared using the method of Example 1, except 6-phenylmethoxyindole was used instead of 5-phenylmethoxyindole. The oxalate salt was prepared as described in Example 3.

NMR (CDCl$_3$, 300 MHz): δ8 8.88 (d, 0.75 H, J=2.0 Hz), 8.81 (m, 0.25 H), 8.63 (m, 0.25H), 8.57 (dd, 0.75 H, J=0.5, 3.7 Hz), 8.21 (d, 0.75H, J=2.3 Hz), 8.18 (m, 0.25H), 7.95 (m, 1H), 7.35 (m, 7H), 7.04 (d, 1H, J=2.6 Hz), 7.01 (d, 1H, J=2.5 Hz), 6.68 (d, 0.25H), 6.63 (d, 0.75H, J=4 Hz), 6.04 (s, 0.75H), 5.71 (s, 0.25H), 5.16 (s, 1.5H), 5.14 (s, 0.5H), 4.66 (m, 0.75H), 3.64 (m, 0.25H), 3.48 (dd, 0.75H, J=6.9, 10.6 Hz), 3.29 (m, 0.25H), 3.27 (dd, 0.75H, J=7.3, 10.6 Hz). IR (KBr): 3450 (br), 3160, 2900, 1695, 1605, 1430, 1380, 1280, 1235, 1205, 905. Mass Spectrum (DCI/NH$_3$): 416[(M+1)+, 65], 369, 339, 291, 287, 267 (100), 225.

EXAMPLE 19

Preparation of 1-[2-(3-pyridinyl)thiazolid-4-oyl]-7-azaindole

1-[2-(3-pyridinyl)thiazolid-4-oyl]-7-azaindole was prepared using the method of Example 1, except 7-azaindole was used instead of 5-phenylmethoxyindole.

NMR (CDCl$_3$, 300 MHz): δ3.19-3.27 (c, 1H), 3.72-3.82 (c, 1H), 5.98-6.10 (c, 1), 6.22(s, 1H), 6.93 (d, 1H, J=4.5 Hz), 7.21 (dd, 1H, J=21, 9 Hz), 7.35-7.42 (c, 1H), 8.02-8.11 (c, 2H), 8.15 (d, 1H, J=7.5 Hz), 8.42 (d, 1H, J=4.5 Hz), 8.47 (t, 1H, J=4.5 Hz), 8.74 (d, 1H, J=4.5 Hz), 8.87 (d, 1H, J=4.5 Hz), 9.09 (d, 1H, J=9 Hz).

EXAMPLE 20

Preparation of 3-[2-(3-pyridinyl)thiazolid-4-oyl]indole oxalate

Step 1. 2-(3-pyridinyl)-3-tert-butoxycarbonyl-4-thiazolidinecarboxyl chloride 2-(3-Pyridinyl)-3-tert-butoxycarbonyl-4-thiazolidinecarboxylic acid, (2 g, 0064 mol) prepared as described in Example 1 step 2, was added to a suspension of sodium hydride (0.15 g, 0.0064 mol) in benzene (40 mL) and methylene chloride (10 mL). The mixture was stirred until gas evolution ceased and then oxalyl chloride (0.6 mL, 0.0064 mol) was added giving a cloudy brown solution of the desired material which was carried on without isolation.

Step 2. 3-(3-pyridinyl)-3-tert-butoxycarbonylthiazolid-4-oyl]indole

Indole (0.75 g, 0.0064 mol) in ether (20 mL) was added to ethylmagnesium chloride (3.2 mL. 2M in ether, 0.0064 mol). The mixture was allowed to stir for 20 minutes and was then added to a solution of 2-(3-pyridinyl)-3-tert-butoxycarbonyl-4-thiazolidinecarboxyl chloride prepared as described in step 1. The resulting mixture was stirred for 1 hour at ambient temperature and then the reaction was quenched with saturated ammonium chloride. The solvent was removed from the organic phase and the residue was redissolved in methylene chloride. This was washed with sodium bicarbonate, dried over sodium sulfate and concentrated to give a brown solid. The desired compound was obtained (0.44 g) following purification with 30% ethyl acetate in hexanes.

Step 3. 3-[2-(3pyridinyl)thiazolid-4-oyl]indole

3-[2-(3-pyridinyl)-3-tert-butoxycarbonylthiazolid-4-oyl]indole (34 mg, 0.08 mmol) was dissolved in dioxane/hydrochloride and stirred at ambient temperature. After 2 hours, the material was partitioned between ethyl acetate and sodium bicarbonate and then the organic phase was dried over magnesium sulfate and the solvent removed in vacuo to yield 3-[2-(3-pyridinyl)-thiazolid-4-oyl]indole (25 mg, 0.08 mmol).

NMR (CDCl$_3$, 300 MHz): δ 8.45 (m, 0.5 H), 8.80 (m, 0.5 H), 8.75 (b, 1H), 8.61 (m, 1H), 8.52 (m, 1H), 7.89 (m, 0.5H), 7.86 (m, 0.5H), 7.58 (m, 0.5H), 7.53 (d, 0.5H, J=4.1 Hz), 7.44 (m, 0.5 H), 7.39 (m, 0.5 H), 7.32 (m, 2H), 6.77 (d, 0.5H, J=4.1 Hz), 6.03 (b, 0.5H), 5.87 (b, 0.5H), 5.72 (b, 0.5H), 5.57 (b, 0.5H), 4.65 (m, 0.5H), 4.28 (m, 0.5H), 4.12 (m, 0.5H), 4.02 (m, 0.5H), 3.82 (m, 0.5H), 3.71 (m. 0.5H), 3.52 (m, 0.5H), 3.47 (m, 0.5H), 3.34 (m, 0.5H), 3.14 (m, 0.5 H). IR (CDCl$_3$): 3500, 3300, 2960, 2940, 1710, 1705, 1450, 1395, 1350, 1205, 805. Mass Spectrum (DCI/NH$_3$): 310[(M+1)+, 65], 267 (100),225(55),207 (30), 165.

EXAMPLE 21

Preparation of 1.2-dimethyl-3-[2-(3-pyridinyl)thiazolid-4-oyl]indole oxalate Aluminum chloride (2.9 g, 21.8 mmol) was added to a solution of 2-(3-pyridinyl)3-tert-butoxycarbonyl-4-thiazolidinecarboxyl chloride, prepared as described in Example 20, step 1 (from 1.33 g of acid). After 5 minutes, 1,2-dimethyl indole (0.74 g, 5. i mmol) was added in methylene chloride (5 mL). The mixture was stirred for 3 hours and then the reaction was quenched by the addition of saturated ammonium chloride solution (5 min). The mixture was partitioned between saturated sodium carbonate solution and methylene chloride. The organic phase was dried over MgSO$_4$ and the solvent evaporated in vacuo. The resulting residue was chromatographed on silica gel, eluting with 1:1 ethyl acetate/hexanes to afford the desired material. The oxalate salt was prepared as described in Example 3.

NMR (CDCl$_3$, 300 MHz): δ8.88 (m, 1H), 8.81 (d, 0.5H, J=2.2 Hz), 8.79 (d, 0.5H, J=2.2 Hz), 8.60 (dd, 0.5H, J=1.5, 4.8 Hz), 8.56 (dd, 0.5H, J=1.5, 4.8 Hz), 8.52 (m, 1H), 8.38 (m, 1H), 7.95 (m, 1H), 7.77 (m, 1H), 7.28 (m, 2H), 7.18 (d, 0.5H, J=1.5 Hz), 7.10 (d, 0.5H, J=3.6 Hz), 6.03 (s, 0.5H), 5.84 (s, 0.5H), 4.71 (m, 1H), 3.90 (s, 1.5), 3.86 (s, 1.5H), 3.53 (m, 0.5H), 3.41 (m, 0.5H), 3.22 (dd, 0.5H, J=1.1, 10.7 Hz), 3.14 (dd, 0.5H, J=2.2, 10.7 Hz). Mass Spectrum (DCI/NH$_3$): 324 [(M+1)+, 40], 296 (85), 190 (70), 107 (100).

EXAMPLE 22

Preparation of 1-methyl-3-[2-3-pyridinyl)thiazolid-4-oyl]indole dihydrochloride The desired material was prepared using the method of Example 21, except using 1-methylindole instead of 1,2-dimethylindole. The dihydrochloride salt was prepared as described in Example 2.

NMR (CDCl$_{13}$, 300 MHz): δ8.88 (m, 1H), 8.81 (d, 0.5H, J=2.Hz), 8.79 (d, 0.5H, J=2.2 Hz), 8.60 (dd, 0.5H, J=1.5, 4.8 Hz), 8.56 (dd, 0.5H, J=1.5, 4.8 Hz), 8.52 (m, 1H), 8.38 (m, 1H), 7.95 (m, 1H), 7.77 (m, 1H), 7.28 (m, 2H), 7.18 (d, 0.5H, J=1.5 Hz), 7.10 (d, 0.5H, J=3.6 Hz), 6.03 (s, 0.5H), 5.84 (s, 0.5H), 4.71 (m, 1H), 3.90 (s, 1.5H), 3.86 (s, 1.5H), 3.53 (m, 0.5H), 3.41 (m, 0.5H), 3.22 (dd, 0.5H, J=1.1, 10.7 Hz), 3.14 (dd, 0.5H, J=2.2, 10.7 Hz). Mass Spectrum (DCI/NH$_3$): 324 [(M+1)+, 40], 296 (85), 190 (70), 107 (100).

EXAMPLE 23

Preparation of 3-(2-(3-pyridinyl)thiazolid-4-oyl])-5-phenylmethoxyindole oxalate The desired compound was prepared according to the method of Example 20, except substituting 5-phenylmethoxyindole for indole. The oxalate salt was prepared as in Example 3.

NMR (CDCl$_3$, 300 MHz): δ8.84 (bs, 0.5H), 8.79 (d, 0.5H, J=2.2 Hz), 8.61 (dd, 0.5H, J=1.5, 4.8 Hz), 8.53 (dd, 0.5H, J=0.7, 4.8 Hz), 8.02 (m, 1H), 7.96 (d, 0.5H, J=2.9 Hz), 7.89 (d, 0.5H, J=3.3 Hz), 7.51 (bs, 0.5H), 7.48 (bs, 0.5H), 7.42 (d, 0.5H, J=1.4 Hz), 7.39 (d, 0.5H, J=1.5 Hz), 7.33 (m, 5H), 7.05 (m, 2H), 6.03 (s, 0.5H), 5.72 (bs, 0.5H), 5.16 (s, 2H), 4.69 (m, 0.5H), 4.58 (m, 0.5H), 3.52 (dd, 0.5H, J=7.3, 10.6 Hz), 3.38 (dd, 0.5H,

J=7.0, 10.3 Hz), 3.18 (m, 1H). IR (CDCl$_{13}$): 3440 (br), 3180, 3050, 2930, 2900, 1620, 1600, 1515, 1470, 1450, 1420, 1375, 1260, 1190, 800. 730, 705. Mass Spectrum (DCI/NH$_3$): 416 [(M+1)+, 90], 313 (85), 250 (100).

EXAMPLE 24

Preparation of
3-[2-(3-pyridinyl)thiazolid-4-oyl-4-phenylmethoxyindole oxalate

3-[2-(3-Pyridinyl)thiazolid-4-oyl ]-4-phenylmethoxyindole was prepared as described in Example 20, except 4-phenylmethoxyindole was used instead of indole. The oxalate salt was prepared as described in Example 3.

NMR (CDCl$_3$, 300 MHz): δ8.86 (m, 0.5H), 8.78 (m, 0.5H), 8.62 (m, 0.5H), 8.56 (m, 0.5H), 8.00 (m. 0.5H), 7.97 (m, 0.5H), 7.92 (m, 1H), 7.50–7.30 (m, 6H), 7.24 (m, 1H), 7.06 (m, 1H), 6.61 (dd, 0.5H, J=2.9, 6.8 Hz), 6.58 (dd, 0.5H, J=1.8, 6.5 Hz), 6.08 (bs, 0.5H), 5.86 (bs, 0.5H), 5.28 (s, 1H), 5.22 (s, 1H), 4.78 (m, 0.5H), 4.60 (m, 0.5H), 3.62 (m, 0.5H), 3.53 (m, 0.5H), 3.24 (m, 1H). Mass Spectrum (DCI/NH$_3$): 416 [(M+1)+, 86], 326 (95), 292 (60), 107 (100). Exact Mass: Theoretical: 416.143; Experimental: 416.142.

EXAMPLE 25

Preparation of
3-(2-(3-pyridinyl)thiazolid-4-oyl)-7-methylindole oxalate Step
1.1–12-(3-pyridinyl)thiazolid-4-oyl]imidazole Carbonyl diimidazole (0.724 g, 0.00447 mol) was added to a solution of 2-(3-pyridinyl)-3-tert-butoxycarbonyl-4-thiazolidinecarboxylic acid, prepared as described in Example 1, step 2 (1.32 g, 0.00426 mol) in methylene chloride (40 mL). After stirring the reaction mixture for 3 hours the solution was extracted with saturated sodium chloride and dried over magnesium sulfate. The solvent was removed in vacuo to afford 1.03 g of the desired product as a beige solid.

Step 2. 3-[2-(3-pyridinyl)thiazolid-4-oyl]7-methylindole oxalate

3-[2-(3-pyridinyl)thiazolid-4-oyl]-7-methylindole oxalate was prepared using the method of Example 20, except 7-methylindole was used instead of indole and 1-[2-(3-pyridinyl)thiazolid-4-oyl]-imidazole was used instead of2-(3-pyridinyl)-3-tert-butoxycarbonyl-4-thiazolidinecarbonyl chloride. The salt was prepared as described in Example 3.

NMR (CDCl$_3$, 300 MHz): δ4.72 (dd, 0.6H, J=5.2, 7.4 Hz), 4.61 (dd, 0.4H, J=5.2, 8.8 Hz), 3.71 (s, 3H), 3.63 (dd, 0.4H, J=5.2, 10.3 Hz), 3.52 (dd, 0.6H, J=5.2, 10.2 Hz), 3.34 (dd, 0.4H, J=8.8, 10.3 Hz), 3.17 (dd, 0.6H, J=7.4, 10.2 Hz), Exact Mass: Theoretical: 324.117; Experimental: 324.117.

EXAMPLE 26

Preparation of 1-[2-(3-pyridinyl)dithiolan-4-oyl]indole oxalate

Step 1Methyl 2,3-dimercaptopropenonate

To a flame dried 1 liter 3-neck flask 30 g (1.25 mol, 5.8 eq) of sodium spheres (rinsed with hexanes) were added. The flask was equipped with an addition funnel and a reflux condenser. Anhydrous methanol (400 mL) was added to the sodium metal via the addition funnel in a dropwise fashion. Once all the sodium was in solution (approximately 45 minutes), the reaction was cooled to 0° C. and saturated with gaseous H$_2$S for 1hour. During the course of the addition, excess H$_2$S was neutralized by bubbling the bleed line through a trap containing a 10% solution of aqueous sodium hydroxide. A solution of 50.0 g (0.22 mol, 1 eq.) 2,3-dibromopropionic acid dissolved in 100 ml of methanol was added to the reaction mixture via the addition funnel at a rapid drip rate. The solution was allowed to warm to room temperature and was stirred an additional 18 hours.

The reaction was then acidified to pH 2 by initial dropwise addition of 100 mL of saturated methanolic HCl (H$_2$S evolution observed) followed by bubbling gaseous HCl into the reaction mixture until the desired pH was obtained. At this point, a thick white precipitate was present. The solution was stirred for an additional 4 hours and then concentrated in vacuo. The resulting pasty residue was partitioned between 300 mL of water and 300 mL of ethyl ether. The aqueous phase was extracted with ethyl ether (2×) and the combined organic extracts washed once with brine and dried over magnesium sulfate. The drying agent was filtered off and the filtrate concentrated in vacuo to yield methyl-2,3-dimercaptopropenonate (28.5g, 86.5%) as a light yellow oil.

Step 2. Methyl 2-(3-pyridinyl),4-dithiolanecarboxylate

To a 3-neck round bottomed flask equipped with a Dean Stark trap and a constant rate addition funnel was added 7.05 g (65.7 retool, 1.0 eq.) of 3-pyridinecarboxaldehyde and 15.0 g (78.9 mmol, 1.2 eq.) p-toluenesulfonic acid in 350 mL of toluene, 25 ml of 2-butanol, and 15 ml 1-butanol. The solution was heated to reflux, whereupon 10.0 g (65.7 mmol, 1 eq.) of methyl 2,3-dimercaptopropenonate as prepared in step 1, above, in 30 mL toluene was added dropwise over ninety minutes to the refluxing reaction mixture via the addition funnel. The reaction was allowed to for 17 hours and then was cooled to room temperature and concentrated in vacuo. The residue was partitioned between saturated aqueous sodium bicarbonate and ethyl acetate (requires agitation for >30 min). The aqueous phase was extracted one more time with ethyl acetate. The combined organic extracts were then washed successively with saturated aqueous sodium bisulfite (×2), 1M aqueous sodium hydroxide (×2), and saturated aqueous brine (×1 ), dried over sodium sulfate, filtered and concentrated in vacuo to afford 18.57 g (117 % crude yield) of a brown oil. TLC showed predominantly desired material along with some 3-pyridine carboxaldehyde and a much less polar impurity. The oil was purified by flash chromatography (SiO$_2$, 80:20 hexanes:ethyl acetate ). Methyl 2-(3-pyridinyl)-4-dithiolanecarboxylate was isolated in fractions 85–195 as 8.03 g (50.6% yield) of orange oil.

NMR (CDCl$_3$, 300 MHz) δ3.45 (dd, 0.5H), 3.60 (dd, 0.5H), 3.65 (dd, 0.5H), 3.70 (dd 0.5H), 3.80 (s, 1.5H), 3.82 (s, 1.5H), 4.50 (t, 0.5H), 4.65 (t, 0.5H), 5.75 (s, 0.5H), 7.30 (dd, 1H), 7.95 (ddt, 1H), 8.50 (td, 1H), 8.70 (dd, 1H).

Step 3, 2-(3-pyridinyl)-4-dithiolanecarboxylic acid

Dithiolane ester (2 g, 8.3 mmol, 1 eq.), prepared as in step 2 above, was dissolved in a 3:1 (v/v) solution of tetrahydrofuran and H$_2$O and lithium hydroxide hydrate (432 mg, 10 mmol, 1.2 eq.) was added in one portion. The reaction immediately assumed an orange color. After 10 min, thin layer chromatography showed complete consumption of starting ester. The reaction was concentrated in vacuo to remove tetrahydrofuran and the resulting aqueous solution extracted with ether (2×) to remove any impurities. The aqueous phase was acidified to pH 4 with 1N aqueous HCl and concentrated in vacuo. The resulting oily residue was then ultrasonicated with tetrahydrofuran and ethanol and vacuum filtered. The filtrate was concentrated in vacuo and chased two times with toluene to afford 1.6 g (85% yield) of 2-(3-pyridinyl)-4-dithiolanecarboxylic acid as a as yellow solid.

Step 4. 1-[2-(3pyridinyl)dithiolan-4-oyl]imidazole

The desired compound was prepared according to the method of Example 25. step 1, except using 2-(3-pyridinyl)-4-dithiolanecarboxylic acid instead of 2-(3-pyridinyl)-3-tert-butoxycarbonyl-4-thiazolidinecarboxylic acid.

Step 5. 1-[2-(3-pyridinyl)dithiolan-4-oyl]indole

Indole (0.25 g, 0.0021 mol) was dissolved in ether (20 mL) and the mixture heated until it began to reflux. Ethyl magnesium bromide (1.0 mL, 2.0 mmol in ether, 0.002 mol) was added, followed 15 min later by 1-[2-(3-pyridinyl)dithiolan4-oyl]-imidazole, prepared as described in step 4 above, (0,267 g, 0.00096 mol) in methylene chloride (15 mL). After heating at reflux temperature for 5.5 hours, the mixture was partitioned between saturated ammonium chloride (50 mL) and methylene chloride. The organic phase was dried over MgSO4 and the solvent evaporated in vacuo. After purification by column chromatography the desired compound was obtained. The oxalte salt was prepared as described in Example 3.

NMR (CDCl$_3$, 300 MHz): $\delta$8 8.84 (dd, 0.5H, J=2.2, 4.5 Hz), 8.76 (dd, 0.5H, J=2.8, 4.5 Hz), 8.51 (m, 1H), 8.19 (t, 0.5H, J=1.6 Hz), 8.16 (t, 0.5H, J=2.2 Hz), 7.92 (m 1H), 7.62 (bd, 0.5H, J=6.0 Hz), 7.58 (m, 0.5H), 7.27 (m, 3H), 7.05 (m, 1H), 6.68 (dd, 0.5H, J=1.0, 2.9 Hz), 6.57 (dd, 0.5H, J=1.2, 3.0 Hz), 5.82 (s, 0.5H), 5.77(s, 0.5H), 4.64 (dd, 0.5H, J=5.5, 6.1Hz), 4.49 (dd, 0.5H, J=5.8, 6.1Hz), 4.08 (dd, 0.5H, J=5.8, 11.2 Hz), 4.02 (dd, 0.5H, J=2.5, 8.5 Hz), 3.56 (dd, 0.5H, J=6.0, 9.1 Hz), 3.42 (dd, 0.5H, J=3.0, 10.5 Hz). Mass Spectrum (DCI/NH$_3$): 344 [(M+NH$_4$)+, 5],327 [(M+1)+, 50], 242 (30), 124 (55), 108 (100).

EXAMPLE 27

Preparation 9f
1-ethyl-3-[2-(3-pyridinyl)thiazolid-4-oyl]indole oxalate

Step 1, 1-Ethyl-3-2-(3-pyridinyl)-3-tert-butoxycarbonylthiazolid-4-oyl] indole

Potassium hexamethyldisilazide (1.2 mL, 0.5M in toluene, 0.0006 mol) was added to a solution of 3-[2-(3-pyridinyl)-3-tert-butoxycarbonylthiazolid-4-oyl]indole prepared as described in Example 20 in tetrahydrofuran (10 mL) at −78° C. The mixture was stirred for 20 minutes and then ethyl iodide (0.25 mL, 0.00031 mob was added. After an additional 50 rain of stirring the reaction mixture was allowed to warm to room temperature. Sixty min. later the solvent was removed and the residue partitioned between saturated aqueous NH$_4$Cl solution and ether. The organic phase was dried over MgSO$_4$. The solvent was removed in vacuo to give the desired material which was carried on without further purification.

Step 2. 1-Ethyl-3-[2-(3-pyridinyl)thiazolid-4-oyl]indole oxalate

1-Ethyl-3-[2-(3-pyridinyl)-3-tert-butoxycarbonylthiazolid-4-oyl]indole was deprotected with HCl in dioxane to give 1-Ethyl-3-[2-(3-pyridinyl)thiazolid-4-oyl]indole oxalate. The oxalate salt was prepared using the procedure described in Example 3.

NMR (CDCl$_3$, 300 MHz): $\delta$8.88 (m, 0.4H), 8.79 (d, 0.6H, J=1.2 Hz), 8.60 (dd, 0.6H, J=1.2, 4.8 Hz), 8.55 (m, 0.4H), 8.39 (m, 1H), 7.99 (m, 0.6H), 7.95 (m, 0.4H), 7.93 (s, 0.6H), 7.85 (s, 0.4H), 7.41 (m, 1H), 7.35 (m, 4H), 6.06 (s, 0.4H), 5.74 (s, 0.6H), 4.70 (dd, 0.6H, J=7.0, 9.8 Hz), 4.58 (dd, 0.4H, J=8.4, 9.6 Hz), 4.28 (q, 0.6H, J=7.3 Hz), 4.24 (q, 0.4H, J=7.3 Hz), 3.54 (dd, 0.6H, J=6.9, 10.3 Hz), 3.42 (dd, 0.4H, J=9.6, 16.6 Hz), 3.21 (dd, 0.6H, J=9.8, 10.3 Hz), 3.12 (dd, 0.4H, J=8.4, 10.3 Hz), 1.59 (t, 0.6H, J=7.0 Hz), 1.55 (t, 0.4H, J=7.3 Hz). IR (CDCl$_3$): 3680, 2960, 2920, 1705, 1635, 1520, 1390, 1130. Mass Spectrum (DCI/NH$_3$): 338 [(M+1)+, 100], 235 (20), 216 (40), 146 (45), 107 (100) Exact Mass: Theoretical: 338.132; Experimental: 338.132.

EXAMPLE 28 preparation of
1-tert-butoxycarbonyl-3-[2-(3-pyridinyl)thiazolid-4-oyl-]indole oxalate Di-tert-butyl dicarbonate (0.15 g, 0.00069 mol) was added to a solution of 3-[2(3-pyridinyl)-3thiazolid-4-oyl-]indole prepared as described in Example 20 (0.2 g, 0.65 mL) and the mixture was stirred for 1 hour. The mixture was then partitioned between saturated aqueous NH$_4$Cl and ethyl acetate. The organic phase was washed with saturated aqueous NaHCO$_3$ solution and dried over magnesium sulfate. The oxalate salt was prepared as described in Example 3.

NMR (CDCl$_3$, $_{300}$ MHz): $\delta$8.52 (dd, 0.5H, J=1.5, 4.8 Hz), 8.45 (dd, 0.5H, J=1.5, 4.8 Hz), 8.34 (s, 0.5H), 8.32 (sa, 0.5H), 8.18 (m, 0.5H), 8.15 (m, 0b.5H), 8.11 (m, 0.5H), 8.07 (m, 0.5H), 7.46–7.38 (m, 3H), 7.37 (d, 0.5H, J=1.5 Hz), 7.34 (d, 0.5H, J=1.0 Hz), 5.90 (bs, 0.5H), 5.75 (bs, 0.5H), 4.93 (m, 1H), 3.60 (dd, 0.5H, J=7.3, 10.3 Hz), 3.49 (dd, 0.5H, J=7.4, 10.3 Hz), 3.24 (m, 1H), 1.73 (s, 4.5H), 1.70 (s, 4.5H). IR (CDCl$_3$): 2980, 2920, 1735, 1660, 1445, 1370, 1235, 1045. Mass Spectrum (DCI/NH$_3$): 410 [(M+1)+, 100 ], 376 (10), 310 (10).

EXAMPLE 29

Preparation of
cis-1-tert-butoxycarbonyl-3-[2-(3-pyridinyl)dithiolan-4-oyl]indole hydrochloride Step 1. N-methoxy-N-methyl-2-(3-pyridinyl)-4-dithiolanecarboxamide N-methoxy-N-methyl amine (1.82 g, 0.018 mol) was added to a solution of 2-(3-pyridinyl)-4-dithiolanecarboxylic acid, reared as described in Example 25 (2.97 g, 13.1 mol), dimethylaminopyridine (94 mg, 0.0008 mol), and N-methylmorpholine (4.5 mL, 0.0041 mol) in Dimethylformamide (15 mL) and methylene chloride (150 mL). Bis(2-oxo-3-oxazolidinyl)phosphinic chloride (5.0 g, 0.0197 mol) was then added and the clear solution stirred for 17 hours. The reaction mixture was partitioned between saturated aqueous NaHCO$_3$ (200 mL) and methylene chloride (400 mL). The organic phase was washed with brine and dried over MgSO$_4$. The solvent was removed in vacuo and the residue chromatographed on silica gel eluting with 2:1 ethylacetate/hexanes to obtain the desired compound (2.21 g, 62% ).

Step 2.1 -tert-butoxycarbonyl-3-[2-(3-pyridinyl)dithiolan-4-oyl]indole oxalate tert-Butyl lithium (19.4 mL, 1.7M, 0.033 mol) was added to a solution of 1-tert-butoxycarbonyl-3-bromo indole (4.96 g, 0.016 mol) in ether (170 mL) at −78° C. Twelve min later N-methoxy-N-methyl-2-(3-pyridinyl)-

4-dithiolanecarboxamide (1.45 g, 0.0054 mol) in ether (20 mL) was added. The suspension was stirred at −78° C. for 1 hour and then allowed to warm to room temperature. The mixture was partitioned between ether (350 mL) and saturated aqueous ammonium chloride solution (350 mL). The organic phase was extracted with 200 mL of ethyl acetate and the combined organic phases were dried over MgSO$_4$. The solvent was removed in vacuo and the residue chromatographed on silica gel to give the desired product as a tan solid (1.14 g, 50%). The oxalate salt was prepared as described in Example 3.

NMR (CDCl$_3$, 300 MHz): δ8.67 (d, 1H, J=1.5 Hz), 8.50 (dd, 1H, J=1.5,48 Hz), 8.41 (m, 1H), 8.31 (s, 1H), 8.12 (m, 1H), 8.03 (m, 1H), 7.41 (m, 2H), 7.32 (d, 1H, J=4.8 Hz), 5.75 (s, 1H), 5.15 (~t, 1H, J=6.0 Hz), 4.03 (dd, 1H, J=6.2, 12.1 Hz), 3.49 (dd, J=5.8, 12.2 Hz), 1.72 (s, 9H).

EXAMPLE 30

Preparation of trans 1-tert-butoxycarbonyl-3-[2-(3-pyridinyl)dithiolan-4-oyl-]indole oxalate.

The desired compound was obtained along with the cis isomer from the sequence described in Example 29. It was isolated from mixed fractions obtained during the s chromatographic purification described in Example 29, step 2. The desired compound was purified by high pressure liquid chromatography on silica gel eluting with 2:1 ethyl acetate: / hexanes. The oxalate salt was prepared as described in Example 3.

NMR (CDCl$_3$, 300 MHz): δ8.78 (d, 1H, J=1.6 Hz), 8.55 (dd, 1H, J=16, 4.9 Hz), 8.39 (m, 1H), 8.30 (s, 1H), 8.12 (m, 1H), 7.98 (m, 1H), 7.41 (m, 2H), 7.29 (d, 1H, J=5.1 Hz), 5.77 (s, 1H), 5.32 (~t, 1H, J=5.9 Hz), 3.96 (dd, 1H, J=5.9, 12.0 Hz), 3.60 (dd, 1H, J=5.9 11.8 Hz), 1.71 (s, 9H).

EXAMPLE 31

Preparation of 3-2-(3-pyridinyl)dithiolan-4-oyl]indole oxalate

Sodium methoxide in methanol (0.75 mL, 2.0 M, 1.5 mmol) was added to a as solution of 1-tert-butoxycarbonyl-3-[2-(3-pyridinyl)dithiolan-4oyl]indole oxalate (0.2 g, 0.49 mmol) in tetrahydrofuran. After ten min. the reaction mixture was partitioned between brine (20 mL) and ethyl acetate (60 mL). The organic phase was dried over magnesium sulfate and the solvent evaporated. The residue was chromatographed on silica gel, eluting with 2:1 ethyl acetate/hexanes to give the desired compound. The oxalate salt was prepared as described in Example 3.

NMR (CDCl$_3$, 300 MHz): δ8.69 (d, 0.5H, J=1.9 Hz), 8.66 (d, 0.5H, J=1.8 Hz), 8.43 (dd, 0.5H, J=1.5, 9.6 Hz), 8.38 (dd, 0.5H, J=1.5, 4.8 Hz), 8.28 (m, 1H), 8.20 (s, 0.5H), 8.18 (s, 0.5H), 8.08 (t, 0.5H, J=2.1 Hz), 8.05 (m, 0.5H), 7.45 (m, 1H), 7.34 (m, 2H), 7.24 (m, 2H), 5.82 (s, 0.5H), 5.81 (s, 0.5H), 5.54 (t, 0.5H, J=5.9 Hz), 5.36 (dd, 0.5H, J=5.9, 7.0 Hz), 3.87 (dd, 0.5H, J=7.3, 12.2 Hz), 3.83 (dd, 0.5H, J=5.9, 12.1 Hz), 3.64 (dd, 0.5H, J=5.8, 11.8 Hz), 3.38 (dd, 0.5H, J=5.6, 12.2 Hz). Mass Spectrum (DCI/NH$_3$): 327 [(M+1)$^+$, 5], 124 (100).

EXAMPLE 32

Preparation 1-phenylsulfonyl 3-[2-(3-pyridinyl)dithiolan-4-oyl]indole oxalate

The desired compound was prepared according to the procedure of Example 29, except using 3-bromo-1-phenylsulfonyl indole instead of 3-bromo-1-tert-butoxycarbonyl indole.

NMR (CDCl$_3$, 3130 MHz): δ8.76 (d, 0.6H, J=2.2 Hz), 8.68 (d, 0.4H, J=2.3 Hz), 8.57 (dd, 0.6H, J=1.5, 4.8 Hz), 8.51 (dd, 0.4H, J=1.8, 5.1 Hz), 8.36 (m, 1H), 8.31 (s, 0.4H), 8.29 (s, 0.6H), 8.02 (m, 1H), 7.96 (m, 2H), 7.60 (m, 1H), 7.50 (m, 2H), 7.40 (m, 3H), 7.36 (m, 1H), 5.78 (s, 0.4H), 5.72 (s, 0.6H), 5.32 (t, 0.6H, J=5.9 Hz), 5.15 (t, 0.4H, J=5.9 Hz), 4.01 (dd, 0.4H, J=6.2, 12.5 Hz), 3.95 (dd, 0.6H, J=5.5, 11.8 Hz), 3.65 (dd, 0.6H, J=6.3, 12.2 Hz), 3.49 (dd, 0.4H, J=5.9, 12.5 Hz). IR (CDCl$_3$): 3120, 3050, 2980, 2940, 1670, 1535, 1445, 1380, 1190, 1180, 1140. Mass Spectrum (DCI/NH$_3$): 467 [(M+1)$^+$, 100], 312 (50), 172 (75).

EXAMPLE 33

Preparation of 3-[2-(3-pyridinyl)thiazolid-4-ylmethyl]indole dihydrochloride

Step 1. 1-Indol-3-yl-2-tert-butoxycarbonylamino-3-hydroxy propane

Borane-tetrahydrofuran (165 mL, 1M in THF, 0.165 mol) was added to a solution of BOC-D-tryptophan (10 g, 0.033 mol) in THF (250 mL) at 0° C. The reaction mixture was stirred for 17 hours and then quenched with methanol (50 mL). The mixture was poured into water (200 mL) and the organic layer separated, dried over sodium sulfate and the solvent removed in vacuo. The resulting residue was purified by chromatography on silica gel eluting with 1:1 ethyl acetate/hexanes to yield 5.13 g (54%) of the desired product.

Step 2. 1-Indol-3-yl-2,tert-butoxycarbonylamino-3-thioacetoxy propane

Di-isopropyl azodicarboxylate (3.48 mL, 0.017 mol) was added to a solution of triphenyl phosphine (4.63 g, 0.017 mol) in THF (75 mL). The mixture was stirred at 0° C. for 30 min and then a solution of 1-indol-3-yl-2-tert-butoxycarbonylamino-3-hydroxy propane, prepared as described above in step 1 (5.1 g, (0.017 mol) and thioacetic acid (1.26 mL, 0.176 mmol) in THF was added. The reaction mixture was stirred for 17 hours and then the solvent was remove in vacuo. The residue was purified by chromatography on silica gel eluting with 2:1 ethyl acetate/hexanes to yield 4.97 g of the desired product.

Step 3. 1-Indol-3-yl-2-amino-3-mercaptopropane

A mixture of 1 -indol-3-yl-1-2-tert-butoxycarbonylamino-3-thioacetoxy propane (3.0 g, 0.0086 mol) in methanol (20 mL) was heated at 60° C. for 30 min. The mixture was poured into saturated aqueous citric acid (200 mL) and then extracted with methylene chloride. The organic phase was dried over sodium sulfate and the solvent evaporated in vacuo. The residue was dissolved in acetic acid (10 mL) and HCl in acetic acid (10 mL) was added. The mixture was allowed to stand at room temperature for 45 min and the desired material precipitated with the addition of 200 mL of ether. The precipitate was collected by filtration and partitioned between saturated sodium bicarbonate solution and methylene chloride. The organic phase was separated, dried over sodium sulfate and the solvent evaporated to give 650 mg of the desired compound as a gray oil. This was carried on to the next step without further purification.

Step 4. 3-[2-(3-pyridinyl)thiazolid-4-ylmethyl]indole

3-Pyridinecarboxaldehyde (0.30 mL, 0.0032 mol) was added to a solution of 1-indole-3-yl-2-amino-3mercaptopropane (650 mg) in ethanol (10 mL) and the mixture stirred overnight. The solvent was removed in vacuo and the residue chromatographed on silica gel eluting with 2:1 ethyl acetate/hexanes to the desired compound.

Step 5. 3-[2-(3-pyridinyl)thiazolid-4-ylmethyl]indole dihydrochloride

Saturated HCl in ether (10 mL) was added to a solution of 3-[2-(3-pyridinyl)dithiolan-4-ylmethyl]indole in ethyl acetate (5 mL). The resulting solid was collected by filtration and dried in vacuo to provide the desired compound (187 mg) as a crystalline solid.

NMR (CDCl$_3$, 300 MHz): $\delta$2.87 (c, 1H), 3.20 (c, 3H), 3.73 (m, 1H), 5.60 (s, 0.67H), 5.77 (s, 0.33H), 7.10–7.30 (m, 3H), 7.38–7.52 (m, 1H), 7.62–7.90 (m, 2H), 8.19–8.21 (m, 1H), 8.50–8.80 (m, 2H), 8.82–9.08 (m, 1H), 10.13 (s,1H). Mass Spectrum (DCI/NH$_3$): 296 (M+1)$^{30}$.

EXAMPLE 34

Preparation of 6-phenylmethoxy-3-[2-(3-pyridinyl)thiazolid-4-oyl]indole

The desired material was prepared using the method of Example 20, except using 6-phenylmethoxy indole instead of indole and methyl magnesium bromide instead of ethyl magnesium bromide.

Melting Point: 193–195° C. NMR (CDCl$_3$, 300 MHz): $\delta$8.85 (d, 0.4H, J=1.2 Hz), 8.79 (d, 0.6H, J=1.4 Hz), 8.60 (m, 0.6H), 8.52 (m. 0.4H), 8.28 (s, 0.6H), 8.26 (s, 0.4H), 7.97 (m, 0.6H), 7.91 (d, 0.6H, J=7.8 Hz), 7.88 (m, 0.4H), 7.83 (d, 0.4H, J=7.6 Hz), 7.40 (m, 6H), 7.08 (m, 1H), 6.98 (d, 0.6H, J=2.2 Hz), 6.95 (d, 0.4H, J=2.3 Hz), 6.03 (s, 0.4H), 5.72 (s, 0.4H), 5.72 (s, 0.6H), 5.14 (s, 2H), 4.70 (dd, 0.6H, J=7.0, 7.7 Hz), 4.57 (dd, 0.4H, J=7.0 7.2 Hz), 3.52 (dd, 0.6H, J=7.0, 10.3 Hz), 3.38 (dd, 0.4H, J=7.0, 9.2 Hz), 3.18 (m, 1H). IR (KBr): 3420, 3250, 2920, 1630, 1525, 1420, 1175. Mass Spectrum (DCI/NH$_3$): 416 [(M+1)$^+$, 35], 185 (100). Elemental Analysis: Theoretical: C: 69.38,H: 5.09,N: 10.11; Found: C: 69.23, H: 5.15, N: 9.92.

EXAMPLE 35

Preparation of 1-tert-butoxycarbonyl-6-phenylmethoxy-3-[2-(3-pyridinyl)thiazolid-4-oyl]indole oxalate The desired compound was prepared using the procedure of Example 28, except using 6-phenylmethoxy-3-[2-(3-pyridinyl)thiazolid-4-oyl]indole prepared as described in Example 33, instead of 3-[2-(3-pyridinyl)-thiazolid-4-oyl]indole. The oxalate salt was prepared as described in Example 3.

NMR (CDCl$_3$, 300 MHz): $\delta$8.83 (d, 0.2H), 8.79 (d, 0.8H, J=1.9 Hz), 8.62 (dd, 0.8H, J=1.8, 5.1 Hz), 8.55 (dd, 0.2H), 8.26 (s, 0.8H), 8.23 (s, 0.2H), 7.97 (ddd, 0.8H, J=1.9,2.3, 7.8 Hz), 7.88 (m, 0.2H), 7.80(d, 1H, J=2.3 Hz), 7.41 (m, 7H), 7.10(dd, 1H, J=2.2, 8.8 Hz), 6.03 (s, 0.2H), 5.73 (s, 0.8H), 5.15 (s, 2H), 4.70 (dd, 0.5H, J=7.3, 9.1 Hz), 4.64 (m, 0.2H), 3.56 (dd, 0.8H, J=7.3, 10.3 Hz), 3.44 (dd, 0.2H), 3.17 (dd, 0.8H, J=9.2, 10.3 Hz), 3.15 (dd, 0.2H), 1.71 (s, 7.2H), 1.68 (s, 1.8H). IR (KBr): 3440 (br), 2970, 2920, 1740, 1660, 1615, 1490, 1370, 1275, 1210, 1140. Mass Spectrum (FAB): 561 [(M+1)$^+$, 7], 307 (15), 154 (100).

EXAMPLE 36

Preparation of 1-phenylsulfonyl-3-[2-(3-pyridinyl)thiazolid-4-oyl]indole

Step 1. 1-phenylsulfonyl-3-[2-(3-pyridinyl)-3-tert-butoxycarbonylthiazolid-4-oyl]-indole Powdered KOH (0.17 g, 0.0031 mol) was added to a solution of 3-[2-(3-pyridinyl)-3-tert-butoxycarbonyl-thiazolid-4oyl]indole (0.25 g, 0.00061 mol), prepared as described in Example 20, steps 1, 2 in dimethoxyethane (9 mL) at 0° C. Ten minutes later, benzene sulfonyl chloride (0.00067 mol) was added and the mixture stirred an additional 30 min. at room temperature. Benzene was added to the mixture and the insoluble materials were removed by filtration. The filtrate was washed with brine and dried over sodium sulfate. The solvent was evaporated in vacuo to afford a crystalline residue (340 mg).

Step 2. 1-Phenylsulfonyl-3-[2-(3-pyridinyl)thiazolid-4-oyl]indole

The material prepared in step 1 above was deprotected using the method of Example 1, step 5, except using trifluoroacetic acid in methylene chloride instead of HCl in dioxane to afford the desired compound.

NMR (CDCl$_3$, 300 MHz): $\delta$1.18–1.36 (t, 3H, J=7.4 Hz), 3.1–3.25 (m, 2H), 3.45–3.58 (m, 2H), 4.58 (t, 0.5H, J=7.4 Hz), 4.69–4.75 (m, 0.5H), 5.74 (s, 0.5H), 6.5 (s, 0.5H), 7.35–7.45 (m, 2H), 7.46–7.51 (m, 3H), 7.6–7.68 (m, 1H), 8.02–8.06 (c, 0.5H), 8.23 (c, 0.5H), 8.41 –8.46 (m, 1H), 8.59–8.65 (m, 1H), 8.82 (d, 0.5H, J=1.8 Hz), 8.97 (bs, 0.5H).

EXAMPLE 37

Preparation of 1-methylsulfonyl-3-[2-(3-pyridinyl)thiazolid-4-oyl-]indole

The desired compound was prepared according to the method of Example 36, except using methane sulfonyl chloride instead of benzene sulfonyl chloride.

NMR (CDCl$_3$, 3130 MHz): $\delta$3.47–3.9 (c, 2H), 5.08 (bs, 0.5H), 5.6 (bs, 0.5H), 6.28 (s, 0.5H), 6.78 (bs, 0.5H), 7.22–7.25 (m, 1H), 7.3–7.45 (m, 2H), 7.54–7.61 (dd, 1H, J=7.4, 1.8 Hz), 7.71–7.78 (m, 1H), 7.8–7.9 (m, 2H), 7.91–8.2 (c, 2H), 8.21–8.28 (d, 0.5H, J=7.4 Hz), 8.25 (d, 0.5H, J=7.4 Hz), 8.4–8.5 (m, 0.5H), 8.52–8.75 (m, 1.5H), 8.6–8.72 (m, 1H), 8.74–8.84 (m, 1H), 9. 35 (bs, 1H) 8.84 (m, 1H), 9.35 (bs, 1H).

EXAMPLE 38

Preparation of 1-dimethylcarbamoyl)-3-[2-(3-pyridinyl)thiazolid-4-oyl-]indole.

The desired compound was prepared according to the method of Example 36, except using dimethyl carbamoyl chloride instead of benzene sulfonyl chloride.

NMR (CDCl$_3$, 300 MHz): $\delta$3.11 (s, 3H), 3.14 (s, 3H), 3.4–3.47 (m, 1H), 3.52–3.6 (m, 1H), 4.52–4.6 (t, 0.5H, J=7.4 Hz), 4.69–4.76 (m, 0.5H), 5.72 (s, 0.5H), 6.05 (s, 0.5H), 7.38–7.6 (m, 0 5H), 8.12–8.21 (m, 1H), 8.38–8.42 (m, 1H), 8.58 (d, 0.5H, J=5.5 Hz), 8.62(dd, 0.5H, J=1.8, 5.5 Hz), 8.81 (d, 0.5H, J=1.8 Hz), 8.85 (dd, 0.5H, J=1.8, 5.5 Hz), 8.95(bs, 0.5H), 9.1 (d, 0.5H, J=1.8Hz).

EXAMPLE 39

Preparation of 2-methyl-3-[2-(3-pyridinyl)[thiazolid-4-oyl]indole

The desired material was prepared using the method of Example 20, except using 2-methylindole instead of indole and methyl magnesium bromide instead of ethyl magnesium bromide.

NMR (CDCl$_3$, 300 MHz): δ8.86 (d, 0.4 H, J=2.2 Hz), 8.81 (d, 0.6H, J=1.9 Hz), 8.68 (bs, 1H (NH)), 8.62 (dd, 0.6H, J=1.5, 4.8 Hz), 8.54 (dd, 0.4H, J=1.5, 4.4 Hz), 7.99 (m, 0.6H,), 7.92 (m, 0.4H), 7.72 (m, 1H), 7.34 (m, 3H), 7.24 (d, 0.6H, J=3.3 Hz), 7.22 (d, 0.4H, J=2.9 Hz), 6.07 (s, 0.4 H), 5.75 (s, 0.6 H), 4.92 (dd, 0.6H, J=7.3, 8.4 Hz), 4.84 (t, 0.4H, J=7.4 Hz), 3.73 (dd, 0.6H, J=7.0, 11.8 Hz), 3.55 (dd, 0.4H, J=7.0, 10.6 Hz), 3.14 (dd, 0.6H, J=8.5, 10.7 Hz), 3.08 (dd, 0.4H, J=7.4, 10.7 Hz), 2.82 (s, 1.8H), 2.79 (s, 1.2H). IR (KBr): 3440, 3280, 2920, 2840, 1630, 1455, 1420, 1170. Mass Spectrum (FAB): 324 [(M+1)$^+$, 12], 307 (10), 277 (10), 201 (20), 185.

EXAMPLE 40

Preparation of 1-tert-butoxycarbonyl-2-methyl-3-[2-(3-pyridinyl)thiazolid-4-oyl]indole oxalate The desired compound was prepared using the procedure of Example 28, except using 2-methyl-3-[2-(3-pyridinyl)thiazolid-4-oyl]indole prepared as described in Example 39, instead of 3-[2-(3-pyridinyl)thiazolid-4-oyl]indole.

NMR (CDCl$_3$, 300 MHz): δ8.85 (d, 0.4H, J=2.1 Hz), 8.81 (d, 0.6H, J=1.5 Hz), 8.62 (dd, 0.6H, J=1.5, 4.8 Hz), 8.55 (dd, 0.4H, J=2.1, 4.1 Hz), 8.12 (m, 1H), 7.98 (m, 0.6H), 7.86 (m, 0.4H), 7.32 (m, 4H), 6.00 (s, 0.4H), 5.52 (s, 0.6H), 4.90 (dd, 0.6H, J=7.0, 7.5 Hz), 4.83 (t, 0.4H, J=7.0 Hz), 3.53 (dd, 0.6H, J=7.0, 10.7 Hz), 3.40 (dd, J=7.0, 10.7 Hz), 3.11 (m, 1H), 2.92 (s, 1.2H), 2.88 (s, 1.8H). IR (CDCl$_3$): 3440, 2980, 2920, 1735, 1455, 1370, 1320, 1255, 1145, 1120. Mass Spectrum (FAB): [424 (M+1)$^+$, 60], 154 (100).

EXAMPLE 41

Preparation of 1-ethoxycarbonyl-3-[2-(3-pyridinyl)thiazolid-4-oyl]indole oxalate The desired compound was prepared according to the method of Example 28, except using diethyl dicarbonate instead of di-tert-butyldicarbonate. The oxalate salt was prepared as described in Example 3.

NMR (CDCl$_3$, 300 MHz): δ8.84 (d, 0.5H, J=1.2 Hz), 8.80 (d, 0.5H, J=1.3 Hz), 8.61 (dd, 0.5H, J=1.2, 4.3 Hz), 8.54 (dd, 0.5H, J=1.3, 4.5 Hz), 8.42 (s, 0.5H), 8.39 (m, 1H), 8.35 (s, 0.5H), 8.21 (bds, 0.5H, (NH)), 8.19 (bds, 0.5H, (NH)), 7.95 (m, 0.5H), 7.88 (m, 0.5H), 7.40 (m, 4H), 6.01 (bds, 0.5H), 5.73 (m, 0.5H), 4.70 (m, 1H), 4.16 (s, 1.5H), 4.12 (s, 1.5H), 3.57 (dd, 0.5H, J=7.4, 10.6 Hz), 3.43 (dd, 0.5H, J=7.4, 10.3 Hz), 3.17 (m, 1H). IR (CDCl$_3$): 3480, 3300, 3030, 2980, 2920, 1755, 1665, 1540, 1450, 15 440, 1235. Mass Spectrum (FAB): 368 [(M+1)$^+$, 20], 201 (20), 185 (100).

EXAMPLE 42

Preparation of 1-methoxycarbonyl-3-[2-(3-pyridinyl)thiazolid-4-oyl]indole oxalate.

The desired compound was prepared according to the method of Example 28, except using dimethyldicarbonate instead of di-tert-butyl dicarbonate:

NMR (CDCl$_3$, 300 MHz): δ8.84 (d, 0.5H, J=1.2 Hz), 8.80 (d, 0.5H, J=1.3 Hz), 8.61 (dd, 0.5H, J=1.2, 4.3 Hz), 8.54 (dd, 0.5H, J=1.3, 4.5 Hz), 8.42 (s, 0.5H), 8.39 (m, 1H), 8.35 (s, 0.5H), 8.21 (bds, 0.5H, (NH)), 8.19 (bds, 0.5H, (NH)), 7.95 (m, 0.5H), 7.88 (m, 0.5H), 7.40 (m, 4H), 6.01 (bds, 0.5H), 5.73 (m, 0.5H), 4.70 (m, 1H), 4.16 (s, 1.5H), 4.12 (s, 1.5H), 3.57 (dd, 0.5H, J=7.4, 10.6 Hz), 3.43 (dd, 0.5H, J=7.4, 10.3 Hz), 3.17 (m, 1H). IR (CDCl$_3$): 3480, 3300, 3030, 2980, 2920, 1755, 1665, 1540. Mass Spectrum (FAB): 368 [(M+1)$^+$, 20], 201 (20), 185 (100).

EXAMPLE 43

Preparation of 1-iso-propylsulfonyl-3-[2-(3pyridinyl)thiazolid-4-oyl]indole

The desired compound was prepared according to the method of Example 36, except using iso-propyl sulfonyl chloride instead of benzene sulfonyl chloride.

NMR (CDCl$_3$, 300 MHz): δ1.30–1.45 (6H), 3.16–3.68 (3H), 4.60–4.75 (1H), 5.72 (1H, 5), 7.31–7.34 (2H), 7.45–7.50 (2H), 7.86–7.92 (2H), 8.40–8.49 (1H), 8.53–8.60 (1H), 8.61–8.62 (1H), 8.79–8.50 (1H). Mass Spectrum (DCI/NH$_3$): 416 (M+1)$^+$, 310, 320.

EXAMPLE 44

Preparation of 1-(4-chlorobenzoyl)-3-[2-(3-pyridinyl)thiazolid-4oyl]indole

The desired compound was prepared according to the method of Example 36, except using 4-chlorobenzoyl chloride instead of benzene sulfonyl chloride.

Melting Point: 80°–84° C. NMR (CDCl$_3$, 300 MHz): δ3.15–3.50 (2H), 4.51–4.63 (1H), 5.69 (0.5H), 5.93 (0.5H), 7.44–7.51 (3H), 7.52–7.65 (3H), 7.69–7.78 (3H), 7.81–7.85 (0.5H), 7.91–7.95 (0.5), 8.16–8.22 (1H), 8.39–8.45 (1H), 8.51–8.55 (0.5H), 8.60–8.65 (0.5H), 8.75–8.81 (1H). Mass Spectrum (DCI/NH$_3$): 448 (M+1)$^+$, 310.

EXAMPLE 45

Preparation of 1-phenylmethoxycarbonyl-3-[2-(pyridinyl)thiazolid-4-oyl]indole oxalate The desired compound was prepared according to the method of Example 28, except using dibenzyldicarbonate instead of di-tert-butyldicarbonate. The oxalate salt was prepared as described in Example 3.

NMR (CDCl$_3$, 300 MHz): δ8.82 (d, 0.5H, J=1.4 Hz), 8.79 (d, 0.5H, J=2.2 Hz), 8.61 (dd, 0.5H, J=1.9, 4.8 Hz), 8.54 (dd, 0.5H, J=1.1, 4.8 Hz), 8.40 (s, 0.5H), 8.38 (m, 1H), 8.35 (s, 0.5H), 8.18 (m, 1H), 7.95 (m, 0.5H), 7.87 (m, 0.5H), 7.45 (m, 8H), 5.99 (d, 0.5H, J=8.0 Hz), 5.72 (d, J=12.9 Hz), 5.55 (bs, 1H), 5.51 (bs, 1H), 4.71 (m, 0.5H), 4.66 (m, 0.5H), 3.55 (dd, 0.5H, J=7.3, 10.2 Hz), 3.40 (dd, 0.5H, J=7.0, 10.3 Hz), 3.18 (dd, 0.5H, J=4.4, 10.8 Hz), 3.14 (dd, 0.5H, J=3.0, 7.8 Hz). IR (CDCl$_3$): 3480, 3300, 3040, 2960, 2900, 1740, 1670, 1540, 1450,

1225. Mass Spectrum (DCI/NH$_3$): 444 [(M+1)$^+$, 100], 410 (25), 324 (25), 310 (50).

EXAMPLE 46

Preparation of
1-phenylmethyl-3-[2-(3-pyridinyl)thiazolid-4-oyl]indole

The desired compound was prepared according to the method of Example 27, except using benzyl bromide instead of ethyl iodide.

NMR (CDCl$_3$, 300 MHz): $\delta$3.00–3.25 (2H), 4.81–4.89 (1H), 5.50 (2H), 5.98 (1H), 7.21–7.26 (4H), 7.31–7.35 (3H), 7.53–7.60 (1H), 7.82–7.91 (1H), 8.21–8.26 (1H), 8.45–8.59 (1H), 8.55–8.58 (1H), 8.67 (1H), 8.75 (1H), 8.90 (1H). Mass Spectrum CDCl/NH$_3$): 400 (M+H)$^+$, 401, 198, 108.

EXAMPLE 47

Preparation of
1-tert-butoyl-3-[2-(3-pyridinyl)thiazolid-4-oyl]indole

The desired compound was prepared according to the method of Example 27, except using 2,2-dimethylpropionyl chloride instead of ethyl iodide.

Melting Point: 78°–80° C. NMR (CDCl$_3$, 300 MHz): $\delta$1.22 (9H), 3.21–3.60 (2H), 4.62–4.75 (1H), 5.78 (1H), 7.39–7.48 (3H), 7.95–8.01 (1H), 8.32–8.38 (1H), 8.42–8.49 (1H), 8.55 (1H), 8.60 (1H), 8.80 (0.5H), 8.89 (0.5H), 9.10 (0.5H), 9.21 (0.5H). Mass Spectrum (DCI/NH$_3$): 394(M+1)$^+$, 310, 119.

EXAMPLE 48

Preparation of 1-diethylcarbamoyl-3-[2-(3-pyridinyl)thiazolid-4-oyl]indole

The desired compound was prepared according to the method of Example 36, except using diethylcarbamoyl chloride instead of benzenesulfonyl chloride, and using is sodium hydride in tetrahydrofuran instead of potassium hydroxide in dimethoxyethane.

Melting point: 84° C. NMR (CDCl$_3$, 300 MHz): $\delta$1.20–1.31 (6H), 3.10–3.29 (2H), 3.40–3.51 (4H), 4.50–4.58 (1H), 6.32–6.50 (1H), 7.35–7.42 (2H), 7.49–7.52 (1H), 7.70–7.77 (1H), 8.10–8.12 (1H), 8.16–8.20 (1H), 8.35–8.40 (2H), 8.61–8.68 (0.5H), 8.82–8.89 (0.5H) 9.00–9.02 (0.5H) 9.09–9.10 (0.5H). Mass Spectrum (DCI/NH$_3$): 409(M+1)$^+$, 410,107.

EXAMPLE 49

Preparation of 1-(N-methyl, N-phenyl)-3-[2-(3-pyridinyl)thiazolid-4-oyl]indole

The desired compound was prepared according to the method of Example 36, except using N-methyl N-phenylcarbamoyl chloride instead of benzenesulfonyl chloride, and using sodium hydride in tetrahydrofuran instead of potassium hydroxide in dimethoxyethane.

Melting Point: 72°–76° C. NMR (CDCl$_3$, 300 MHz): $\delta$2.60–2.90 (2H), 3.62, 4.07–4.30. (1H), 5.61–6 00(1H), 7.10–7.60 (9H), 7.98–8.30 (2H), 8.22–8.32 (2H), 8.60–8.65 (1H), 8.90 (0.5H), 9.10 (0.5H). Mass Spectrum (DCI/NH$_3$): 443 (M+1)$^+$, 310, 311,107.

EXAMPLE 50

Preparation of
7-phenylmethoxy-3-[2-(3-pyridinyl)thiazolid-4-oyl]indole

The desired material was prepared using the method of Example 20, except using 7-phenylmethoxy indole instead of indole and methylmagnesium bromide instead of ethylmagnesium bromide.

NMR (DMSO-d$_6$, 300 MHz): $\delta$12.40 (bd, 0.6H, NH), 12.30 (bd, 0.4H, NH), 8.75 (d, 0.6H, J=2.2 Hz), 8.67 (d, 0.4H, J=2.5 Hz), 8.57 (dd, 0.6H, J=1.4, 4.8 Hz), 8.5 (m, 1H), 8.46 (dd, 0.4H, J=1.4, 4.4 Hz), 8.03 (dt, 0.6H, J=2.1, 8.1 Hz), 7.88 (m, 0.4H), 7.80 (d, 0.4H, J=7.6 Hz), 7.79 (d, 0.6H, J=7.6 Hz), 7.58 (d, 2H, J=8.0 Hz), 7.42 (m, 4H), 7.13 (m, 1H), 6.93 (d, 0.6H, J=3.3 Hz), 6.91 (d, 0.4H, J=3.4 Hz), 5.97 (s, 0.6H), 5.69 (s, 0.4H), 5.31 (s, 1.2H), 5.30 (s, 0.4H), 4.90 (t, 0.6H, J=7.0 Hz), 4.83 (m, 0.4H), 3.55 (dd, 0.6H, J=7.6, 10.0 Hz), 3.48 (dd, 0.4H, J=7.0, 9.9 Hz), 3.06 (dd, 0.6H, J=9.5, 9.2 Hz), 3.00 (dd, 0.4H, J=6.9, 9.9 Hz). Mass Spectrum (DCI/NH$_3$): 416 [(M+1)$^+$, 80], 382 (25), 293 (100), 225 (85), 124.

EXAMPLE 51

Preparation of
1-dimethylcarbamoyl)-7-phenylmethoxy-3-[2-(3-pyridinyl)thiazolid-4-oyl]indole oxalate The desired compound was prepared according to the method of Example 36, except using dimethylcarbamoyl chloride instead of benzenesulfonyl chloride and using 7-phenylmethoxy-3-[2-(3-pyridinyl)-3-tert-butoxycarbonylthiazolid-4-oyl]indole instead of 3-[2-(3-pyridinyl)-3-tert-butoxycarbonylthiazolid-4-oyl]indole. The oxalate salt was prepared as described in Example 3.

Melting Point: 78°–84° C. NMR (CDCl$_3$, 300 MHz): $\delta$8.86 (d, 0.5H, J=2.3 Hz), 8.79 (d, 0.5H, J=1.6 Hz), 8.61 (dd, 0.5H, J=1.5, 5.9 Hz), 8.54 (dd, 0.5H, J=2.3, 5.6 Hz), 8.20 (m, 0.5H), 8.18 (m, 0.5H), 8.07 (s, 0.5H), 8.05 (s, 0.5H), 7.98 (m, 1H), 7.5–7.3 (m, 7H), 6.94 (dd, 0.5H, J=3.4, 6.7 Hz), 6.91 (dd, 0.5H, J=3.0, 6.5 Hz), 6.02 (d, 0.5H, J=7.4 Hz), 5.74 (bs, 0.5H), 5.13 (bs, 2H), 4.71 (m, 0.5H), 4.67 (m, 0.5H), 3.57 (dd, 0.5H, J=7.0, 10.3 Hz), 3.41 (dd, 0.5H, J=6.7, 8.8 Hz), 3.22 (m, 1H), 2.68 (s, 1.5H), 2.64 (s, 1.5H) IR (KBr): 3440, 3030, 2925, 1705, 1650, 1495, 1395, 1255. Mass Spectrum (DCI/NH$_3$): 487 (M+1)$^+$.

EXAMPLE 52

Preparation of
1-dimethylcarbamoyl-6-phenylmethoxy-3-[2-(3-pyridinyl)thiazolid-4-oyl]indole The desired compound was prepared according to the method of Example 36, except using dimethylcarbamoyl chloride instead of benzenesulfonyl chloride and using 6-phenylmethoxy-3-[2-(3-pyridinyl)-3-tert-butoxycarbonylthiazolid-4-oyl]indole instead of 3-[2-(3-pyridinyl)-3-tert-butoxycarbonylthiazolid-4-oyl]indole.

EXAMPLE 53

Preparation of
1-tert-butoxycarbonyl-7-phenylmethoxy-3-[2-(3-pyridinyl)thiazolid-4-oyl]indole The desired compound was prepared using the procedure of Example 28, except using 7-phenylmethoxy-3-[2-(3-pyridinyl)thiazolid-4-oyl]indole prepared as described in Example 33, instead of 3-[2-(3-pyridinyl)-thiazolid-4-oyl]indole.

Melting Point: 91°–96° C. NMR (CDCl$_3$, 300 MHz): 8.84 (d, 0.4H, J=1.6 Hz), 8.79 (d, 0.6H, J=1.9 Hz), 8.61 (dd, 0.6H, J=1.5, 4.8 Hz), 8.52 (m, 1.4H), 8.23 (s, 0.6H), 8.16 (s, 0.4H), 8.02 (m, 1.6H), 7.88 (m, 0.4H), 7.47 (m, 2H), 7.35 (m, 4H), 6.98 (d, 0.6H, J=3.6 Hz), 6.96 (d, 0.4H, J=3.7 Hz), 6.01 (s, 0.4H), 5.73 (bs, 0.6H), 5.23(s, 0.8H), 5.22 (s, 1.2H), 4.71 (m, 0.4H), 4.63 (t, 0.6H, J=7.1 Hz), 3.55 (dd, 0.4H, J=7.3, 10.4 Hz), 3.41 (dd, 0.6H, J=7.0, 10.7 Hz), 3.18 (m, 1H), 1.53 (s, 5.4H), 1.50 (s, 3.6H). IR (KBr): 3440, 2980, 2945, 1760, 1700, 1660, 1370, 1265. Mass Spectrum (DCI/NH3): 516 (M+1)+.

EXAMPLE 54

Preparation of 1-(N-tert-butoxycarbamoyl)-3-[2-(3-pyridinyl)thiazolid-4-oyl]indole The desired compound was prepared according to the method of Example 36, except using N-tert-butylisocyanate instead of benzene sulfonyl chloride, and potassium carbonate in methanol instead of KOH in dimethoxyethane.

Melting Point: 101°–103° C. NMR (CDCl3, 300 MHz): δ1.54–1.60 (9H),3.40–3.46 (1H),3.53–3.60 (1H),4.60–4.76 (1H),5.66–5.74 (1H),7.30–7.48 (4H),7.74–7.80 (1H),7.85–7.90 (0.5H), 7.94–7.98 (0.5H),8.30 (0.5H),8.39 (0.5H),8.42–8.46 (2H),8.53–8.55 (0.5H),8.60–8.62(0.5H),8.79–8.83 (1H). Mass Spectrum (DCI/NH3): 408 (M+1)+.

EXAMPLE 55

Preparation of 1-(4-morpholinocarbonyl)-3-[2-(3-pyridinyl)thiazolid-4-oyl]indole The desired compound was prepared according to the method of Example 27, except using N-morpholinocarbonyl chloride instead of ethyl iodide.

Melting Point: 102°–104° C. NMR (CDCl3, 300 MHz): δ3.10–3.30 (2H), 3.60–3.84 (8H), 4.60–4.71 (1H), 5.69–5.73 (1H), 7.36–7.41 (2H), 7.54–7.60 (1H), 7.84–7.97 (1H), 8.38–8.43 (2H), 8.52–8.55 (1H), 8.60–8.63 (1H), 8.78–8.84 (2H). Mass Spectrum (DCI/NH3): 422 (M+1)+.

EXAMPLE 56

Preparation of 1-tert-butoxycarbonyl-3-[2-(3-pyridinyl)-3-formylcarbonylthiazolid-4-oyl]indole Triethylamine (0.346 mL, 2.5 mmol)) and aceticformic anhydride (0.146 g, 1.67 mmol) was added to a solution of 1-tert-butoxycarbonyl-3-[2-(3-pyridinyl)-thiazolid-4-oyl]indole, prepared as described in Example 28 (0.34 g, 0.831 mmol) in THF (40 mL). The mixture was stirred for 5 hours and then saturated aqueous ammonium chloride was added. The resulting mixture was extracted with ethyl acetate and the organic phase was washed twice with saturated aqueous sodium chloride and dried over magnesium sulfate. The solvent was removed in vacuo and the residue chromatographed on silica gel eluting with ethyl acetate:hexanes (3:2) to afford the desired compound as a white solid (0.27 g, 74%).

Melting Point: 125°–130° C. NMR (CDCl3, 300 MHz): 1.74 (s, 9H), 3.35 (m, 1H), 3.50 (m, 1H), 3.65 (m, 1H), 5.68 (m, 1H), 6.18 (s, 0.5H), 6.23 (s, 0.5H), 7.40 (m, 4H), 8.15 (m, 1H), 8.35 (m, 2H), 8.49 (d, 1H), 8.60 (m, 1H). IR (CDCl3): 1660. Mass Spectrum (DCI/NH3): 438 (M+1)+.

EXAMPLE 57

Preparation of 1-tert-butoxycarbonyl-3-[2-(3-pyridinyl)-3-acetyl-thiazolid-4-oyl]indole The desired compound was prepared according to the method of Example 56, except using acetic anhydride instead of aceticformic anhydride.

Melting Point: 170°–173° C. NMR (CDCl3, 300 MHz): δ1.75 (s, 9H), 2.03 (s, 3H), 3.33 (m, 2H), 5.65 (m, 1H), 7.45 (m, 4H), 8.15 (m, 1H), 8.42 (m, 1H), 8.50 (s, 1H), 8.63 (m, 3H), 8.88 (bs, 1H). Mass Spectrum (DCI/NH3): 452 (M+1)+.

EXAMPLE 58

Preparation of 1-tert-butoxycarbonyl-3-[2-(3-pyridinyl)-3-carbamoyl-thiazolid-4-oyl]indole The desired compound was prepared according to the method of Example 56, except using trimethylsilylisocyanate instead of acetic formic anhydride.

Melting Point: 141°–143° C. NMR (CDCl3, 300 MHz): δ1.72 (s, 9H), 3.28 (m, 1H), 3.44 (m, 1H), 4.40 (bs, 1H), 5.65 (m, 0.25H), 5.73 (m, 0.75H), 6.09 (s, 0.75H), 6.19 (s, 0.25H), 7.40 (m, 4H), 8.15 (m, 1H), 8.42 (m, 1H), 8.49 (s, 1H), 8.60 (m, 2H), 8.84 (bs, 0.75H), 8.92 (bs, 0.25H). Mass Spectrum (DCI/NH3): 453 (M+H)+.

EXAMPLE 59

Preparation 1-trifluoroethyl-3-[2-(3-pyridinyl)thiazolid-4-oyl]indole

Potassium carbonate (0.828, 5.9 mmol) was added to a solution in 3.0 mL of dimethylformamide of 3-[2-(3-pyridinyl)-3-tert-butoxycarbonylthiazolid-4-oyl]indole (0.39 g, 0.70 mmol); prepared as in Example 20. Neat 2-iodo-1,1,1-trifluoroethane (0.23 g, 0.10 mmol) was added and the reaction mixture was stirred for 24 hours at ambient temperature and 24 hours at 40° C. The solids were removed by filtration and rinsed with methylene chloride. The organic solution was washed with 0.5M aqueous citric acid solution and brine, dried over Na2SO4, filtered, and the solvents were removed in vacuo. The crude material was purified by chromatography on silica gel. This material was deprotected with HCl in dioxane according to the method of Example 1, step 5 to give the desired compound.

NMR(CDCl3, 300 MHz): δ3.36–3.57 (2H), 4.56–4.70 (1H), 4.71–4.81 (2H), 5.74 (0.5H), 6.00 (0.5H), 7.30–7.38 (2H), 7.40–7.43 (2H), 7.90–7.94 (2H), 7.95–7.98 (1H), 8.40–8.45 (1H), 8.52–8.55 (0.5H), 8.60–8.63 (0.5H), 8.78–8.79 (0.5H), 8.84–8.85 (0.5H). Mass Spectrum (DCI/Nh3): 391 (M+1)+.

EXAMPLE 60

Preparation of 1-ethoxycarbonylmethyl-3-[2-(3-pyridinyl)thiazolid-4-oyl]indole

Sodium hydride (60% dispersion, 9.0 mg, 0.38 mmol) and dimethylformamide (0.5 mL) were stirred under N2 and cooled in an ice bath. A solution in 0.5 mL dimethylformamide of 3-[2-(3-pyridinyl)-3-tert-butoxycarbonylthiazolid-4-oyl]-indole, (150 mg, 0.37 mmol) prepared as in Example 20, was added over 2 min. The resulting orange solution was stirred at 5° C. for 30 min and then a solution of ethyl chloroacetate (49 mg, 0.40 mmol) in 0.25 mL of dimethylformamide was added over 1 min. The mixture was stirred at 5° C. for 30 min, then at ambient temperature for 1 hour. The reaction was quenched with 0.5 mL H$_2$O and the solvents were removed in vacuo. The residue was partitioned between H$_2$O and methylene chloride. The aqueous phase was extracted with methylene chloride. The combined organic extracts were dried over Na$_2$SO$_4$, filtered, and concentrated in vacuo. The crude material was deprotected with HCl in dioxane according to the method of Example 1, step 5 to give the desired compound.

NMR (CDCl$_3$, 300 MHz): δ1.28 (dd, 3H, J=7.5, 15 Hz), 3.12–3.26 (c, 1H), 3.40 (dd, 0.5H, J=3.0, 10.5 Hz), 3.54 (dd, 0.5H, J=3.0, 10.5 Hz), 3.61–3.80 (c, 1H), 4.25 (m, 2H, J=7.5 Hz), 4.60 (bt, 0.5H, J=7.5 Hz), 4.68 (dd, 0.5H, J=1.5, 7.5 Hz), 4.88 (s, 1H), 4.93 (s, 1H), 5.72 (s, 0.5H), 6.02 (s, 0.5H), 7.25–7.40 (c, 4H), 7.84–7.90 (c, 1H), 7.93–8.00 (c, 1H), 8.37–8.44 (c, 1H), 8.52 (dd, 0.5H, J=1.5, 4.5 Hz), 8.60 (dd, 0.5H, J=1.5, 4.5 Hz), 8.78 (d, 0.5H, J=3.0 Hz), 8.83 (d, 0.5H, J=3.0 Hz). IR (KBr): 3440, 1745, 1640, 1530, 1465, 1385, 1210, 1190, 1050, 1020. Mass Spectrum (DCI/NH$_3$): 396 (M+1)$^+$, 125, 108.

EXAMPLE 61

Preparation of
1-propyl-3-[2-(3-pyridinyl)thiazolid-4-oyl]indole

The desired compound was prepared according to the method of Example 60 except using tetrahydrofuran instead of dimethylformamide and 1-iodopropane instead of ethyl chloroacetate.

NMR (CDCl$_3$ 300 MHz): δ0.83–0.93 (3H), 1.90–2.00 (2H), 3.44–3.57 (2H), 4.09–4.22 (3H), 5.65 (0.5H), 6.07 (0.5H), 7.33–7.38 (4H), 7.75 (0.5H), 7.81–7.8 (0.5H), 7.98–8.04 (1H), 8.36–8.41 (1H), 8.55–8.61 (2H), 8.79–8.80 (0.5H), 8.91–8.93 (0.5H). Mass Spectrum (DCI/NH$_3$): 351 (M+1)$^+$.

EXAMPLE 62

Preparation of
1-ethylsulfonyl-3-[2-(3-pyridinyl)thiazolid-4-oyl]indole

The desired compound was prepared according to the method of Example 36 except using ethanesulfonyl chloride instead of phenylsulfonyl chloride.

NMR (CDCl$_3$, 300 MHz): δ1.18–1.36 (t, 3H, J=7.4 Hz), 3.10–3.25 (m, 2H), 3.45–3.58 (m, 2H), 4.58 (t, 0.5H, J=7.4 Hz), 4.69–4.75 (m, 0.5H), 5.74 (s, 0.5H), 6.50 (s, 0.5H), 7.35–7.45 (m, 2H), 7.46–7.51 (m, 3H), 7.60–7.68 (m, 1H), 8.02–8.06 (c, 0.5H), 8.23 (c, 0.5H), 8.41–8.46 (m, 1H), 8.59–8.65 (m, 1H), 8.82 (d, 0.5H, J=1.8 Hz), 8.97 (bs, 0.5H). Mass Spectrum (DCI/NH$_3$): 401 (M+1)$^+$.

EXAMPLE 63

Preparation of
1-(N-methylcarbamoyl)-3-[2-(3-pyridinyl)thiazolid-4-oyl]indole oxalate 2,2,6,6-Tetramethylpiperidine (0.09 mL, 0.49 mmol) was dissolved in Tetrahydrofuran and Butyllithium (2.5M in hexanes, 0.2 mL, 0.50 mmol) was added. The solution was cooled to −78° C. and a solution in tetrahydrofuran of 3-[-2-(3-pyridinyl)-3-tert-butoxycarbonylthiazolid-4-oyl]indole (0.20 g, 0.49 mmol), prepared as in Example 20, was added dropwise. The reaction mixture was stirred for 5 min after which neat methyl isocyanate (0.03 mL, 0.50 mmol) was added. The cold bath was removed after 15 min and the reaction mixture was stirred 16 hours at ambient temperature. The tetrahydrofuran was removed in vacuo and the residue was taken up in methylene chloride, washed with brine, dried over Na$_2$SO$_4$, filtered, and concentrated in vacuo. The crude material was purified by chromatography on silica gel. The resulting material was deprotected with HCl in dioxane according to the method of Example 1, step 5. The oxalate salt was prepared as described in Example 3.

Melting Point: 101°–102° C. NMR (CDCl$_3$, 300 MHz): δ2.96 (3H), 3.56–3.64 (2H), 4.90–4.95 (1H), 5.80 (1H), 7.30–7.40 (2H), 7.67–7.73 (1H), 8.14–8.18 (1H), 8.25–8.32 (2H), 8.33–8.39 (1H), 8.54–8.60 (1H), 8.63 (1H), 8.81–8.85 (1H). Mass Spectrum (DCI/NH$_3$): 366 (M+1)$^+$, 424.

EXAMPLE 64

Preparation of
1-(1-morpholinocarbonyl)-2-methyl-3-[2-(3-pyridinyl)thiazolid-4-oyl]indole The desired compound was prepared according to the method of Example 27 except substituting 4-morpholinecarbonyl chloride for iodoethane and substituting 2-methyl-3-[2-(3-pyridinyl)-3-tert-butoxycarbonylthiazolid-4-oyl]indole, prepared as in Example 39, for 3-[2-(3-pyridinyl)-3-tert-butoxycarbonylthiazolid-4-oyl]indole.

NMR (CDCl$_3$, 300 MHz): δ2.78–2.84 (3H), 3.25–3.30 (2H), 3.64–3.72 (8H), 4.25–4.33 (1H), 5.78 (0.5H), 6.10 (0.5H), 7.32–7.37 (3H), 7.68–7.72 (1H), 8.21–8.27 (1H), 8.32–8.36 (1H), 8.59–8.62 (1H), 8.69–8.74 (1H), 9.05–9.07 (1H). Mass Spectrum (DCI/NH$_3$): 436 (M+1)$^+$, 453.

EXAMPLE 65

Preparation of
1-dimethylcarbamoyl-2-methyl-3-[2-(3-pyridyl)thiazolid-4-oyl]indole The desired compound was prepared according to the method of Example 36, except substituting dimethylcarbamoyl chloride for benzenesulfonyl chloride and 2-methyl-3-[2-(3-pyridinyl)-3-tert-butoxycarbonylthiazolid-4-oyl]indole, prepared as in Example 39 for 3-[2-(3-pyridinyl)-3-tert-butoxycarbonylthiazolid-4-oyl]indole.

Melting Point: 130°–132° C. NMR (CDCl$_3$ 300 MHz): δ2.67–2.75 (3H), 3.18–3.21 (6H), 3.61–3.74 (2H), 4.77–4.82 (0.5H), 5.01–5.10 (0.5H), 5.78 (0.5H), 5.85 (0.5H), 7.21–7.44 (4H), 7.88–7.93 (0.5H), 7.93–8.00 (0.5H), 8.00–8.05 (1H), 8.05–8.13 (1H), 8.47–8.54 (1H), 8.2–8.60 (1H). Mass Spectrum (DCI/NH$_3$): 394 (M+1)$^+$.

EXAMPLE 66

Preparation of
2,5-dimethyl-3-[2-[3-pyridinyl)thiazolid-4-oyl]indole oxalate

The desired compound was prepared according to the method of Example 20 except using 2,5-dimethylindole instead of indole. The oxalate salt was prepared as in Example 3. NMR (CDCl$_3$, 300 MHz): δ2.42 (s, 3H), 2.52 (s, 3H), 3.08–3.18 (m, 2H), 4.80–4.91 (m, 1H), 5.74 (s, 0.5H), 6.05 (s, 0.5H), 7.02–7.11 (m, 1H), 7.32–7.39 (m, 1H), 7.71 (s, 1H), 7.88–7.92 (m, 0.5H), 7.97–8.01 (m, 1H), 8.51–8.55 (m, 0.5H), 8.60–8.62 (d, 1H), 8.80–8.81 (d, 1H). Mass Spectrum (DCI/NH$_3$): 337 (M+1)$^+$ 146.

EXAMPLE 67

Preparation of
1-tert-butoxycarbonyl-2,5-dimethyl-3-[2-[3-pyridinyl)-thiazolid-4-oyl]indole oxalate The desired compound was prepared according to the method or Example 28 except using 2,5-dimethyl-3-[2-(3-pyridinyl)thiazolid-4-oyl]-indole, prepared as in Example 66 instead of 3-[2-(3-pyridinyl)thiazolid-4-oyl]-indole. The oxalate salt prepared according to the method of Example 3.

NMR (CDCl$_3$, 300 MHz): δ1.69–1.73 (9H), 2.42 (s, 3H), 2.52 (s, 3H), 3.08–3.18 (m, 1H), 4.80–4.91 (m, 1H), 5.74 (s, 0.5H), 6.05 (s, 0.5H), 7.02–7.11 (m, 1H), 7.32–7.39 (m, 1H), 7.71 (s, 1H), 7.88 (m, 0.5H), 7.97–8.01 (m, 1H), 8.51–8.55 (m, 0.5H), 8.60–8.62 (d, 1H), 8.80–8.81 (d, 1H). Mass Spectrum (DCI/NH$_3$): 437 (M+1)$^+$, 434, 380.

EXAMPLE 68

Preparation of
1-(4-morpholinocarbonyl)-2,5-dimethyl-3-[2-(3-pyridinyl)thiazolid-4-oyl]indole The desired compound was prepared according to the method of Example 27 except substituting 4-morpholinecarbonyl chloride for iodoethane and substituting 2,5-dimethyl-3-[2-(3-pyridinyl)-3-tert-butoxycarbonylthiazolid-4-oyl]indole, prepared as in Example 20, steps 1 and 2, for 3-[2-(3-pyridinyl)-3-tert-butoxycarbonylthiazolid-4oyl]indole.

Melting Point: 87°–90° C. NMR (CDCl$_3$, 300 MHz): δ2.53 (3H), 2.80 (3H), 3.50–3.62 (2H), 3.62–3.95 (8H), 4.83–4.93 (1H), 7.10–7.40 (3H), 7.70 (1H), 7.97–8.02 (1H), 8.53–8.55 (1H), 8.60–8.63 (1H), 8.78–8.90 (1H). Mass Spectrum (DCI/NH$_3$): 450 (M+1)$^+$, 417.

EXAMPLE 69

Preparation of
1-dimethylcarbamoyl-2,5-dimethyl-3-[2-(3-pyridinyl)-thiazolid-4oyl]indole oxalate The desired compound was prepared according to the method of Example 67 except substituting dimethylcarbamyl chloride for di-tert-butyldicarbonate. The oxalate salt was prepared according to the method of Example 3.

Melting Point: 79°–82° C. NMR (CDCl$_3$, 300 MHz): δ2.43 (3H), 2.70 (3H), 3.31 (6H), 3.55–3.64 (2H), 4.97 (1H), 5.87 (1H), 7.13–7.23 (2H), 7.70–7.75 (1H), 7.78–7.87 (1H), 8.32–8.40 (0.5H), 8.45–8.40 (1H), 8.64–8.66 (0.5H), 8.77–8.83 (0.5H), 8.90 (0.5H). Mass Spectrum (DCI/NH3): 408 (M+1)$^+$.

EXAMPLE 70

Preparation of
3-[2-(3-pyridinyl)thiazolid-4-oyl]-6-(4-fluorophenoxy)indole

Step 1. 2-Nitro-4-(4-fluorophenoxy)toluene.

4-Bromo-2-nitrotoluene (25.0 g, 116 mmol), 4-fluorophenol (8.70 g, 77.6 mmol), potassium carbonate (21.5 g, 156 mmol) and pyridine (75 mL), were combined under N$_2$ atmosphere and heated at 90° C. for 30 min. The reaction mixture was cooled to ambient temperature, CuO (15.4 g, 194 mmol) was added under a stream of N$_2$, and the resulting dark-brown suspension was heated at reflux for 17 hours. The reaction mixture was cooled to ambient temperature and diluted with ether. The solids were removed by filtration through celite. The ethereal solution was washed with 1.0M aqueous NaOH, 1.0M aqueous HCl and brine, dried over Na$_2$SO$_4$, filtered and concentrated in vacuo to give a dark-brown oil. The crude product was purified by chromatography on silica gel to give 2-nitro-4-(4-fluorophenoxy)-toluene (12.1 g, 63%).

Step 2. E.-1(1-pyrrolidinyl)-2-[2-nitro-4-(4-fluorophenoxy)phenyl]ethylene.

2-Nitro-4-(4-fluorophenoxy)toluene (11.8 g, 47.7 mmol), was dissolved in dimethylformamide (90.0 mL) under N$_2$ atmosphere. Dimethylformamide dimethyl acetal (20.2 mL, 143 mmol), and pyrrolidine (4.0 mL, 47.4 mmol) were added via syringe and the reaction mixture was heated at 110° C. for 3 hours. The reaction mixture was cooled to ambient temperature and partitioned between H$_2$O and ether. The organic phase was washed with H$_2$O. The combined aqueous extracts were washed with ether. The ether extracts were combined and dried over Na$_2$SO$_4$, filtered, and concentrated in vacuo to give a viscous oil (16.1 g) which was used without further purification.

Step 3. 6-(4-fluorophenoxy)indole.

The material prepared as in step 2 was dissolved in 80% aqueous acetic acid (320 mL, 4540 mmol) arid the reaction mixture was warmed to 75° C. Zinc dust (27 g, 413 mmol) was added in 5 portions over 1 hour. The resulting dark-brown suspension was warmed to 90° C. and heated for two hours. The reaction mixture was cooled to ambient temperature and diluted with ether. The solids were removed by filtration through celite. The filter cake was rinsed with H$_2$O and ether. The layers were separated and the organic phase was washed with H$_2$O, with saturated aqueous NaHCO$_3$ until basic, then once with brine, dried over Na$_2$SO$_4$, filtered, and concentrated in vacuo. The crude product was purified by chromatography on silica gel to give 6-(4-fluorophenoxy)-indole (1.8 g, 17%)

Step 4. 3-[2-(3-pyridinyl)thiazolid-4-oyl]-6-(4-fluorophenoxy)indole.

The desired compound was prepared according to the method of Example 20, except substituting 6-(4-fluorophenoxy)indole for indole.

Melting Point: 189°–191° C. NMR (DMSO-d6, 300 MHz): δ3.00 (dd, 0.5H, J=7.6, 10.1 Hz), 3.05 (t, 0.5H, J=9.6 Hz), 3.46 (dd, 0.5H, J=7.4, 9.9 Hz), 4.09 (t, 1H, J=10.0 Hz), 4.78 (dt, 0.5H, J=8, 11 Hz), 4.85 (dt, 0.5H, J=8, 11 Hz), 5.68 (d, 0.5H, J=12.9 Hz), 5.96 (d, 0.5H, J=9.2 Hz), 6.9 (dt, 1H, J=2.4, 8.6 Hz), 7.01–7.08 (c, 3H), 7.21 (t, 2H, J=8.6 Hz), 7.36 (dd, 0.5H, J=4.6, 7.9 Hz), 7.44 (dd, 0.5H, J=5.0, 7.9 Hz), 7.86 (d, 0.5H, J=7.7 Hz), 8.02 (d, 0.5H, J=7.7 Hz), 8.18 (dd, 1H, J=2.4, 8.6 Hz), 8.46 (dd, 0.5H, J=1.6, 4.6 Hz), 8.55 (dd, 0.5H, J=1.5, 4.6 Hz), 8.56 (d, 1H, J=3.3 Hz), 8.65 (d, 0.5H, J=2.2 Hz), 8.73 (d, 0.5H, J=1.8 Hz), 12.03 (br s, 1H). IR (KBr): 807 (m), 825 (m), 844 (m), 1196 (s), 1241 (m), 1420 (s), 1449 (s), 500 (s), 1528 (m), 1638 (s), 3425 (br). Mass Spectrum (DCI/NH$_3$): 420 (M+1)$^+$.

EXAMPLE 71

Preparation of
1-dimethylcarbamoyl-3-[2-(3-pyridinyl)thiazolid-4-oyl]-6-(4-fluorophenoxy)indole The desired compound was prepared according to the method of Example 36 except substituting dimethylcarbamoyl chloride for benzenesulfonyl chloride and substituting 3-[2-(3-pyridinyl)-3-tert-butoxycarbonylthiazolid-4-oyl]-6-(4-fluorophenoxy)indole, prepared as in Example 70 for 3-[2-(3-pyridinyl)thiazolid-4-oyl]indole.

Melting Point: 72°–75° C. NMR (DMSO-d6, 300 MHz): δ3.00 (s, 3H), 3.03 (s, 3H), 3.12 (t, 0.5H, J=9.6 Hz), 3.47 (dd, 0.5H, J=8.1, 11 Hz), 3.54 (t, 0.5H, J=7.7 Hz), 4.17 (t, 1H, J=9 Hz), 4.85 (dt, 0.5H, J=8, 12 Hz), 4.97 (dt, 0.5H, J=7, 10 Hz), 5.69 (d, 0.5H, J=12.9 Hz), 5.92 (d, 0.5H, J=9.2 Hz), 7.04–7.12 (c, 3H), 7.18–7.27 (c, 3H), 7.36 (dd, 0.5H, J=4.6, 7.9 Hz), 7.87 (d, 0.5H, J=8.1 Hz), 8.01 (d, 0.5H, J=8.1 Hz), 8.23 (dd 1H, J=4.2, 8.6 Hz), 8.46 (dd, 0.5H, J=1.6, 4.6 Hz), 8.54 (dd, 0.5H, J=1.5, 4.8 Hz), 8.66 (d, 0.5H, J=2.2 Hz), 8.73 (d, 0.5H, J=1.8 Hz), 8.82 (d, 1H, J=1.8 Hz). Mass Spectrum (DCI/NH3): 491 (M+1)+.

EXAMPLE 72

Preparation of 1-(4-morpholinocarbonyl)-3-[2-(3-pyridinyl)thiazolid-4-oyl]-6-phenylmethoxyindole oxalate The desired compound was prepared according to the method of Example 36 except substituting 4-morpholinecarbonyl chloride for benzenesulfonyl chloride and substituting 3-[2-(3-pyridinyl)-3-tert-butoxycarbonylthiazolid-4-oyl]-6-phenylmethoxyindole, prepared as in Example 34 for 3-[2-(3-pyridinyl)-3-tert-butoxycarbonylthiazolid-4-oyl]indole. The oxalate salt was prepared according to the method of Example 3.

NMR (CDCl3, 300 MHz): δ3.24 (m, 3H), 3.54 (m, 2H), 3.67 (m, 3H), 3.88 (m, 2H), 4.11 (m, 1H), 5.17 (s, 2H), 5.78 (s, 0.4H), 6.02 (s, 0.6H), 7.06 (m, 1H), 7.17 (m, 1H), 7.38 (m, 4H), 7.45 (m, 2H), 7.58 (dd, 0.4H, J=5.7, 7.1 Hz), 7.67 (dd, 0.6H, J=5.7, 7.1 Hz), 8.19 (m, 1H), 8.41 (s, 0.6H), 8.46 (s, 0.4H), 8.56 (m, 0.6H), 8.63 (m, 0.4H), 8.80 (d, 0.4H, J=2.1 Hz), 8.82 (d, 0.6H, J=2.1 Hz). IR (CDCl3): 3300, 2960, 2920, 2850, 1690, 1660 (sh), 1415, 1220. Mass Spectrum (DCI/NH3): 529 [(M+1)+, 25], 201 (100). Exact Mass: Theoretical: 529.190; Experimental: 529.189.

EXAMPLE 73

Preparation of 1-ethylsulfonyl-3-[2-(3-pyridinyl)thiazolid-4-oyl]-6-phenylmethoxyindole The desired compound was prepared according to the method of Example 27 except substituting 3-[2-(3-pyridinyl)-3-tert-butoxycarbonylthiazolid-4-oyl]-6-phenylmethoxyindole, prepared as in Example 34, for 3-[2-(3-pyridinyl)-3-tert-butoxycarbonylthiazolid-4-oyl]-indole, and substituting ethanesulfonyl chloride for iodoethane.

Melting Point:76°–82° C. NMR (CDCl3, 300 MHz): δ3.18 (m, 1H), 3.33 (t, 3H, J=7.0 Hz), 3.39 (dd, 0.5H. J=7.0, 11.3 Hz), 3.54 (dd, 0.5H, J=7.3, 11.3 Hz), 4.12 (q, 2H, J=7.0 Hz), 4.60 (t, 0.5H, J=7.3 Hz), 4.64 (dd, 0.5H, J=7.4, 11.7 Hz), 5.17 (s, 2H), 5.71 (s, 0.5H), 5.98 (s, 0.5H), 7.14 (dd, 0.5H, J=1.5, 2.2 Hz), 7.16 (dd, 0.5H, J=1.4, 2.2 Hz), 7.40 (m, 7H), 7.94 (m, 1H), 8.06 (s, 0.5H), 8.11 (s, 0.5H), 8.27 (d, 0.5H, J=4.4 Hz), 8.30 (d, 0.5H, J=4.4 Hz), 8.56 (dd, 0.5H, J=1.3, 4.8 Hz), 8.62 (dd, 0.5H, J=1.5, 4.8 Hz), 8.79 (d, 0.5H, J=2.2 Hz), 8.85 (d, 0.5H, J=2.3 Hz). IR (KBr): 3430 (br), 2920, 1660, 1610, 1530, 1375, 1205. Mass Spectrum (DCI/NH3): 508 [(M+1)+, 10], 165 (100). Exact Mass: Theoretical: 508.136; Experimental: 508.135.

EXAMPLE 74

Preparation of 3-[2-(3-pyridinyl)thiazolid-4-oyl]-6-(4-fluorophenylmethoxy)indole Step 1. 6-Hydroxyindole.

6-Phenylmethoxyindole (3.93 g, 17.6 mmol), was suspended in acetone (350 mL), under N2 and cooled in an ice bath. 10% Palladium on carbon (0.80 g) was added, and the N2 atmosphere was replaced with H2 by alternately placing the reaction flask under vacuum and introducing H2 from a balloon. The cold bath was then removed and the reaction mixture stirred under positive H2 pressure for 16 hours. The reaction mixture was cooled in an ice bath, and N2 reintroduced. The reaction mixture was filtered through a pad of celite and concentrated in vacuo. The crude product was purified by chromatography on silica gel to give 6-hydroxyindole (1.70 g, 73%).

Step 2. 6-(4-fluorophenylmethoxy)indole.

6-Hydroxyindole (0.90 g, 6.8 mmol) and potassium carbonate (1.04 g, 7.5 mmol), were suspended in 13 mL of acetone. 4-Fluorobenzyl bromide (0.93 mL, 7.5 mmol, prefiltered through basic alumina) was added dropwise via syringe. The reaction mixture was heated at reflux under N2 atmosphere for 24 hours. The reaction mixture was cooled to ambient temperature and partitioned between H2O and methylene chloride. The aqueous phase was extracted twice with methylene chloride. The combined organic extracts were washed with brine, dried over Na2SO4, filtered, and concentrated in vacuo. The crude material was purified by chromatography on silica gel to give 6-(4-fluorophenylmethoxy)indole (1.4 g, 88%).

Step3. 3-[2-(3-pyridinyl)thiazolid-4-oyl]-6-(4-fluorophenylmethoxy)indole.

The desired compound was prepared according to the method of Example 20, except substituting 6-(4-fluoromethoxyphenyl)indole for indole.

Melting Point: 185°–186° C. NMR (DMSO-d6, 300 MHz): δ2.96 (dd, 0.5H, J=7.6, 10.1 Hz), 3.04 (t, 0.5H, J=9.4 Hz), 3.46 (dd, 0.5H, J=7.0, 9.9 Hz), 3.52 (dd, 0.5H, J=7.4, 9.9 Hz), 4.82 (c, 1H), 5.12 (s, 2H), 5.67 (s, 0.5H), 5.98 (s, 0.5H), 6.94 (dt, 1H, J=2.1, 8.6 Hz), 7.04 (dd, 1H, J=2.0, 5.0 Hz), 7.21 (t, 2H, J=9.0 Hz), 7.36 (dd, 0.5H, J=5.2, 7.8 Hz), 7.44 (dd, 0.5H, J=4.8, 7.7 Hz), 7.52 (dd, 2H, J=5.5, 8.8 Hz), 7.85 (d, 0.5H, J=7.7 Hz), 8.01 (d, 0.5H, J=8.1 Hz). 8.07 (dd, 1H, J=2.4, 8.6 Hz), 8.46 (dd, 0.5H, J=1.5, 4.5 Hz), 8.48 (t, 1H, J=3.8 Hz), 8.56 (dd, 0.5H, J=1.8, 4.8Hz),8.65(d, 0.5H, J=2.0 Hz), 8.73 (d, 0.5H, J=1.8 Hz), 11.95 (s, 0.5H), 12.02 (s, 0.5H). Mass Spectrum (DCI/NH3): 434 (M+1)+.

EXAMPLE 75

Preparation of 1-dimethylcarbamoyl-3-[2-(3-pyridinyl)thiazolid-4-oyl]-6-(4-fluorophenylmethoxy)indole The desired compound was prepared according to the method of Example 36, except substituting 3-[2-(3-pyridinyl)-3-tert-butoxycarbonylthiazolid-4-oyl]-6-(4-fluorophenylmethoxy)indole, prepared as in Example 74, for 3-[2-(3-pyridinyl)-3-tert-butoxycarbonylthiazolid-4-oyl]indole, and substituting dimethylcarbamoyl chloride for benzenesulfonyl chloride.

Melting Point: 71°–74° C. NMR (DMSO-d6, 300 MHz): δ3.02 (s, 3H), 3.05 (s, 3H), 3.09 (dd, 0.5H, J=10.7, 14.3 Hz), 3.12 (dd, 0.5H, J=9.8, 13.8 Hz), 3.48, (dd, 0.5H, J=7.4, 9.9 Hz), 3.54 (dd, 0.5H, J=7.2, 9.8 Hz), 4.17 (br s, 1H), 4.82 (t, 0.5H, J=7.9 Hz), 4.95 (t, 0.5H, J=6.8 Hz), 5.16 (s, 2H), 5.70 (s, 0.5H), 5.94 (s, 0.5H), 7.08 (d, 1H, J=8.8 Hz), 7.22 (s, 1H), 7.24 (t, 2H, J=8.8 Hz), 7.38 (dd, 0.5H, J=4.8, 7.7 Hz), 7.46 (dd, 0.5H, J=4.8, 7.7 Hz), 7.54 (dd, 2H, J=5.7, 8.6 Hz), 7.88 (d, 0.5H, J=7.4 Hz), 8.04 (d, 0.5H, J=8.4 Hz), 8.15 (dd, 1H, J=3.1, 8.6 Hz), 8.48 (dd, 0.5H, J=1.5, 4.8 Hz), 8.56 (dd, 0.5H, J=1.5, 4.8 Hz), 8.68 (d, 0.5H, J=2.0 Hz), 8.75 (d, 0.5H, J=2.0 Hz), 8.75 (s, 1H). Mass Spectrum (DCI/NH$_3$): 505 (M+1)$^+$.

EXAMPLE 76

Preparation of 3-[2-(3-pyridinyl)thiazolid-4-oyl]-6-(3-methylpyridinyl)indole

Step 1. 6-(3-methylpyridinyl)indole.

The desired compound was prepared according to the method of Example 74, step 2 except substituting 3-(chloromethyl)pyridine for 4-fluorobenzyl bromide.

Step 2. 3-[2-(3-pyridinyl)thiazolid-4-oyl]-6-(3-methylpyridinyl)indole.

The desired compound was prepared according to the method of Example 20 except substituting 6-(3-methylpyridinyl)-indole for indole.

Melting Point: 88°-93° C. NMR (CDCl$_3$, 300 MHz): δ3.13 (t, 0.5H, J=9.6 Hz), 3.19 (t, 0.5H, J=9.6 Hz), 3.37 (t, 0.5H, J=8.6 Hz), 3.50 (t, 0.5H, J=8.6 Hz), 4.43 (br s, 1H), 4.58 (t, 0.5H, J=7.4 Hz), 4.67 (t, 0.5H, J=8.1Hz), 5.11 (s, 2H), 5.71 (s, 0.5H), 6.03(s, 0.5H), 6.95(s, 1H), 7.04 (d, 1H, J=8.8 Hz), 7.29–7.40 (c, 2H), 7.76–8.00 (c, 3H), 8.28 (d, 1H, J=8.5 Hz), 8.49–8.64 (c, 2H), 8.69 (s, 1H), 8.79 (s, 0.5H), 8.84 (s, 0.5H), 9.94 (s, 0.5H), 10.09 (s, 0.5H). Mass Spectrum (DCI/NH$_3$): 417 (M+1)$^+$.

EXAMPLE 77

Preparation 3-[2-(3-pyridinyl)thiazolid-4-oyl]-6-phenylethynylindole

Step: 1. E-1-(1-pyrrolidinyl)-2-(4-bromo-2-nitrophenyl)ethylene.

The desired compound was prepared according to the method of Example 70 step 2 except substituting 4-bromo-2'-nitrotoluene for 2-nitro-4-(4-fluorophenoxy)toluene. The crude material was used with no further purification.

Step 2. 6-Bromoindole.

The material obtained as in step 1 (32.9 g) was combined with Raney nickel 2800 (32.9 g) and toluene (2.0 L) and stirred under a pressure of 4 atmospheres of hydrogen for 2 hours. The reaction mixture was filtered and concentrated in vacuo. The crude product was purified by chromatography on silica gel to give 6-bromoindole (17.4 g, 78% yield from 4-bromo-2-nitrotoluene).

Step 3. 6-Phenylethynylindole.

6-Bromoindole (3.84 g, 19.6 mmol) was dissolved in triethylamine (40 ml.). A catalytic amount of phenothiazine was added, and the solution was degassed by bubbling argon through it. Phenylacetylene (8.60 mL, 78.3 mmol) was added via syringe. Bis(triphenylphosphine)palladium(II) chloride (0.69 g, 0.98 mmol) was added, and the reaction mixture was heated at 75°-85° C. for 5 hours. The reaction mixture was cooled to ambient temperature and filtered. The filtrate was concentrated in vacuo. The crude material was purified by chromatography on silica gel to give 6-phenylethynylindole (2.55 g, 60%).

Step 4. 3-[2-(3-pyridinyl)thiazolid-4-oyl]-6-phenylethynylindole.

The desired compound was prepared according to the method of Example 20 except substituting 6-phenylethynylindole for indole.

Melting Point: 103°-107° C. NMR (CDCl$_3$, 300 MHz): δ3.16 (dd, 0.5H, J=8.1, 10.3 Hz), 3.20 (dd, 0.5H, J=9.2, 10.3 Hz), 3.38 (dd, 0.5H, J=6.8, 10.5 Hz), 3.50 (dd, 0.5H, J=7.4, 10.3 Hz), 4.58 (t, 0.5H, J=7.6 Hz), 4.66 (t, 0.5H, J=8.1 Hz), 5.70 (s, 0.5H), 6.02 (s, 0.5H), 7.27–7.38 (c, 4H), 7.46 )dd, 0.5H, J=1.5, 3.7 Hz), 7.50 (dd, 0.5H, J=1.3, 3.8 Hz), 7.52 (d, 0.5H, J=1.8 Hz), 7.53 (s, 0.5H), 7.56 (d, 0.5H, J=2.6 Hz), 7.59 (s, 0.5H), 7.86–8.15 (c, 3H), 8.34 (dd, 0.5H, J=2.2, 8.1 Hz), 8.44 (dd, 0.5H, J=2.0, 8.3 Hz), 8.53 (d, 0.5H, J=4.8 Hz), 8.60 (dd, 0.5H, J=1.5, 4.8 Hz), 8.78 (d, 0.5H, J=1.5 Hz), 8.86 (d, 0.5H, J=2.6 Hz), 10.00 (s, 0.5H), 10.15 (s, 0.5H). IR (KBr): 1417 (s), 1445 (s), 1523 (m), 1622 (s), 1646 (s), 3282 (br), 3402 (br). Mass Spectrum (DCI/NH$_3$): 410 (M+1)$^+$.

EXAMPLE 78

Preparation of 1-dimethylcarbamoyl-3-[2-(3-pyridinyl)thiazolid-4-oyl-6-phenylethynylindole.

The desired compound was prepared according to the method of Example 36 except substituting 3-[2-(3-pyridinyl)-3-tert-butoxycarbonylthiazolid-4-oyl]-6-phenylethynylindole, prepared as in Example 77 for 3-[2-(3-pyridinyl)-3-tert-butoxycarbonylthiazolid-4-oyl]indole, and substituting dimethylcarbamyl chloride for benzenesulfonyl chloride.

Melting Point: 84°-88° C. NMR (CDCl$_3$, 300 MHz): δ3.12 (s, 3H), 3.13 (t, 0.5H, J=9.9 Hz), 3.16 (s, 3H), 3.22 (t, 0.5H, J=9.6 Hz), 3.42 (dd, 0.5H, J=7.4, 10.3 Hz), 3.56 (dd, 0.5H, J=7.4, 10.3 Hz), 4.63 (t, 0.5H, J=7.6 Hz), 4.69 (dd, 0.5H, J=7.0, 8.8 Hz), 5.72 (s, 0.5H), 5.98 (s, 0.5h), 7.3–7.40 (c, 4H), 7.52–7.60 (c, 3H), 7.71 (s, 1H), 7.88 (d, 0.5H, J=8.1Hz), 7.96 (dt, 0.5H, J=1.9, 7.8 Hz), 8.15 (s, 0.5H), 8.19 (s, 0.5H), 8.37 (dd, 1H, J=3.8, 8.3 Hz), 8.54 (d, 0.5H, J=4.0 Hz), 8.61 (dd, 0.5H, J=1.5, 4.8 Hz), 8.79 (d, 0.5H, J=2.2 Hz), 8.83 (s, 0.5H). IR (KBr): 1390 (s), 1661 (s), 1700 (s), 3436 (br). Mass Spectrum (DCI/NH$_3$): 481 (M+1)$^+$.

EXAMPLE 79

Preparation of 2-methyl-3-[2-(3-pyridinyl)thiazolid-4-oyl]-6-phenylmethoxyindole The desired compound was prepared according to the method of Example 20 except substituting 2-methyl-6-phenylmethoxyindole for indole.

Melting Point: 89°-93° C. NMR (CDCl3, 300 MHz): δ2.41 (s, 1.5H), 2.43 (s, 1.5H), 3.18 (m, 1H), 3.39 (dd, 0.5H, J=7.0, 10.9 Hz), 3.52 (dd, 0.5H, J=7.0, 10.7 Hz), 4.58 (dd, 0.5H, J=7.0, 7.1 Hz), 4.69 (dd, 0.5H, J=7.0, 7.2 Hz), 5.16 (s, 2H), 5.72 (s, 0.5H), 6.03 (s, 0.5H), 7.06 (d, 0.5H, J=3.3 Hz), 7.08 (d, 0.5H, J=2.9 Hz), 7.36 (m, 3H), 7.40 (d, 1H, J=7.0 Hz), 7.47 (d, 1H, J=7.0 Hz), 7.93 (m, 3H), 8.14 (s, 0.5H), 8.16 (s, 0.5H), 8.52 (dd, 0.5H, J=1.4, 4.6 Hz), 8.60 (dd, 0.5H, J=1.5, 4.8 Hz), 8.79 (d, 0.5H, J=1.5 Hz), 8.86 (d, 0.5H, J=1.4 Hz). IR (KBr): 3430 (br), 3300 (sh), 2930, 1615, 1515, 1410. Mass Spectrum (DCI/NH3): 430 (M+1)$^+$. Exact Mass: Theoretical: 430.158; Experimental: 430.157.

EXAMPLE 80

Preparation of
3-[2-(3-pyridinyl)thiazolid-4-oyl]-6-methylindole

The desired compound was prepared according to the method of Example 20, except substituting 6-methylindole for indole.

Melting Point: 132°–138° C. NMR (CDCl$_3$, 300 MHz): δ2.48 (s, 1.2H), 2.49 (s, 1.8H), 3.17 (dd, 0.4H, J=6.9, 10.8 Hz), 3.20 (dd, 0.6H, J=9.2, 10.3 Hz), 3.38 (dd, 0.4H, J=7.0, 10.8 Hz), 3.53 (dd, 0.6H, J=6.9, 10.2 Hz), 4.58 (t, 0.4H, J=7.0 Hz), 4.69 (dd, 0.6H, J=6.9, 9.2 Hz), 5.73 (s, 0.6H), 6.04 (s, 0.4H), 7.17 (m, 2H), 7.33 (m, 1H), 7.86 (d, 0.4H, J=2.9 Hz), 7.94 (d, 0.6H, J=2.9 Hz), 7.96 (m, 0.6H), 7.99 (m, 0.4H), 8.24 (s, 0.4H), 8.27 (s, 0.6H), 8.53 (dd, 0.4H, J=2.2, 4.3 Hz), 8.61 (dd, 0.6H, J=1.5, 4.8 Hz), 8.70 (bs, 1H), 8.79 (d, 0.6H, J=2.2 Hz), 8.85 (d, 0.4H, J=2.2 Hz). IR (KBr): 3430, 3240, 2930, 1615, 1525, 1440, 1420. Mass Spectrum (DCI/NH$_3$): 324 (M+1)$^+$, 107.

EXAMPLE 81

Preparation of
1-tert-butoxycarbonyl-3-[2-(3-pyridinyl)thiazolid-4-oyl]-6-methylindole oxalate The desired compound was prepared according to the method of Example 28 except substituting 3-[2-(3-pyridinyl)thiazolid-4-oyl]-6-methylindole, prepared as in Example 80, for 3-[2-(3-pyridinyl)thiazolid-4-oyl]indole.

Melting Point: 95°–98° C. NMR (CDCl$_3$, 300 MHz): δ1.56 (s, 0.9H), 1.70 (s, 6.3H), 1.73 (s, 2.7H), 2.50 (s, 2.1H), 3.17 (m, 1H), 3.42 (dd, 0.7H, J=7.0, 10.7 Hz), 3.56 (dd, 0.3H, J=7.0, 10.3 Hz), 4.63 (m, 1H), 5.74 (bds, 0.3H), 6.02 (bds, 0.7H), 7.22 (m, 1H), 7.30 (dd, 0.7H, J=0.8, 5.5 Hz), 7.45 (dd, 0.3H, J=4.2, 5.5 Hz), 7.87 (m, 0.7H), 7.98 (m, 1.3H), 8.23 (m, 1H), 8.25 (s, 0.3H), 8.29 (s, 0.7H), 8.53 (dd, 0.7H, J=1.1, 4.7 Hz), 8.62 (dd, 0.3H, J=1.6, 4.8 Hz), 8.80 (d, 0.3H, J=1.9 Hz), 8.83 (d, 0.7H, J=2.2 Hz). IR (CDCl$_3$): 3300, 3150, 2980, 2930, 1735, 1665, 1540, 1375, 1240. Mass Spectrum (DCI/NH$_3$): 424 (M+1)$^+$, 392.

EXAMPLE 82

Preparation
3-[2-(3-pyridinyl)thiazolid-4-oyl]-6-methoxyindole

The desired compound was prepared according to the method of Example 20, except substituting 6-methoxyindole for indole.

Melting Point: 86°–88° C. NMR (CDCl$_3$, 300 MHz): δ3.35–3.58 (2H), 3.84–3.87 (3H), 4.50–4.73 (1H), 5.73–6.05 (1H), 6.90–7.02 (2H), 7.33–7.41 (2H), 7.46–7.52 (1H), 7.83–7.85 (0.5H), 7.90–7.93 (0.5H), 7.98–8.12 (1H), 8.54–8.62 (2H), 8.78–8.80 (0.5H), 8.90–8.93 (0.5H). Mass Spectrum (DCI/NH$_3$): 339 (M+1)$^+$, 306.

EXAMPLE 83

Preparation of
3-[2-(3-pyridinyl)thiazolid-4-oyl]-6-methoxyindole oxalate

The desired compound was prepared according to the method of Example 3, except substituting 3-[2-(3-pyridinyl)thiazolid-4-oyl]-6-methoxyindole for 1-[2-(3-pyridinyl)-4-oyl]-indole.

Melting Point: 115°–118° C.

EXAMPLE 84

Preparation of
1-tert-butoxycarbonyl-3-[2-(3-pyridinyl)thiazolid-4-oyl]-6-methoxyindole oxalate The desired compound was prepared according to the method of Example 28 except substituting 3-[2-(3-pyridinyl)thiazolid-4-oyl]-6-methoxyindole, prepared as in Example 82, for 3-[2-(3-pyridinyl)thiazolid-4-oyl]indole.

Melting Point: 99°–100° C. NMR (CDCl$_3$, 300 MHz): δ1.69–1.74 (9H), 3.42–3.60 (2H), 3.89 (3H), 4.60–4.75 (1H), 5.75 (1H), 6.98–7.30 (1H), 7.44–7.50 (0.5H), 7.56–7.63 (0.5H), 7.67 (1H), 8.06–8.12 (0.5H), 8.18–8.24 (2H), 8.26 (0.5H), 8.64–8.67 (1H), 8.83–8.85 (0.5H), 8.97–9.00 (0.5H). Mass Spectrum (DCI/NH$_3$): 439 (M+1)$^+$, 340.

EXAMPLE 85

Preparation of
1-dimethylcarbamoyl-3-[2-(3-pyridinyl)thiazolid-4-oyl]-6-methoxyindole The desired compound was prepared according to the method of Example 36, except substituting 3-[2-(3-pyridinyl)-3-tert-butoxycarbonylthiazolid-4-oyl]-6-methoxyindole, prepared as in Example 82 for 3-[2-(3-pyridinyl)-3-tert-butoxycarbonylthiazolid-4-oyl]indole, and substituting dimethylcarbamoyl chloride for benzenesulfonyl chloride.

NMR (CDCl$_3$, 300 MHz): δ3.10–3.16 (6H), 3.36–3.58 (2H), 3.88 (3H), 4.58–4.72 (1H), 5.67–5.74 (0.5H), 5.97–6.00 (0.5H), 6.98–7.07 (2H), 7.29–7.38 (2H), 7.76–7.80 (0.5H), 7.84–7.88 (0.5H), 7.94 (0.5H), 8.00 (0.5H), 8.23–8.27 (1H), 8.50–8.63 (1H), 8.77–8.83 (1H). Mass Spectrum (DCI/NH$_3$): 410 (M+1)$^+$.

EXAMPLE 86

Preparation of
3-[2-(3-pyridinyl)-thiazolid-4-oyl]-6-phenylindole

Step 1. 1-Trimethylsilyl-2-(2-nitro-4-biphenyl)-acetylene.

4-Bromo-3-nitrobiphenyl (5.0 g, 18 mmol) was dissolved in triethylamine (50 mL). Catalytic phenothiazine was added and the solution was degassed by bubbling argon through the solution for 45 min. Bis(triphenylphosphine)palladium(II) chloride (0.068 g, 0.10 mmol) and trimethylsilyl acetylene (5.0 mL, 36 mmol) were then added and the yellow solution was heated at 75° C. for 4 hours during which time it became a brown suspension. The reaction mixture was cooled to ambient temperature, the solids were removed by filtration, and the filtrate concentrated in vacuo. The crude product (6.11 g) was used without further purification.

Step 2. 2-Nitro-4-biphenylacetaldehyde dimethyl acetal.

The material prepared as in Step 1 was dissolved in methanol (100 mL), and powdered KOH (5.6 g, 99 mmol) was added. The reaction mixture was heated at reflux for 17 hours. The solution was cooled to ambient temperature quenched with glacial acetic acid (6.0 mL), and concentrated in vacuo. The residue was partitioned between H$_2$O and methylene chloride. The organic phase was dried over MgSO$_4$, filtered, and concentrated in vacuo to give a brown oil. The crude material was purified by chromatography on silica gel to give 2-nitro-4-biphenylacetaldehyde dimethyl acetal, (4.22 g, 74% yield for steps 1 and 2).

Step 3. 2-Amino-4-biphenylacetaldehyde dimethyl acetal.

2-Nitro-4-biphenylacetaldehyde dimethyl acetal (3.85 g, 13.4 mmol) was reduced by catalytic hydrogenation using 5% palladium on carbon in 1% acetic acid/methanol. The material so obtained was used without further purification.

Step 4. 6-Phenylindole.

The material prepared as in Step 3 was dissolved in 1:1 ethanol, water (16 mL), and concentrated HCl (1.0 mL) was added. The reaction mixture was stirred for 17 hours at ambient temperature, during which time a light-brown precipitate formed. The precipitate was filtered off to give 6-phenylindole (0.56 g). The filtrate was extracted with methylene chloride. The organic extract was dried over MgSO$_4$, filtered, and as concentrated in vacuo to a brown foam. The foam was crystallized from ethanol to give 1.40 g of 6-phenylindole (total 1.96 g, 76% yield for steps 2-4).

Step 5. 3-[2-(3-pyridinyl)thiazolid-4-oyl]-6-phenylindole.

The desired compound was prepared according to the method of Example 20 except substituting 6-phenylindole for indole.

Melting Point: 180°-185° C. NMR (CDCl$_3$, 300 MHz): δ3.18 (dd, 0.4H, J=7.0, 10.7 Hz), 3.23 (dd, 0.6H, J=7.9, 10.3 Hz), 3.41 (dd, 0.4H, J=7.0, 10.7 Hz), 3.55 (dd, 0.6H, J=7.0, 10.3 Hz), 4.63 (t, 0.4H, J=7.0 Hz), 4.73 (dd, 0.6H, J=7.0, 7.9 Hz), 5.75 (s, 0.6H), 6.04 (s, 0.4H), 7.37 (m, 1H), 7.47 (m, 2H), 7.61 (m, 1H, 7.63 (m, 4H), 7.89 (m, 0.4h), 7.97 (m, 0.6H), 7.98 (d, 0.4H, J=3.3 Hz), 8.04 (d, 0.6H, J=2.9 Hz), 8.43 (s, 0.6H), 8.45 (s, 0.4H), 8.55 (dd, 0.4H, J=1.4, 4.8 Hz), 8.62 (dd, 0.6H, J=1.4, 4.8 Hz), 8.81 (d, 0.6H, J=2.6 Hz), 8.84 (br s, 1H), 8.86 (d, 0.4H, J=2.2 Hz). IR (KBr): 3420 (br), 3230 (sh), 2920, 1680, 1635, 1605, 1420, 1405, 1205. Mass Spectrum (DCI/NH$_3$): 386 [(M+1)$^+$, 60], 102 (100).

EXAMPLE 87

Preparation of 1-dimethylcarbamoyl-3-[2-(3-pyridinyl)thiazolid-4-oyl]-6-phenylindole The desired compound was prepared according to the method of Example 36 except substituting 3-[2-(3-pyridinyl)-3-tert-butoxycarbonylthiazolid-4-oyl]-6-phenylindole, prepared as in Example 86 for 3-[2-(3-pyridinyl)-3-tert-butoxycarbonylthiazolid-4-oyl]indole, and substituting dimethylcarbamoyl chloride for benzenesulfonyl chloride.

Melting Point: 91°-97° C. NMR (CDCl$_3$, 300 MHz): δ3.13 (s, 1.2H), 3.17 (s, 0.8H), 3.23 (m, 1H), 3.44 (dd, 0.4H, J=7.4, 10.3 Hz), 3.56 (dd, 0.6H, J=7.0, 10.3 Hz), 4.64 (t, 0.4H, J=7.4 Hz), 4.71 (dd, 0.6H, J=7.0, 7.3 Hz), 5.73 (s, 0.6H), 6.01 (s, 0.4H), 7.29 (m, 1H), 7.38 (m, 2H), 7.47 (m, 2H), 7.64 (m, 2H), 7.73 (br s 1H), 7.91 (m, 0.4H), 7.97 (m, 0.6H), 8.10 (s, 0.4H), 8.15 (s, 0.6H), 8.42 (d, 0.6H, J=2.2 Hz), 8.45 (d, 0.4H, J=2.2 Hz), 8.55 (dd, 0.4H, J=2.2, 4.2 Hz), 8.62 (dd, 0.6H, J=1.5, 4.8 Hz), 8.80 (d, 0.6H, J=2.2 Hz), 8.86 (d, 0.4H, J=1.9 Hz). IR (KBr): 3430, 2920, 1695, 1655, 1470, 1380, 1180. Mass Spectrum (DCI/NH$_3$): 457 [(M+1)$^+$, 100], 423 (60), 334 (35). Exact Mass: Theoretical: 457.169; Experimental: 457.169.

EXAMPLE 88

Preparation of 3-[2-(3-pyridinyl)thiazolid-4-oyl]-6-hydroxyindole

Step 1. 6-Tert-butyldimethylsilyloxyindole.

6-Hydroxyindole (0.419 g, 3.15 mmol), prepared as in Example 74, step 1, was dissolved in a mixture of methylene chloride (12 mL) and 2,6-lutidine (1.0 mL) and cooled in an ice-water bath. Tert-butyldimethylsilyl triflate (0.80 mL, 3.50 mmol) was added under N$_2$ and the reaction mixture was stirred for 2 min, after which the cold bath was removed and stirring was continued for a further 20 min. The reaction mixture was poured into a mixture of aqueous pH 7 buffer (25 mL), and methylene chloride (25 mL). The organic phase was dried over MgSO$_4$, filtered, and concentrated in vacuo to give the desired compound (0.679 g), which was used without further purification.

Step 2. 3-[2-(3-pyridinyl)-3-tert-butoxycarbonyl)-thiazolid-4-oyl]-6-tert-butyldimethylsilyloxyindole.

The desired compound was prepared according to the method of Example 20, steps 1 and 2, except substituting 6-tert-butyldimethylsilyloxyindole for indole.

Step 3. 3-[2-(3-pyridinyl)thiazolid-4-oyl]-6-tert-butyldimethylsilyloxyindole.

The desired compound was prepared according to the method of Example 36, step 2, except substituting 3-[2-(3-pyridinyl)-3-tert-butoxycarbonylthiazolid-4-oyl]-6-tert-butyldimethylsilyloxyindole for 1-phenylsulfonyl-3-[2-(3-pyridinyl)-3-tert-butoxycarbonylthiazolid-4-oyl]indole.

Step 4. 3-[2-(3-pyridinyl)thiazolid-4-oyl]-6-hydroxyindole.

3-[2-(3-pyridinyl)thiazolid-4-oyl]-6-tert-butyldimethylsilyloxyindole (55 mg, 0.12 mmol) was dissolved in tetrahydrofuran (2.0 mL) and cooled in an ice-water bath. Tetrabutylammonium fluoride (1.0M solution in tetrahydrofuran, 0.25 mL, 0.25 mmol) was added via syringe, and the reaction mixture was stirred for 1 hour. The reaction mixture was partitioned between ether and pH 7 aqueous buffer. The organic phase was dried over MgSO$_4$, filtered, and concentrated in vacuo to give 3-[2-(3-pyridinyl)thiazolid-4-oyl]-6-hydroxyindole (23 mg), as a yellow solid.

Melting Point: 203°-205° C. NMR (CDCl$_3$, 300 MHz): δ9.28 (s, 0.5H, OH), 9.25 (s, 0.5H, OH), 8.74 (d, 0.5H, J=1.1 Hz), 8.66 (d, 0.5H, J=1.3 Hz), 8.56 (dd, 0.5H, J=1.1, 4.8 Hz), 8.45 (d, 0.5H, J=1.3, 4.8 Hz), 8.40 (m, 1H), 8.03 (m, 0.5H), 7.98 (d, 0.5H, J=0.5 Hz), 7.95 (d, 0.5H, J=0.5 H), 7.86 (m, 0.5H), 7.44 (dd, 0.5H, J=4.8, 6.6 Hz), 7.36 (dd, 0.5H, J=4.4, 6.2 Hz), 6.84 (d, 0.5H, J=1.8 Hz). 6.82 (d, 0.5H, J=2.2 Hz), 6.73 (m, 1H), 6.71 (m, 0.5H), 5.99 (d, 0.5H, J=8.5 Hz), 5.68 (d, 0.5H, J=13.2 Hz), 4.78 (m, 1H), 3.49 (m, 1H), 3.03 (m, 0.5H, 2.96 (m, 0.5H) IR (KBr): 3440 (br), 2940, 2920, 1625, 1520, 1420. Mass Spectrum (DCI/NH$_3$): 326 [(M+1)$^+$, 100)]292 (40). Exact Mass: Theoretical: 326.096; Experimental: 326.097.

EXAMPLE 89

Preparation of 1-dimethylcarbamoyl-3-[2-(3-pyridinyl)thiazolid-4-oyl]-6-chloroindole Step 1. 3-[2,(3-pyridinyl)-3-tert-butoxycarbonylthiazolid-4-oyl]-6-chloroindole.

The desired compound was prepared according to the method of Example 20, steps 1 and 2, except substituting 6-chloroindole for indole.

Step 2. 1-dimethylcarbamoyl-3-[2-(3-pyridinyl)thiazolid-4-oyl]-6-chloroindole.

The desired compound was prepared according to the method of Example 36 except substituting 3-[2-(3-pyridinyl)-3-tert-butoxycarbonylthiazolid-4-oyl]-6-chloroindole, prepared as in step 1 for 3-[2-(3-pyridinyl)-3-tert-butoxycarbonylthiazolid-4-oyl]indole, and substituting dimethylcarbamoyl chloride for benzenesulfonyl chloride.

NMR (CDCl$_3$, 300 MHz): δ8.71 (m, 1H), 8.66 (s, 0.5H), 8.61 (s, 0.5H), 8.52 (dd, 0.5H, J=1.5, 2.7 Hz), 8.46 (dd, 0.5H, J=1.4, 2.8 Hz), 8.31 (d, 0.5H, J=2.7 Hz), 8.28 (d, 0.5H, J=2.8 Hz), 8.11 (m, 0.5H), 8.03 (m, 0.5H), 7.68 (d, 0.5H, J=1.5 Hz), 7.66 (d, 0.5H, J=1.4 Hz), 7.46 (m, 1H), 7.36(d, 0.5H, J=1.7 Hz), 7.31 (d, 0.5H, J=1.7 Hz), 5.92 (s, 0.5H), 5.73 (s, 0.5H), 4.91 (m, 1H), 3.61 (dd, 0.5H, J=7.0, 10.3 Hz), 3.53 (dd, 0.5H, J=7.3, 10.7 Hz), 3.24 (m, 1H), 3.12 (s, 3H), 3.09 (s, 3H). IR (CDCl$_3$): 3440, 2960, 1680, 1600, 1260, 1100. Mass Spectrum (DCI/NH$_3$): 415 [(M+1)$^+$, 100]. Exact Mass: Theoretical: 415.099; Experimental: 415.099.

EXAMPLE 90

Preparation of 3-[2-(3-pyridinyl)-3-formylthiazolid-4-oyl]indole 1-tert-butoxycarbonyl-3-[2-(3-pyridinyl)-3-formylthiazolid-4-oyl]indole (0.25 g, 0.56 mmol), prepared according to the method of Example 56, was dissolved in methylene chloride (2 mL) and cooled in an ice bath. Trifluoroacetic acid (18 mL) was added and the reaction mixture was stirred for 2 hours. The reaction mixture was concentrated in vacuo and the residue was partitioned between methylene chloride and saturated aqueous NaHCO$_3$. The organic phase was washed with brine, dried over MgSO$_4$, filtered, and concentrated in vacuo. The desired compound (0.14 g, 78%), was obtained by chromatography on silica gel.

NMR (CDCl$_3$, 300 MHz): δ3.00–3.35 (m, 2H), 5.33 (t, 0.25H), 5.40–5.60 (m, 0.75H), 5.90 (s, 0.5H), 6.08 (s, 0.5H), 6.14 (s, 0.5H), 6.30 (s, 0.5H), 7.10–7.40 (m, 4H), 7.70–7.90 (m, 1H), 8.00–8.30 (cm, 2H), 8.40 (m, 1H), 8.55 (d, 0.5H, 0.3 Hz), 8.63 (d, 0.25H, 0.3 Hz), 8.70 (s, 0.25H), 8.90 (d, 1H, 1.5 Hz). Mass Spectrum (DCI/NH$_3$): 338 (M+1)$^+$.

EXAMPLE 91

Preparation of 1-dimethylcarbamoyl-3-[2-(3-pyridinyl)-3-formylthiazolid-4-oyl]indole The desired compound was prepared according to the method of Example 56, except substituting 1-Dimethylcarbamolyl-3-[2-(3-pyridinyl)thiazolid-4-oyl]indole, prepared as in Example 38, for 1-tert-butoxycarbonyl-3-[2-(3-pyridinyl)thiazolid-4oyl]indole.

NMR (CDCl$_3$, 300 MHz): δ3.13 (s, 6H), 3.50 (m, 2H), 5.55 (t, 0.25H), 5.70 (t, 0.75H), 6.00 (dd, 0.25H, J=0.3, 0.9 Hz), 6.15 (s, 0.25H), 6.19 (s, 0.75H), 6.50 (bd, 0.25H), 7.40 (m, 3H), 7.53 (m, 1H), 7.85 (m, 0.25H), 7.98 (s, 0.25H), 8.15 (m, 0.25H), 8.26 (0.75H), 8.29 (s, 0.5H), 8.40 (m, 1.5H), 8.60 (m, 1H), 8.75 (d, 0.25H, J=0.3 Hz), 8.80 (d, 0.5H, J=0.3 Hz), 8.85 (d, 0.25H, J=0.3 Hz). Mass Spectrum (DCI/NH$_3$): 409 (M+1)$^+$.

EXAMPLE 92

Preparation of 1-(4-morpholinocarbonyl)-3-[2-(3-pyridinyl)-3-formylthiazolid-4-oyl]indole Step 1. 1-(4-morpholinocarbonyl)-3-[2-(3-pyridinyl)-thiazolid-4-oyl]indole.

The desired compound was prepared according to the method of Example 36, except substituting 4-morpholinecarbonyl chloride for benzenesulfonyl chloride.

Step 2. 1-(4-morpholinocarbonyl)-3-[2-(3-pyridinyl)-3-formylthiazolid-4-oyl]indole.

The desired compound was prepared according to the method of Example 56, except substituting 1-(4-morpholinocarbonyl-3-[2-(3-pyridinyl)thiazolid-4-oyl]indole, prepared as in step 1, for 1-tert-butoxycarbonyl-3-[2-(3-pyridinyl)thiazolid-4-oyl]indole.

NMR (CDCl$_3$, 300 MHz): δ3.40 –3.70 (m, 6H), 3.80 (t, 4H), 5.70 (t, 0.5H), 6.00 (q, 0.5H), 6.13 (s, 0.5H), 6.20 (s, 0.5H), 7.30–7.50 (m, 3H), 7.55–7.60 (m, 1H), 7.85 (m, 0.5H), 7.89 (s, 0.25H), 8.15 (d, 0.25H, J=0.6 Hz), 8.29 (d, 1H, J=0.6 Hz), 8.3–8.45 (m, 1H), 8.50–8.62 (m, 1H), 8.65–8.82 (m, 2H). Mass Spectrum (DCI/NH$_3$): 451 (M+1)$^+$.

EXAMPLE 93

Preparation of 1-dimethylcarbamoyl-3-[2-(3-pyridinyl)-3-formylthiazolid-4-oyl]-6-phenylmethoxyindole The desired compound was prepared according to the method of Example 56 except substituting 1-Dimethylcarbamoyl-3-[2-(3-pyridinyl)thiazolid-4-oyl]-6-phenylmethoxyindole, prepared as in Example 52, for 1-tert-butoxycarbonyl-3-[2-(3-pyridinyl)thiazolid-4-oyl]indole.

Melting Point: 90° C. NMR (CDCl$_3$, 300 MHz): δ3.00 (s, 3H), 3.38–3.65 (m, 2H), 5.15 (dd, 2H, J=3, 3 Hz), 5.65 (dd, 0.5H, J=6,6 Hz), 5.97 (dd, 0.5H, J=4, 9Hz), 6.13 (s, 0.4H, major rotomer of one diastereomer), 6.18 (s, 0.5H, major rotomer of other diastereomer), 6.45 (s, 0.11H, minor rotomer of one diastereomer), 6.50 (s, 0.7H, minor rotomer of other diastereomer), 7.05 (d, 1H, J=1 Hz), 7.10 (m, 1H), 7.30–7.50 (cm, 6H), 7.82 (dd, 0.5H, J=1 Hz), 7.95 (s, 0.25H), 8.00 (d, 0.25H, J=6 Hz), 8.12 (d, 1H, J=5 Hz), 8.20–8.32 (m, 1.5H), 8.40 (dt, 0.5H, J=1,9 Hz), 8.53 (m, 0.25H), 8.57 (dd, 0.25H, J=1, 6 Hz), 8.65 (dd, 0.5H, J=1, 6 Hz), 8.73 (d, 0.5H, J=2 Hz), 8.78 (0.5H, J=2 Hz). IR (CDCl$_3$): 1710, 1560, 1510, 1410. Mass Spectrum (DCI/NH$_3$): 515 (M+1)$^+$, 409, 381.

EXAMPLE 94

Preparation of 1-dimethylcarbamoyl-3-[2-(3-pyridinyl)-3-formylthiazolid-4-oyl]-6-methylindole Step 1. 1-Dimethylcarbamoyl-3-[2,(3-pyridinyl)thiazolid-4-oyl]indole.

The desired compound was prepared according to the method of Example 36 except substituting 3-[2-(3-pyridinyl)-3-tert-butoxycarbonylthiazolid-4-oyl]-6-methylindole, prepared as in Example 80 for 3-[2-(3-pyridinyl)-3-tert-butoxycarbonylthiazolid-4-oyl]indole, and substituting dimethylcarbamoyl chloride for benzenesulfonyl chloride.

Step 2. 1-Dimethylcarbamoyl-3-[2-(3-pyridinyl)-3,formylthiazolid-4-oyl]-6-methylindole.

The desired compound was prepared according to the method of Example 56 except substituting 1-Dimethylcarbamoyl-3-[2-(3-pyridinyl)thiazolid-4-oyl]-6-methylindole, prepared as in step 1, for 1-tert-butoxycarbonyl-3-[2-(3-pyridinyl)thiazolid-4-oyl]indole.

NMR (CDCl$_3$, 300 MHz): δ2.50 (s, 3H), 3.12 (s, 6H), 3.50 (m, 2H), 5.52 (t, 0.125H, J=0.6 Hz), 5.7 (t, 0.75H, J=0.6 Hz), 6.0 (q, 0.25H, J=0.3, 0.9 Hz), 6.15 (s, 0.375H), 6.19 (s, 0.375H), 6.49 (d, 0.125H), 7.20 (m, 1H), 7.35 (m, 2H), 7.80–8.10 (m, 1H), 8.15–8.35 (m, 2H), 8.40–8.55 (m, 1H), 8.60 (dd, 0.5H, J=0.3, 0.6 Hz), 8.67 (dd, 0.5H, J=0.3, 0.6 Hz), 8.75 (d, 0.5H, J=0.3 Hz), 8.78 (dd, 0.5H, J=0.3,0.5 Hz). Mass Spectrum (DCI/NH$_3$): 423 (M+1)$^+$.

EXAMPLE 95

Preparation of 1-dimethylcarbamoyl-3-[1-oxide,2-(3,pyridinyl)-3-formylthiazolid-4-oyl]indole 1-Dimethylcarbamoyl-3-[2-(3-pyridinyl)-3-formylthiazolid-4-oyl]-indole (128 mg, 0.30 mmol), prepared as in Example 91, was dissolved in methylene chloride (3.0 mL). Titanium(IV) isopropoxide (0.10 mL, 0.33 mmol) and H$_2$O (3.3×10$^{-3}$M in methylene chloride, 0.1 mL, 0.33 mmol) were added and the solution was cooled to −20° C. Tert-butyl hydroperoxide (5.5M in 2,2,4-trimethylpentane, 0.062 mL, 0.33 mmol) was added and the reaction mixture was stirred for 30 min at −20° C. The reaction mixture was quenched with H$_2$O (2.0 mL) and warmed to ambient temperature. Alumina was added and the reaction mixture was filtered. The filtrate was washed with brine, dried over Na$_2$SO$_4$, filtered, and concentrated in vacuo. The crude material was purified by chromatography on the Chromatatron (Al$_2$O$_3$; mm; 99:1 to 95:5 chloroform, methanol; 8 mL/min), to yield the desired material (34 mg).

NMR [(DMSO-d6, 300 MHz), 140° C.]: δ3.08 (s, 6H), 3.18 (dd, 1H, J=12,14 Hz), 3.78 (dd, 1H, J=6,14 Hz), 6.20 (m, 1H), 6.43 (br s, 1H), 7.30–7.45 (cm, 3H), 7.62 (dd, 1H, J=1,8 Hz), 8.15 (m, 1H), 8.25 (m, 1H), 8.55 (s, 2H), 8.75 (s, 1H), 8.95 (s, 1H). IR (film): 2900–3100-(weak), 1680, 1390, 1200, 1140, 1095, 1060, 750. Mass Spectrum (FAB): 425,286.

EXAMPLE 96

Preparation of trans-1-dimethylcarbamoyl-3-[2-(3-pyridinyl)-3-formylthiazolid-4-oyl]indole The desired compound remained as unreacted starting material in the reaction s described in Example 95, and was isolated by chromatography on Al$_2$O$_3$ as described in Example 95.

NMR (CDCl$_3$, 300 MHz): 75:25 ratio of diastereomers. Each diastereomer has a ca.2:1 ratio of rotomeric forms: δ3.10 (s, 6H), 3.40 (m, both rotomers of major diastereomer 0.75H), 3.50 (m, both rotomers of minor diastereomer 0.25H), 3.63 (dd, both rotomers of major diastereomer 0.75H, J=5, 12 Hz), 3.75 (dd, both rotomers of minor diastereomer 0.25H), 5.58 (m, minor rotomer of minor diastereomer 8%H), 5.70 (m, major rotomer of minor diastereomer 16% plus minor rotomer of major diastereomer 25%H=0.41H), 6.02 (dd, major rotomer of major diastereomer 50%H, J=8, 12 Hz), 6.15 (s, major rotomer of major diastereomer of minor diastereomer 16% plus minor rotomer of major diastereomer 25%H=0.41H), 6.02 (dd, major rotomer of major diastereomer 50%H, J=8, 12 Hz), 6.15 (s, major rotomer of major diastereomer 16%H), 6.42 (s, minor rotomer of major diastereomer 25%H), 6.47 (s, minor rotomer of major diastereomer 8%H), 7.20–7.55 (cm, 4H), 7.80 (dt, 1H, J=1, 2 Hz), 7.95 (s, 1H), 8.20–8.40 (m, 2H), 8.50–8 8.80 (br m, 2H). IR (CDCl$_3$): 1690, 1660. Mass Spectrum (FAB): 409.

EXAMPLE 97

Preparation of cis-1-Dimethylcarbamoyl-3-[2-(3-pyridinyl)-3-formylthiazolid-4-oyl]indole The desired compound was prepared according to the method of Example 91, except that the cis isomer was isolated by chromatography on the Chromatatron (SiO$_2$; 1 mm; 97:3 to 95:5 chloroform, methanol).

NMR (CDCl$_3$, 300 MHz): 3.6:1 ratio of rotomers: δ3.10 (s, 6H), 3.4–3.58 (m, 2H), 5.55 (dd, minor rotomer 0.22H, J=8, 9 Hz), 5.70 (dd, major rotomer 0.78H, J=6, 6 Hz), 6.18 (s, major rotomer 0.78H), 6.45 (s, minor rotomer 0.22H), 7.33–7.55 (cm, 4H), 8.10–8.45 (cm, 5H), 8.75–8.85 (cm, 1H). IR (CDCl$_3$): 1680 (br). Mass Spectrum (FAB): 409.

EXAMPLE 98

Preparation of 3-[2-(3-pyridinyl)-3-acetylthiazolid-4-oyl]indole

The desired compound was prepared according to the method of Example 90, except substituting 1-tert-butoxycarbonyl-3-[2-(3-pyridinyl)-3-acetylthiazolid-4-oyl]indole, prepared as in Example 57 for 1-tert-butoxycarbonyl-3-[2-(3-pyridinyl)-3-formylthiazolid-4-oyl]indole.

NMR (DMSO-d6, 300 MHz): δ1.90 (d, 3H, J=0.6 Hz), 3.00 (m, 0.5H), 3.18 (m, 0.5H), 3.60 (dd, 0.5H, J=0.35, 0.9 Hz), 3.70 (dd, 0.5H, J=0.35, 0.9 Hz), 5.65 (m, 0.5H), 5.95 (m, 0.5H), 6.49 (s, 0.25H), 6.63 (s, 0.75H), 7.20–7.53 (m, 4H), 8.20–8.30 (m, 1H), 8.39–8.55 (m, 2H), 8.68 (d, 0.5H, J=0.3 Hz), 8.7 (d, 0.5H, J=0.3 Hz), 8.93 (d, 0.25H, J=0.3 Hz), 9.05 (d, 0.75H, J=0.3 Hz). Mass Spectrum (DCI/NH$_3$): 352 (M+1)$^+$.

EXAMPLE 99

Preparation of 1-dimethylcarbamoyl-3-[2-(3-pyridinyl)-3-acetylthiazolid-4-oyl]-6-phenylmethoxyindole The desired compound was prepared according to the method of Example 57 except substituting 1-Dimethylcarbamoyl-3-[2-(3-pyridinyl)thiazolid-4-oyl]-6-phenylmethoxyindole, prepared as in Example 52, for 1-tert-butoxycarbonyl-3-[2-(3-pyridinyl)thiazolid-4-oyl]-6-phenylmethoxyindole.

NMR (CDCl$_3$, 300 MHz): δ2.00 (s, 3H), 3.01 (s, 6H), 3.40 (m, 2H), 5.15 (d, 2H, J=0.3 Hz), 5.60 (m, 1H), 6.18 (s, 1H), 7.05 (m, 2H), 7.30–7.50 (m, 6H), 8.12 (s, 1H), 8.28 (d, 1H, J=0.9 Hz), 8.57 (m, 2H), 8.85 (m, 1H). Mass Spectrum (DCI/NH$_3$): 529 (M+1)$^+$.

EXAMPLE 100

Preparation of 1-dimethylcarbamoyl-3-[2-(3-pyridinyl)-3-acetylthiazolid-4-oyl]indole The desired compound was prepared according to the method of Example 57 except substituting 1-Dimethylcarbamoyl-3-[2-(3-pyridinyl)thiazolid-4-oyl]indole, prepared as in Example 38, for 1-tert-butoxycarbonyl-3-[2-(3-pyridinyl)thiazolid-4-oyl]indole.

NMR (CDCl$_3$, 300 MHz): δ2.05 (s, 3H), 3.15 (s, 6H), 3.30 (m, 2H), 5.60 (m, 1H), 6.18 (s, 1H), 7.39 (cm, 3H), 7.53 (m, 1H), 8.25 (s, 1H), 8.40 (d, 1H, J=0.9 Hz), 8.60 (m, 2H), 8.85 (m, 1H) Mass Spectrum (DCI/NH$_3$): 4255 (M+1)$^+$.

EXAMPLE 101

Preparation of 1-dimethylcarbamoyl-3-[2-(3-pyridinyl)-3-acetyl-thiazolid-4-oyl]indole oxalate The desired compound was prepared according to the method of Example 3, except substituting 1-Dimethylcarbamoyl-3-[2-(3-pyridinyl)-3-acetylthiazolid-4-oyl]-6-phenylmethoxyindole, prepared as in Example 99, for 1-[2-(3-pyridinyl)thiazolid-4-oyl]indole.

NMR (CDCl$_3$, 300 MHz): δ2.02 (d, 3H, J=0.6 Hz), 3.02 (s, 6H), 3.15–3.62 (m, 2H), 5.15 (d, 2H, J=0.3 Hz), 5.60 (m, 0.75H), 5.96 (d, 0.25H, J=0.6 Hz), 6.18 (s, 0.5H), 6.29 (s, 0.25H), 6.55 (m, 0.25H), 7.00–7.10 (m, 2H), 7.30–7.65 (m, 6H), 8.00 (s, 0.5H), 8.12 (s, 0.5H), 8.25–8.30 (m, 1H), 8.50–8.63 (m, 2H), 8.80–8.90 (m, 1H). Mass Spectrum (DCI/NH$_3$): 529 (M+1)$^+$.

EXAMPLE 102

Preparation of 3-[2-(3-pyridinyl)-3-trifluoroacetylthiazolid-4-oyl]indole, isomer 1

Step 1. 1-tert-buxtoxycarbonyl-3-[2-(3-pyridinyl)-3-trifluoroacetylthiazolid-4-oyl]indole.

The desired compound was prepared according to the method of Example 56 except substituting trifluoroacetic anhydride for acetic formic anhydride.

Step 2. 3-[2-(3-pyridinyl)-3-trifluoroacetylthiazolid-4-oyl]indole, isomer 1.

The desired compound was prepared according to the method of Example 90 except substituting the material obtained as in step 1 for 1-tert-butoxycarbonyl-3-[2-3-pyridinyl)-3-formylthiazolid-4-oyl]indole. Chromatography on silica gel (98:2, then 95:5 chloroform, methanol) resolved the crude product into 2 sets of stereoisomers of unknown absolute stereochemistry.

Isomer 1; NMR (DMSO-d6): δ3.50 (m, 1H), 3.75 (m, 1H), 3.94 (m, 1H), 5.85 (m, 0.75H), 6.15 (m, 0.25H), 6.45 (s, 0.25H), 6.90 (s, 0.75H), 7.20–7.30 (m, 2H), 7.44–7.55 (m, 2H), 8.25 (m, 1H), 8.35 (m, 1H), 8.53 (m, 1H), 8.70 (s, 0.25H), 8.78 (s, 0.75H), 8.97 (d, 0.25H, J=0.3 Hz), 8.96 (d, 0.75H, J=0.3 Hz). Mass Spectrum (DCI/NH$_3$): 406 (M+1)$^+$.

EXAMPLE 103

Preparation of 3-[2-(3-pyridinyl)-3-trifluoroacetylthiazolid-4-oyl]indole, isomer 2.

The desired compound was isolated from the chromatography described in Example 102, step 2.

Isomer 2; NMR (DMSO-d6): δ3.52 (m, 1H), 3.70 (m, 1H), 3.90 (m, 1H), 6.45 (m, 1H), 6.60 (s, 0.75H), 6.89 (bs, 0.25H), 7.20–7.30 (m, 2H), 7.40–7.57 (m, 2H), 7.82 (d, 1H, J=0.65 Hz), 8.17 (d, 1H, J=0.66 Hz), 8.50–8.68 (m, 3H). Mass Spectrum (DCI/NH$_3$): 406 (M+1)$^+$.

EXAMPLE 104

Preparation of cis-1-dimethylcarbamoyl-3-[2-(3-pyridinyl)-3-trifluoroacetylthiazolid-4-oyl]indole The desired compound was prepared according to the method of Example 56 except substituting 1-Dimethylcarbamoyl-3-[2-(3-pyridinyl)thiazolid-4-oyl]indole, prepared as in Example 38 for 1-tert-butoxycarbonyl-3-[2-(3-pyridinyl)thiazolid-4oyl]indole, and trifluoroacetic anhydride for acetic formic anhydride. Chromatography on silica gel (50%, then 70% ethyl acetate, hexane; then ethyl acetate) afforded the cis isomer.

EXAMPLE 105

Preparation of cis-1-dimethylcarbamoyl-3-[2-(3-pyridinyl)-3-trifluoroacetylthiazolid-4-oyl]indole oxalate The desired Compound was prepared according to the method of Example 3, except substituting cis 1-dimethylcarbamoyl-3-[2-(3-pyridinyl)-3-trifluoroacetyl-thiazolid-4-oyl]indole, prepared as in Example 104, for 1-[2-(3-pyridinyl)thiazolid-4-oyl]indole.

NMR (CDCl$_3$, 300 MHz): δ3.10 (s, 6H), 3.45 (dd, 1.5H, J=0.6, 2.4 Hz), 3.72 (m, 0.5H), 5.65 (q, 0.75H, J=0.6, 0.9 Hz), 5.85 (m, 0.25H), 6.32 (s, 0.25H), 6.50 (s, 0.75H), 7.38 (m, 3H), 7.52 (m, 1H), 8.15 (s, 0.25H), 8.29 (s, 0.75H), 8.40 (m, 2H), 8.59 (d, 1H, J=0.3 Hz), 8.90 (m, 1H) Mass Spectrum (DCI/NH$_3$): 477 (M+1)$^+$.

EXAMPLE 106

Preparation of trans-1-dimethylcarbamoyl-3-[2-(3-pyridinyl)-3-trifluoroacetylthiazolid-4-oyl]indole The trans isomer was obtained from the chromatography described in Example 104.

EXAMPLE 107

Preparation of trans-1-dimethylcarbamoyl 1-34 2-(3-pyridinyl)-3-trifluoroacetylthiazolid-4-oyl]indole oxalate The desired compound was prepared according to the method of Example 3, except substituting trans-1-dimethylcarbamoyl-3-[2-(3-pyridinyl)-3-trifluoroacetyl-thiazolid-4-oyl]indole, prepared as in Example 106, for 1-[2-(3-pyridinyl)thiazolid-4-oyl]indole.

NMR (CDCl$_3$, 300 MHz): δ3.15 (s, 6H), 3.50 (m, 1.5H), 3.90 (m, 0.5H), 6.13 (m, 1H), 6.55 (bs, 0.5H), 6.64 (bs, 0.5H), 7.40 (bm, 3H), 7.53 (m, 1H), 7.70 (m, 1H), 8.35 (bd, 2H), 8.55 (bs, 2H). Mass Spectrum (DCI/NH$_3$): 477 (M+1)$^+$.

EXAMPLE 108

Preparation of 1-dimethylcarbamoyl-3-[2-(3-pyridinyl)-3-trifluoroacetylthiazolid-4-oyl]-6-phenylmethoxyindole, isomer 1

The desired compound was prepared according to the method of Example 56 except substituting 1-Dimethylcarbamoyl-3-[2-(3-pyridinyl)thiazolid-4-oyl]-6-phenylmethoxyindole, prepared as in Example 52, for 1-tert-butoxycarbonyl-3-[2-(3-pyridinyl)thiazolid-4-oyl]indole, and trifluoroacetic anhydride for acetic formic anhydride. Chromatography on silica gel (2:3, then 3:2 ethyl acetate, hexane; then ethyl acetate), resolved the crude product into two sets of isomers of unknown absolute stereochemistry.

Isomer 1; NMR (CDCl$_3$, 300 MHz) δ3.20 (s, 5.5H), 3.25 (m, 1H), 3.45 (m, 1.25H), 3.72 (m, 0.25H), 5.15 (m, 2H), 5.60 (dd, 0.75H, J=0.6, 0.9 Hz), 5.80 (m, 0.25H), 6.35 (s, 0.25H), 6.50 (s, 0.75H), 7.02 (d, 1H, J=0.3 Hz), 7.10 (m, 1.5H), 7.40 (m, 5.5H), 7.96 (s, 0.25H), 8.10 (s, 0.75H), 8.25 (m, 1H), 8.45 (m, 1H), 8.60 (bd, 1H), 8.90 (bd, 1H). Mass Spectrum (DCI/NH$_3$): 583 (M+1)$^+$.

EXAMPLE 109

Preparation of 1-dimethylcarbamoyl-3-[2-[3-pyridinyl)-3-trifluoroacetylthiazolid-4-oyl]-6-phenylmethoxyindole, isomer 2

The desired compound was isolated from the chromatography described in Example 108.

Isomer 2; NMR (CDCl$_3$, 300 MHz): δ3.10 (s, 6H), 3.30 (m, 0.5H), 3.50 (m, 1H), 3.92 (m, 0.5H), 5.15 (s, 2H), 5.95 (m, 1H), 6.55 (m, 1H), 7.00 (d, 1H, J=0.3 Hz), 7.10 (m, 1.5H), 7.30–7.49 (m, 5.5H), 7.60 (m, 1H), 8.02 (m, 1H), 8.22 (m, 1H), 8.58 (m, 2H). Mass Spectrum (DCI/NH$_3$): 583 (M+1)$^+$.

EXAMPLE 110

Preparation of 1-dimethylcarbamoyl-3-[2-(3-pyridinyl)-3-carbamoylthiazolid-4-oyl]indole The desired compound was prepared according to the method of Example 56 except substituting 1-Dimethylcarbamoyl-3-[2-(3-pyridinyl)thiazolid-4-oyl]indole, prepared as in Example 38 for 1-tert-butoxycarbonyl-3-[2-(3-pyridinyl)thiazolid-4-oyl]indole, and trimethylsilyl isocyanate for acetic formic anhydride.

NMR (CDCl$_3$, 300 MHz): δ3.13 (s, 6H), 3.32 (dd, 1H, J=9, 12 Hz), 3.42 (dd, 1H, J=6, 12 Hz), 4.35 (br s, 2H), 5.70 (dd, 1H, J=6, 9 Hz), 6.10 (s, 1H), 7.35–7.45 (cm, 3H), 7.53 (m, 1H), 8.25 (s, 1H), 8.43 (m, 1H), 8.55 (dt, 1H, J=1, 8 Hz), 8.60 (dd, 1H, J=5, 5 Hz), 8.82 (d, 1H, J=2 Hz). IR (CDCl3): 1690, 1670, 1390. Mass Spectrum (DCI/NH$_3$): 424, 381, 114. Exact Mass: Theoretical: 424.144; Experimental: 424.142.

EXAMPLE 111

Preparation of 1-dimethylcarbamoyl-3-[2-(3-pyridinyl)-3-carbamoylthiazolid-4-oyl]-6-phenylmethoxyindole The desired compound was prepared according to the method of Example 56 except substituting 1-Dimethylcarbamoyl-3-[2-(3-pyridinyl)thiazolid-4-oyl]-6-phenylmethoxyindole, prepared as in Example 52 for 1-tert-butoxycarbonyl-3-[2-(3-pyridinyl)thiazolid-4-oyl]-indole, and trimethylisocyanate for acetic formic anhydride.

NMR (CDCl$_3$, 300 MHz): δ3.00 (s, 6H), 3.30 (dd, 1H, J=8, 12 Hz), 3.40 (dd, 1H, J=6, 12 Hz), 4.40 (br s, 2H), 5.15 (d, 2H, J=2 Hz), 5.65 (dd, 1H, J=6, 8 Hz), 6.10 (s, 1H), 7.05 (m, 2H), 7.35–7.50 (cm, 6H), 8.15 (s, 1H), 8.28 (d, 1H, J=9 Hz), 8.50–8.60 (cm, 2H), 8.80 (br s, 1H). IR (CDCl3): 1690 (br), 1730 (w), 1780 (w). Mass Spectrum (DCI/NH$_3$): 530, 487,453.

EXAMPLE 112

Preparation of 1-dimethylcarbamoyl-3-[2-(3-pyridinyl)-3-methylsulfonylthiazolid-4-oyl]indole 1-Dimethylcarbamoyl-3-[2-(3-pyridinyl)thiazolid-4-oyl]indole (50 mg, 0.13 mmol), prepared as in Example 38, was dissolved in methylene chloride (1.0 mL) and cooled to −20° C. Triethylamine (0.09 mL, 0.66 mmol) and methanesulfonyl chloride (0.03 mL, 0.39 mmol) were added, the cold bath was removed, and the reaction mixture was stirred for 17 hours at ambient temperature. The reaction mixture was washed with saturated aqueous NaHCO$_3$ and brine, dried over MgSO$_4$, filtered, and concentrated in vacuo. The crude material was purified by chromatography on silica gel to afford the desired product (24 mg).

NMR (CDCl$_3$, 300 MHz): δ2.80 (s, 3H), 3.15 (s, 6H), 3.50 (dd, 1H, J=0.6, 0.9 Hz), 3.65 (dd, 1H, J=0.6, 0.9 Hz), 5.70 (t, 1H, J=0.6, 0.9 Hz), 6.35 (s, 1H), 7.30–7.43 (m, 3H), 7.56 (m, 1H), 8.28 (m. 3H), 8.50 (m, 1H), 8.90 (m, 1H). Mass Spectrum (DCI/NH$_3$): 459 (M+1)$^+$.

EXAMPLE 113

Preparation of 1-dimethylcarbamoyl-3-[2-(3-pyridinyl)-3,formyloxazolid-4-oyl]indole Step 1. 2-(3-pyridinyl)-4-oxazolidinecarboxylate methyl ester.

L-Serine methyl ester hydrochloride (10 g, 64 mmol) was suspended in methylene chloride (645 mL). Triethylamine (7.2 g, 71 mmol) was added and the mixture was stirred until a clear solution was obtained. 3-Pyridinecarboxaldehyde (6.9 g, 64 mmol) was added, and the clear solution was stirred at reflux for 8 hours. Water was removed azeotropically by means of a Dean-Stark trap filled with 3A molecular sieves. The reaction mixture was cooled to ambient temperature, washed twice with saturated aqueous NaHCO$_3$, dried over MgSO$_4$, filtered, and concentrated in vacuo to afford the desired compound.

Step 2. 2-(3-pyridinyl)-3-tert-butoxycarbonyl-4-oxazolidinecarboxylate methyl ester 2-(3-Pyridinyl)-4-oxazolidinecarboxylate methyl ester (9.2 g, 48 mmol), prepared as in step 1, was dissolved in methylene chloride (75 mL). A solution of di-tert-4-butyldicarbonate (16 g, 72 mmol) in methylene chloride (25 mL) was added followed by 4-dimethylaminopyridine (58 mg, 4.8 mmol). The resulting orange solution was stirred 17 hours at ambient temperature. The reaction mixture was concentrated in vacuo to give an orange solid. The crude material was purified by chromatography on silica gel to give 2-(3-pyridinyl)-3-tert-butoxycarbonyl-4-oxazolidinecarboxylate methyl ester (1.5 g, 10%).

Step 3. 2-(3-pyridinyl)-3-tert-butoxycarbonyl-4-oxazolidinecarboxylic acid.

The ester was hydrolyzed according to the method of Example 26, step 3 except substituting 2-(3-pyridinyl)-3-tert-butoxycarbonyl-4-oxazolidinecarboxylate methyl ester for methyl 2-(3-pyridinyl)-4-dithiolanecarboxylate.

Step 4. 2-(3-pyridinyl)-3-tert-butoxycarbonyl-4-oxazolidinecarboxyl chloride.

A solution of 2-(3-pyridinyl)-3-tert-butoxycarbonyl-4-oxazolidinecarboxylic acid (1.31 g, 4.45 mmol) in benzene (3 ml) and methylene chloride (9 mL), was added dropwise to a suspension of sodium hydride (0.11 g, 44.5 mmol) in benzene (25 mL). Dimethylformamide (47.5 mg, 0.65 mmol) was added and the yellow suspension was cooled in an ice bath. Oxalyl chloride 0.39 mL, 44.5 mmol) was added dropwise and the reaction mixture was stirred for 10 min in the ice bath and 40 min at ambient temperature. The orange-brown suspension was cooled in the ice bath and carried on without further purification.

Step 5. 3-[2-(3-pyridinyl)-3-tert-butoxycarbonyloxazolid-4-oyl]indole.

A solution of indole (521 mg, 44.5 mmol) in benzene (17 mL) was added dropwise to methylmagnesium bromide (3.0M in ether, 1.48 mL, 44.5 mmol) in an ice bath. The resulting suspension was stirred in the ice bath for 30 min and at ambient temperature for 1 hour. The suspension was cooled in the ice bath and transferred via cannula into the acid chloride suspension obtained in step 4. The cold bath was removed and the suspension stirred for 2 hours at ambient temperature. The reaction mixture was quenched with $H_2O$ (10 mL), then partitioned between $H_2O$ and ethyl acetate. The aqueous phase was extracted with ethyl acetate. The combined organic extracts were dried over $Na_2SO_4$, filtered, and concentrated in vacuo. The desired compound was obtained (308 mg), from chromatography on silica gel.

Step 6. 1-Dimethylcarbamoyl-3-[2-[3-pyridinyl)oxazolid-4-oyl]indole.

The desired compound was prepared according to the method of Example 36, except substituting 3-[2-(3-pyridinyl)-3-tert-butoxycarbonyloxazolid-4-oyl]-indole, prepared as in step 5 for 3-[2-(3-pyridinyl)-3-tert-butoxycarbonylthiazolid-4-oyl]-indole, and substituting dimethylcarbamoyl chloride for benzenesulfonyl chloride.

Step 7. 1-Dimethylcarbamoyl-3-[2-(3-pyridinyl)-3-formyloxazolid-4-oyl]indole.

The desired compound was prepared according to the method of Example 56, except substituting 1-Dimethylcarbamoyl-3-[2-(3-pyridinyl)oxazolid-4-oyl]indole, prepared as in step 6 for 1-tert-butoxycarbonyl-3-[2-(3-pyridinyl)thiazolid-4-oyl]indole.

Melting Point: 161.5°–163.5° C. NMR ($CDCl_3$, 300 MHz): $\delta$3.11 (bs, 6H), 4.20–4.45 (c, 1H), 4.57–4.68 (c, 1H), 5.35–5.50 (c, 0.75H), 5.60–5.67 (c, 0.25H), 6.11 (bs, 0.75H), 6.40 (s, 0.25H), 7.30–7.56 (c, 4H), 8.03–8.16 (c, 1H), 8.21–8.30 (c, 1H), 8.31–8.45 (c, 2H), 8.68–8.90 (c, 2H). IR (KBr): 3440,1680,1530,1490,1480,1450,1390,1200,1140,1100,75-5,710. Mass Spectrum ($DCI/NH_3$): 393 (M+1)+, 223, 125, 108.

EXAMPLE 114

Preparation of [2-(3-pyridinyl)thiazolid-4-yl](1-tert-butoxycarbonylindol-3-yl)methanol Step 1. Methyl-2-(3-pyridinyl)-3-tert-butoxycarbonyl-4-thiazolidinecarboxylate.

2-(3-pyridinyl)-3-tert-butoxycarbonyl-4-thiazolidinecarboxylic acid (78 g, 251 mmol), prepared as in Example 1, step 2, and 4-methylmorpholine (43 g, 427 mmol) were dissolved in tetrahydrofuran (500 mL), and cooled in the ice bath. Isobutylchloroformate (38 g, 276 mmol) was added and the yellow suspension was stirred for 0.5 hours. Methanol (250 mL) was added, the cold bath was removed, and the reaction mixture was stirred for 60 hours at ambient temperature. The reaction mixture was concentrated in vacuo and the residue was partitioned between ethyl acetate and saturated aqueous $NaHCO_3$. The aqueous phase was extracted twice with ethyl acetate. The combined organic extracts were washed twice with brine, dried over $MgSO_4$, filtered, and concentrated in vacuo. The crude product was purified by chromatography on silica gel to give Methyl-2-(3-pyridinyl)-3-tert-butoxycarbonyl-4-thiazolidinecarboxylate (38 g).

Step 2. 2-(3-pyridinyl)-3-tert-butoxycarbonyl-4-thiazolidinecarboxaldehyde.

A solution of Methyl-2-(3-pyridinyl)-3-tert-butoxycarbonyl-4-thiazolidinecarboxylate (10 g, 31 mmol) in methylene chloride (150 mL) was cooled to $-78°$ C. Diisobutylaluminium hydride (1M solution in methylene chloride, 93 mL, 93 mmol) was added in a stream. The reaction mixture was stirred for 1 hour at $-78°$ C., then quenched with saturated aqueous $NH_4Cl$ and warmed to ambient temperature. Cold aqueous 2M NaOH solution was added until a clear, 2-phase mixture was obtained. The mixture was extracted twice with ethyl acetate. The combined organic extracts were washed twice with brine, dried over $MgSO_4$, filtered, and concentrated in vacuo. The crude product was purified by chromatography on silica gel to give the desired compound (6.2 g, 68%).

Step 3. [2-(3-pyridinyl)-3-tert-butoxycarbonyl-4-thiazolid-4-yl](1-tert-butoxycarbonylindol-3-yl)methanol.

A solution of 1-tert-butoxycarbonyl-3-bromoindole (1.42 g, 4.8 mmol) in tetrahydrofuran (25 mL) was cooled to $-78°$ C. Tert-butyllithium (1.7M in pentane, 5.6 mL, 9.6 mmol) was added quickly dropwise and the clear yellow solution was stirred for 15 min. A 2-phase mixture of magnesium bromide etherate (1.24 g, 4.8 mmol) in ether (10 mL) was added quickly and the cloudy yellow solution was stirred for 15 min at $-78°$ C. A solution of 2-(3-pyridinyl)-3-tert-butoxycarbonyl-4-thiazolidinecarboxaldehyde, prepared as in step 2, in tetrahydrofuran (10 mL) was added dropwise, and the reaction mixture was warmed from $-78°$ C. to 0° C. over 3 hours. The reaction mixture was quenched with saturated aqueous $NH_4Cl$, warmed to ambient temperature, and partitioned between $H_2O$ and ethyl acetate. The aqueous phase was extracted with ethyl acetate. The combined organic layers were washed with brine, dried over $MgSO_4$, filtered, and concentrated. The crude material was chromatographed on silica gel to yield pure[2-(3-pyridinyl)-3-tert-butoxycarbonyl-4-thiazolid-4-yl](1-tert-butoxycarbonylindol-3-yl)methanol.

Step 4. [2-(3-pyridinyl)thiazolid-4-yl](1-tert-butoxycarbonylindol-3-yl)methanol.

A solution of [2-(3-pyridinyl)-3-tert-butoxycarbonyl-4-thiazolid-4-yl](1-tert-butoxycarbonylindol-3-yl)methanol, prepared as in step 3, in dioxane (5 mL), was added to HCl/dioxane (4M, 25 mL) at 0° C. The reaction mixture was stirred for 5 hours at 0° C., then quenched with saturated aqueous $NaHCO_3$. The resulting solution was saturated with solid $NaHCO_3$ and extracted twice with ethyl acetate. The combined organic extracts were washed twice with brine, dried over $MgSO_4$, filtered, and concentrated. Chromatography on silica gel afforded the desired product.

NMR ($CDCl_3$, 300 MHz): $\delta$1.57 (bs, 2H), 1.69 (s, 7H), 2.38–2.48 (bs, 1H), 2.89–3.06 (m, 1H), 3.26 (m, 1H), 3.60–3.90 (c, 2H), 4.91 (d, 0.125H, J=9.0 Hz), 5.05 (d, 0.125H, J=9.0 Hz), 5.39 (d, 0.25H, J=4.5 Hz), 5.52 (d, 0.5H, J=4.5 Hz), 5.62 (s, 0.5H), 5.64 (s, 0.125H), 5.71 (s, 0.125H), 5.78 (s, 0.25H), 7.22–7.40 (c, 3H), 7.56–7.75 (c, 2H), 7.79 (m, 0.33H), 7.88 (dt, 0.67H, J=9.0, 3.0 Hz), 8.17 (m, 1H), 8.50 (dd, 0.33H, J=6.0, 1.5 Hz), 8.57 (dd, 0.67H, J=6.0, 1.5 Hz), 8.75 (d, 0.67H, J=3.0 Hz), 8.78 (d, 0.33H, J=3.0 Hz). Mass Spectrum ($DCI/NH_3$): 412 (M+1)+.

EXAMPLE 115

Preparation of 2-[2-(3-pyridinyl)thiazolid-4-oyl]indole

Step 1. 1-Phenylsulfonylindole.

Sodium Hydride (4.8 g, 200 mmol) was suspended in tetrahydrofuran (120 mL) and the mixture was cooled in an ice bath. Dimethylsulfoxide (40 mL) was added, followed by a solution of indole (23.4 g, 200 mmol) in tetrahydrofuran (80 mL) and dimethylsulfoxide (40 mL). The cold bath was removed and the reaction mixture was warmed to ambient temperature. The cold bath was replaced and a solution of benzenesulfonyl chloride in tetrahydrofuran (160 mL) was added dropwise. The cold bath was removed and the reaction mixture was stirred overnight at ambient temperature. The reaction mixture was quenched with methanol and concentrated in vacuo to give a thick brown oil which was crystallized from methanol to give 1-phenylsulfonylindole (34.2 g, 66%).

Step 2. 1-Phenylsulfonyl-2-[2-[3-pyridinyl)-3-tert-butoxycarbonylthiazolid-4-oyl]-indole.

A solution of lithium diisopropylamide (21 mmol) in tetrahydrofuran (30 mL) was cooled to −78° C. and added via cannula to a solution of 1-phenylsulfonylindole (5.0 g, 19 mmol), prepared as in step 1, in tetrahydrofuran (50 mL) at −78° C. The reaction mixture was warmed slowly to −5° C. and was then cannulated into a solution of 2-(3-pyridinyl)-3-tert-butoxycarbonyl-4-thiazolidinecarboxyl chloride (31 mmol), prepared as in Example 20 step 1, at −78° C. The brown solution was warmed to ambient temperature and stirred for 17 hours. The reaction mixture was quenched with 10% aqueous citric acid and the layers were separated. The organic phase was washed 3 times with 10% aqueous citric acid solution, twice with saturated aqueous NaHCO$_3$, dried over Na$_2$SO$_4$, filtered, and concentrated in vacuo. The crude product was purified by chromatography on silica gel to give 1-phenylsulfonyl-2-[2-(3-pyridinyl)-3-tert-butoxycarbonylthiazolid-4-oyl]indole (604 mg)

Step 3. 2-[2-(3-pyridinyl)-3-tert-butoxycarbonylthiazolid-4-oyl]indole.

1-Phenylsulfonyl-2-[2-(3-pyridinyl)-3-tert-butoxycarbonylthiazolid-4-oyl]indole (600 mg, 1.1 mmol), prepared as in step 2, was dissolved in 30% aqueous methanol (20 mL) and 50% aqueous NaOH solution (2.0 mL, 23 mmol) was added. The reaction mixture was stirred for 8 hours at ambient temperature. The reaction mixture was concentrated in vacuo and the residue was partitioned between aqueous 1M NaOH and methylene chloride. The aqueous phase was extracted with methylene chloride. The combined organic extracts were washed with brine, dried over Na$_2$SO$_4$, filtered, and concentrated in vacuo. The desired product was purified by chromatography on silica gel.

Step 4. 2-[2-(3-pyridinyl)thiazolid-4-oyl]indole.

The desired compound was prepared according to the method of Example 36, step 2, except substituting 2-[2-(3-pyridinyl)-3-tert-butoxycarbonylthiazolid-4-oyl]indole for 1-Phenylsulfonyl-3-[2-(3-pyridinyl)-3-tert-butoxycarbonylthiazolid-4-oyl]indole Melting Point: 142.2°–144.0° C. NMR (CDCl$_3$, 300 MHz): δ3.11–3.23 (c, 1H), 3.36–3.56 (c, 1H), 4.27–4.42 (c, 0.67H), 4.50–4.58 (c, 0.33H), 4.78–4.92 (c, 1H), 5.72 (s, 0.67H), 6.00 (s, 0.33H), 7.12–7.22 (c, 1H), 7.31–7.51 (c,4H), 7.68–7.77 (c, 1H), 7.91–7.97 (c, 0.5H), 7.99–8.05 (c, 0.5H), 8.44–8.53 (c,1H), 8.55–8.62 (c, 1H), 8.76 (d, 1H, J=1.5 Hz). IR (CDCl$_3$): 710,740,750,800,1030,1040,130,1320,1340,1420,1520,1570,1620,1650,3440. Mass Spectrum (DCI/NH$_3$): 310 (M+1)+, 308, 306, 276, 147, 133, 107.

EXAMPLE 116

Preparation of 1-(N,N-dimethylcarbamoylmethyl)-3-[2-(3-pyridinyl)-thiazolid-4-oyl]indole Step 1. 3-[2-(3-pyridinyl)-3-tert-butylcarbonylthiazolid-4-oyl]indole.

Ethylmagnesium bromide (3.0M in ether, 10.7 mL, 32.1 mmol) was added to a solution of indole (3.77 g, 32.1 mmol) in ether (100 mL). The cloudy yellow-green solution was stirred for 15 min at ambient temperature, then zinc chloride (1.0M in ether, 32.2 ml, 32.2 mmol) was added and the resulting heterogeneous solution was stirred for 0.5 hour at ambient temperature. A solution of 2-(3-pyridinyl)-3-tert-butoxycarbonyl-4-thiazolidinecarboxyl chloride (16.1 mmol) in methylene chloride (80 mL), prepared according to the method of Example 20, step 1, was added quickly and the reaction mixture was stirred for 2 hours at ambient temperature. The reaction mixture was poured into saturated aqueous NH$_4$Cl solution and extracted twice with methylene chloride. The aqueous phase was made basic by addition of saturated aqueous NaHCO$_3$ and extracted twice with methylene chloride. The combined organic extracts were dried over MgSO$_4$, filtered, and concentrated in vacuo. Chromatography on silica gel gave 3-[2-(3-pyridinyl)-3-tert-butylcarbonylthiazolid-4-oyl]indole (3.15 g, 48% ).

Step 2. 1-(N,N-Dimethylcarbamoylmethyl)-3-[2-(3-pyridinyl)thiazolid-4-oyl]indole.

The desired compound was prepared according to the method of Example 60, except substituting N,N-dimethylchloroacetamide for ethyl chloroacetate.

NMR (CDCl$_3$, 300 MHz): δ3.02 (d, 3H, J=0.9 Hz), 3.20 (m, 4H), 3.40 (q, 1H, J=0.6, 0.9 Hz), 3.53 (q, 1H, J=0.6, 0.9 Hz), 4.57 (m, 0.5H), 4.68 (m, 1H), 4.98 (d, 2H, J=0.9 Hz), 5.70 (s, 0.6H), 6.02 (s, 0.4H), 7.30 (m, 4H), 7.88 (s, 1H), 7.98 (m, 1H), 8.40 (m, 1H), 8.53 (m, 0.5H), 8.60 (m, 0.5H), 8.82 (m, 1H) Mass Spectrum (DCI/NH$_3$): 395(M+1)+.

EXAMPLE 117

Preparation of 1-(N-methylcarbamoylmethyl)-3-[2-(3-pyridinyl)-thiazolid-4-oyl]indole The desired compound was prepared according to the method of Example 60, except substituting N-methylchloroacetamide for ethyl chloroacetate.

NMR (CDCl$_3$, 300 MHz): δ2.78 (d, 3H, J=0.6 Hz), 3.20 (m, 2H), 3.40 (dd, 0.5H, J=0.6, 1.2 Hz), 3.53 (dd, 0.5H, J=0.6, 1.2 Hz), 4.60 (t, 0.37H, J=0.6, 1.2 Hz), 4.69 (t, 0.63H, J=0.6, 1.2 Hz), 4.85 (d, 2H, J=1.5 Hz), 5.50 (m, 1H), 5.73 (s, 0.6H), 6.00 (s, 0.4H), 7.25–7.45 (m, 4H), 7.85 (m, 1H), 7.95 (m, 1H), 8.40 (m, 1H), 8.50 (dd, 0.4H, J=0.3, 0.6 Hz), 8.58 (dd, 0.6H, J=0.3, 0.6 Hz), 8.75 (d, 0.6H, J=0.3 Hz), 8.84 (d, 0.4H, J=0.3 Hz). Mass Spectrum (DCI/NH$_3$): 381(M+1)+.

EXAMPLE 118

Preparation of 1-carbomethoxyethyl-3-[2-(3-pyridinyl)thiazolid-4-oyl]indole

The desired compound was prepared according to the method of Example 60, except substituting methyl acrylate for ethyl chloroacetate.

NMR (CDCl$_3$, 300 MHz): δ2.90 (m, 2H), 3.15 (m, 1H), 3.35–3.60 (m, 2H), 3.65 (s, 1H), 3.70 (s, 2H), 4.50–4.70 (m, 3H), 5.72 (s, 0.62H), 6.03 (s, 0.38H), 7.30–7.4 (m, 4H), 7.85–8.05(m, 2H),8.40(m, 1H),8.53(dd, 0.41H, J=0.3, 0.6Hz),8.62(dd, 0.59H, J=0.3, 0.6 Hz), 8.80 (d, 0.59H, J=0.3 Hz), 5.85 (d, 0.41H, J=0.3 Hz). Mass Spectrum (DCI/NH$_3$): 396(M+1)$^+$.

EXAMPLE 119

Preparation of 1-carboxyethyl-3-[2-(3-pyridinyl)thiazolid-4-oyl]indole

Step 1. 1-Carbomethoxyethyl-3-[2-(3-pyridinyl)-3-tert-Butoxycarbonyl-thiazolid-4-oyl]indole.

To a solution of 1-Carbomethoxyethyl-3-[2-(3-pyridinyl)-3-tert-butoxycarbonylthiazolid-4-oyl]indole (2.58 g, 5.2 mmol), prepared as in Example 118, in tetrahydrofuran (20 mL) and H$_2$O (10 mL) was added lithium hydroxide monohydrate (260 mg, 6.24 mmol). After 15 min the reaction mixture was concentrated in vacuo and the residue was extracted with ethyl acetate. The aqueous phase was acidified to pH 4 with 0.5M aqueous citric acid and extracted with ethyl acetate. The combined organic extracts were dried over MgSO$_4$, filtered, and concentrated in vacuo to yield 1-Carboxyethyl-3-[2-(3-pyridinyl)-3-tert-butoxycarbonylthiazolid-4-oyl]indole (2.29 g, 92%).

Step 2. 1-Carboxyethyl-3-[2-(3-pyridinyl)thiazolid-4-oyl]indole.

1-Carboxyethyl-3-[2-(3-pyridinyl)-3-tert-butoxycarbonyl-thiazolid-4-oyl]indole (2.29 g, 4.8 mmol) was deprotected with 4M hydrochloric acid in dioxane as described in Example 1, step 5 to yield 1-Carboxyethyl-3-[2-(3-pyridinyl)thiazolid-4-oyl]indole.

NMR (CDCl$_3$, 300 MHz): δ2.90 (m, 2H), 3.15 (m, 1H), 3.38 (dd, 0.5H, J=1.2, 0.6 Hz), 4.55 (m, 2.5H), 4.75 (m, 0.5H), 5.74 (s, 0.5H), 6.0 (s, 0.5H), 7.35 (m, 5H), 7.98 (d, 0.5H, J=0.65 Hz), 8.90 (d, 0.5H, J=0.65 Hz), 8.13 (s, 0.5H), 8.23 (s, 0.5H), 8.42 (m, 2H), 8.85 (d, 1H, J=0.65 Hz). Mass Spectrum (DCI/NH$_3$): 382(M+1)$^+$.

EXAMPLE 120

Preparation of 1-carboxymethyl-3-[2-(3-pyridinyl)thiazolid-4-oyl]indole

The desired compound was prepared according to the method of Example 119, except substituting 1-Ethoxycarbonylmethyl-3-[2-(3-pyridinyl)-3-tert-butoxycarbonylthiazolid-4-oyl]indole for 1-Carbomethoxyethyl-3-[2-(3-pyridinyl)-3-tert-butoxycarbonylthiazolid-4-oyl]indole.

NMR (CDCl$_3$, 300 MHz): δ3.17–3.51 (c, 1H), 3.77–3.90 (c, 1H), 5.16–5.46 (c, 3H), 6.15 (s, 0.5H), 6.32 (s, 0.5H), 7.28–7.37 (c, 2H), 7.55–7.63 (c, 1H), 8.03–8.12 (c, 1H), 8.18–8.26 (c, 1H), 8.65–8.97 (c, 4H), 9.12–9.20 (c, 1H). Mass Spectrum (FAB): 368, 307, 289, 219, 202.

EXAMPLE 121

Preparation of 1-carbamoylmethyl-3-[2-(3-pyridinyl)thiazolid-4-oyl]indole

To a solution of 1-Carboxyethyl-3-[2-(3-pyridinyl)-thiazolid-4-oyl]indole (0.5 g, 1 mmol) prepared as in Example 119 in methylene chloride (20 mL) at 0° C. was added sodium hydride (46 mg, 1.1 mmol). After 5 min, oxalyl chloride (99 mL, 1.1 mmol) was added and the reaction mixture was stirred for 15 min. Gaseous ammonia was than bubbled through the solution for 30 sec. The reaction mixture was concentrated in vacuo and the residue partitioned between saturated aqueous NaHCO$_3$ and chloroform. The combined organic extracts were dried over MgSO$_4$, filtered and concentrated in vacuo. The residue was purified by flash chromatography (SiO$_2$, 97:3 chloroform:methanol) to afford 1-Carbamoylmethyl-3-[2-(3-pyridinyl)thiazolid-4-oyl]indole (230 mg, 50% ).

NMR (CDCl$_3$-D$_2$O, 300 MHz): δ2.75 (m, 2H), 3.14 (m, 1H), 3.35 (dd, 0.5H, J=0.9, 0.6 Hz), 3.50 (dd, 0.5H, J=0.9, 0.6 Hz), 3.65 (m, 0.5H), 3.75 (m, 0.5H), 4.55 (m, 3H), 4.65 (t, 1H, J=0.9, 0.65 Hz), 5.70 (s, 0.6H), 6.0 (s, 0.4H), 7.45 (m, 4H), 7.83 (m, 0.5H), 7.95 (m, 1H), 8.04 (s, 0.5H), 8.40 (m, 1H), 8.48 (m, 0.5H), 8.60(dd, 0.5H, J=0.2, 0.5 Hz), 8.78 (d, 1H, J=0.3 Hz). Mass Spectrum (DCI/NH$_3$): 381(M+1)$^+$.

EXAMPLE 122

Preparation of 3-[2-(3-pyridinyl)thiazolid-4-oyl]-6-carbomethoxyindole

Step 1. Indole-6-carboxylic acid.

The desired compound was prepared according to the method of Example 86, steps 1–4; except substituting methyl 4-chloro-3-nitrobenzoate for 4-Bromo-3-nitrobiphenyl.

Step 2. Methyl indole-6-carboxylate.

To a solution of indole-6-carboxylic acid (2.0 g, 12.4 mmol), prepared as described in step 1, in tetrahydrofuran (20 mL) at 0° C. was added excess diazomethane (0.30M solution in ether). After 10 min the solution was warmed to room temperature and nitrogen was bubbled through the solution for 30 min. The solution was concentrated in vacuo and the residue purified by flash chromatography (SiO$_2$, 85:15 hexane:ethyl acetate) to afford methyl indole-6-carboxylate (2.1 g, 98 %) as a white solid.

Step 3. 3-[2-(3-pyridinyl)thiazolid-4-oyl]-6-carbomethoxyindole.

The desired compound was prepared according to the method of Example 116, step 1, except substituting methyl indole-6-carboxylate for indole. The crude material was deprotected according to the method of Example 20, step 2

NMR (CDCl$_3$, 300 MHz): δ3.23 (m, 1H), 3.40 (dd, 0.5H, J=6, 10 Hz), 3.55 (dd, 0.5H, J=7, 10 Hz), 3.95 (s, 3H), 4.60 (dd, 0.5H, J=7, 7 Hz), 4.70 (dd, 0.5H, J=7, 9 Hz), 5.75 (s, 0.5H), 6.02 (s, 0.5H), 7.35 (dd, 1H, J=6, 8Hz), 7.90–8.05 (c, 2H), 8.10 (d, 0.5H, J=3 Hz), 8.18 (d, 0.5H, J=3 Hz), 8.20 (d, 1H, J=5 Hz), 8.45 (dd, 1H, J=3, 9 Hz), 8.55 (m, 0.5H), 8.60 (br d, 0.5H, J=4 Hz), 8.80 (br s, 0.5H), 8.85 (m, 0.5H), 9.10 (br s, 0.5H), 9.25 (br s, 0.5H). Mass Spectrum (DCI/NH$_3$): 368.

EXAMPLE 123

Preparation of 1-dimethylcarbamoyl-3-[2-(3-pyridinyl)thiazolid-4-oyl]-6-phenylmethoxyindole oxalate The desired compound was prepared according to the method of Example 3, except substituting 1-Dimethylcarbamoyl-3-[2-(3-pyridinyl)thiazolid-4-oyl]-6phenylmethoxyindole, prepared as in Example 52 for 1-[2-(3-pyridinyl)thiazolid-4oyl]indole.

NMR (CDCl$_3$, 300 MHz): δ8.86 (bs, 0.5H), 8.80 (bs, 0.5H), 8.61 (d, 0.5H, J=5.1 Hz), 8.54 (d, 0.5H, J=4.8 Hz), 8.27 (d, 0.5H, J=2.3 Hz), 8.24 (d, 0.5H, J=2.2 Hz), 8.01 (s, 0.5H), 7.96 (s, 0.5H), 7.94 (m, 1H), 7.42 (m, 6H), 7.12 (m, 0.5H), 5.71 (s, 0.5H), 5.15 (s, 2H), 4.67 (dd, 0.5H, J=7.7, 8.8 Hz), 4.58 (t, 0.5H, J=7.0 Hz), 3.53 (dd, 0.5H, J=7.0, 10.3 Hz), 3.4t3 (dd, 0.5H, J=7.7, 9.4 Hz), 3.18 (m, 1H), 3.03 (s, 1.5H), 3.00 (s, 1.5H) IR (CDCl₃): 3300, 3030, 2930, 1700, 1660, 1490, 1390, 1220. Mass Spectrum (DCI/NH₃): [487 (M+1)⁺, 50], 108 (100).

What is claimed is:

1. A compound selected from the group consisting of

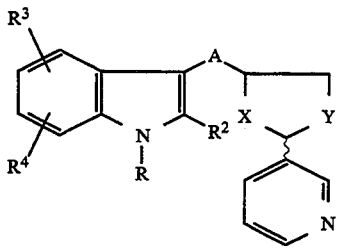

and

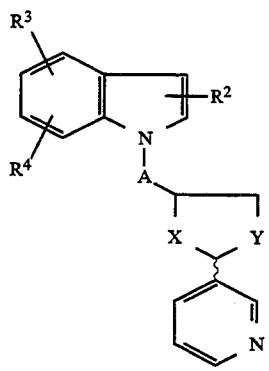

or a pharmaceutically acceptable salt thereof wherein

A is methylene, hydroxymethyl, or carbonyl, X is sulfur or NR⁵
where R⁵ is selected from
  hydrogen,
  alkyl of from one to six carbon atoms,
  formyl
  alkoyl of from one to six carbon atoms,
  alkylsulfonyl of from one to six carbon atoms,
  —C(O)NR⁶R⁷
where R⁶ and R⁷ are independently
  selected from hydrogen and alkyl of from one to six carbon atoms;
Y is sulfur or methylene;
R is selected from the group consisting of
  (a) —(CH₂)ₙC(O)NR⁶R⁷ where R⁶ and R⁷ are as previously defined and where n is from one to four;
  (b) —(CH₂)ₙC(O)OR⁸ where n is as previously defined and R⁸ is
    alkyl of from one to six carbon atoms;
    phenyl, optionally substituted with
      alkyl of from one to six carbon atoms,
      alkoxy of from one to six carbon atoms,
      halogen;
    phenylalkyl in which the alkyl portion contains from one to four carbon atoms;
    phenylalkyl as previously defined substituted on the phenyl portion with
      alkyl of from one to six carbon atoms,
      alkoxy of from one to six carbon atoms,
      halogen;
  (c) —(CH₂)ₙC(O)R⁹ where n is as previously defined and R⁹ is hydrogen or alkyl of from one to six carbon atoms;
  (d) —(CH₂)ₘCOOH where n is from one to four;
  (e) —(CH₂)ₘNR⁶R⁷ where m, R⁶ and R⁷ are as previously defined;
  (f) —(CH₂)ₙSO₂R⁸ where n and R⁸ are as previously defined;
  (g) —(CH₂)ₙSO₂NR⁶R⁷ where n, R⁶ and R⁷ are as previously defined;
R² is selected from hydrogen or alkyl of from one to six carbon atoms; and
R³ and R⁴ are independently selected from the group consisting of
  (a) hydrogen;
  (b) halogen;
  (c) alkyl of from one to six carbon atoms;
  (d) alkoxy of from one to six carbon atoms;
  (e) alkoyl of from one to six carbon atoms;
  (f) cyano;
  (g) phenylalkoxy in which the alkoxy portion contains from one to six carbon atoms;
  (h) phenoxy
  (i) benzoyl, optionally substituted with alkyl of from one to six carbon atoms;
  (j) —NR⁶R⁷ where R⁶ and R⁷ are as previously defined;
  (k) —C(O)OR⁹ where R⁹ is as previously defined; and
  (l) phenyl, optionally substituted with alkyl of from one to six carbon atoms, alkoxy of from one to six carbon atoms, or halogen.

2. A compound as defined by claim 1 having the structure:

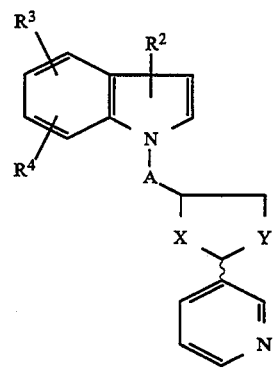

or a pharmaceutically acceptable salt thereof wherein A, X, Y, R², R³, and R⁴ are as defined therein.

3. A compound as defined by claim 2 wherein A is carbonyl, X is NR⁵ (where R⁵ is as defined therein) and Y is sulfur.

4. A compound as defined in claim 3 wherein R² and R⁵ are hydrogen or alkyl of from one to six carbon atoms, R³ is hydrogen, halogen, or phenylalkoxy in which the alkoxy portion contains from one to six carbon atoms, and R⁴ is hydrogen, or a pharmaceutically acceptable salt thereof.

5. A compound as defined in claim 4 wherein R² is hydrogen or methyl; R³ is selected from hydrogen, 5-phenylalkoxy, and 5-halo; X is NH, or a pharmaceutically acceptable salt thereof.

6. A compound as defined in claim 1 having the structure

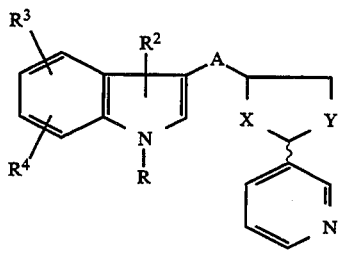

or a pharmaceutically acceptable salt thereof wherein where A, X, Y, R, $R^2$, $R^3$, and $R^4$ are as defined therein.

7. A compound as defined in claim 6 wherein A is carbonyl, X is $NR^5$ where $R^5$ is as defined therein and Y is sulfur.

8. A compound as defined in claim 7 wherein $R^2$ and $R^5$ are hydrogen, R is selected from hydrogen, —$(CH_2)_nC(O)NR^6R^7$ where n, $R^6$ and $R^7$ are as defined therein, —$(CH_2)_nC(O)OR^8$ where n and $R^8$ is as defined therein, or —$(CH_2)_mCOOH$ where m is as defined above, $R^3$ is selected from hydrogen, alkyl of from one to six carbon atoms, and phenylalkoxy in which the alkoxy portion contains from one to six carbon atoms; and $R^4$ is hydrogen, or a pharmaceutically acceptable salt thereof.

9. A compound as defined in claim 8 wherein R is —$CH_2C(O)N(CH_3)_2$, —$CH_2COOH$, —$CH_2CH_2COOH$ or tert-butoxycarbonyl; $R^3$ is selected from hydrogen, phenylmethoxy, and methyl; $R^2$ and $R^4$ are hydrogen, or a pharmaceutically acceptable salt thereof.

10. A pharmaceutical composition useful for inhibiting PAF in a mammal in need of such treatment comprising a PAF-inhibitive effective amount of a compound as defined by claim 1 in combination with a pharmaceutically acceptable carrier.

11. A method of inhibiting PAF activity in a mammal in need of such treatment comprising administering a PAF-inhibitive effective amount of a compound as defined by claim 1.

12. A method of treating PAF-mediated disorders comprising administering to a mammal in need of such treatment a therapeutically effective amount of a compound as defined by claim 1.

* * * * *